United States Patent
Tak et al.

(10) Patent No.: US 12,202,861 B2
(45) Date of Patent: *Jan. 21, 2025

(54) INDUCIBLE, TUNABLE, AND MULTIPLEX HUMAN GENE REGULATION USING CRISPR-Cpf1

(71) Applicant: The General Hospital Corporation, Boston, MA (US)

(72) Inventors: Y. Esther Tak, Charlestown, MA (US); Benjamin Kleinstiver, Boston, MA (US); J. Keith Joung, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,187

(22) Filed: Apr. 20, 2023

(65) Prior Publication Data

US 2023/0416310 A1  Dec. 28, 2023

Related U.S. Application Data

(62) Division of application No. 16/606,680, filed as application No. PCT/US2018/028898 on Apr. 23, 2018, now Pat. No. 11,667,677.

(60) Provisional application No. 62/488,585, filed on Apr. 21, 2017.

(51) Int. Cl.
| | |
|---|---|
| *C07K 14/005* | (2006.01) |
| *A61K 38/00* | (2006.01) |
| *C12N 9/22* | (2006.01) |
| *C12N 9/52* | (2006.01) |
| *C12N 15/11* | (2006.01) |
| *C12N 15/62* | (2006.01) |

(52) U.S. Cl.
CPC .............. *C07K 14/005* (2013.01); *C12N 9/22* (2013.01); *C12N 9/52* (2013.01); *C12N 15/111* (2013.01); *C12N 15/62* (2013.01); *A61K 38/00* (2013.01); *C07K 2319/03* (2013.01); *C12N 2310/153* (2013.01); *C12N 2310/20* (2017.05); *C12N 2710/16222* (2013.01); *C12N 2800/30* (2013.01)

(58) Field of Classification Search
CPC .... C07K 14/005; C07K 2319/03; C12N 9/22; C12N 9/52; C12N 15/111; C12N 15/62; C12N 2310/153; C12N 2310/20; C12N 2710/16222; C12N 2800/30; C12N 15/63; A61K 38/00

See application file for complete search history.

(56) References Cited

U.S. PATENT DOCUMENTS

| | | | |
|---|---|---|---|
| 10,793,828 B2 | 10/2020 | Haugwitz et al. | |
| 11,286,478 B2 | 3/2022 | Zhang et al. | |
| 11,667,677 B2 * | 6/2023 | Tak ........................ | C12N 15/62 424/234.1 |
| 2003/0017149 A1 | 1/2003 | Hoeffler et al. | |
| 2007/0020627 A1 | 1/2007 | Barbas, III | |
| 2007/0213269 A1 | 9/2007 | Barbas, III et al. | |
| 2011/0236894 A1 | 9/2011 | Rao et al. | |
| 2011/0294873 A1 | 12/2011 | Mermod et al. | |
| 2012/0115227 A1 | 5/2012 | Cohen-Haguenauer et al. | |
| 2015/0315252 A1 | 11/2015 | Haugwitz et al. | |
| 2016/0208243 A1 | 7/2016 | Zhang et al. | |
| 2016/0215280 A1 | 7/2016 | Fanucchi et al. | |
| 2017/0175136 A1 | 6/2017 | Stamatoyannopoulos et al. | |
| 2019/0351074 A1 | 11/2019 | Ahituv et al. | |

FOREIGN PATENT DOCUMENTS

| | | |
|---|---|---|
| WO | WO 2003/072788 | 9/2003 |
| WO | WO 2012/047726 | 4/2012 |
| WO | WO 2013/176772 | 11/2013 |
| WO | WO 2014/152432 | 9/2014 |
| WO | WO 2015/139139 | 9/2015 |
| WO | WO 2016/115355 | 7/2016 |
| WO | WO 2016/191684 | 12/2016 |
| WO | WO 2016/205711 | 12/2016 |
| WO | WO 2017/015015 | 1/2017 |
| WO | WO 2017/031370 | 2/2017 |
| WO | WO 2017/141173 | 8/2017 |
| WO | WO 2018/071892 | 4/2018 |
| WO | WO 2019/222670 | 11/2019 |
| WO | WO 2021/108501 | 6/2021 |
| WO | WO 2021/243289 | 12/2021 |

OTHER PUBLICATIONS

Tak et al., Inducible, tunable and multiplex human gene regulation using CRISPR-Cpf1-based transcription factors. bioRxiv preprint doi: https://doi.org/10.1101/150656; this version posted Jun. 15, 2017: 21 pages. (Year: 2017).*
Notice of Allowance in Japanese Appln. No. 2019-556605, dated Oct. 3, 2023, 6 pages (with English translation).
Office Action in Chinese Appln. No. 201880041218.8, dated Sep. 2, 2023, 20 pages (with English translation).
Office Action in Chinese Appln. No. 201880041218.8, dated Dec. 1, 2023, 20 pages (with English translation).
Adamson et al., "A Multiplexed Single-Cell CRISPR Screening Platform Enables Systematic Dissection of the Unfolded Protein Response," Cell, Dec. 2016, 167(7):1867-1882.
Andersson et al., "A Unified Architecture of Transcriptional Regulatory Elements," Trends in Genetics, Aug. 2015, 31(8):426-433, 8 pages.
Bao et al., "Orthogonal Genetic Regulation in Human Cells Using Chemically Induced CRISPR/Cas9 Activators," ACS Synthetic Biology, Apr. 2017, 6(4):686-693, 8 pages.

(Continued)

*Primary Examiner* — Ganapathirama Raghu
(74) *Attorney, Agent, or Firm* — Fish & Richardson P.C.

(57) ABSTRACT

Drug-inducible, tunable, and multiplexable Clustered Regularly Interspaced Short Palindromic Repeats from *Prevotella* and *Francisella* 1 (Cpf1)-based activators, and methods of use thereof.

8 Claims, 12 Drawing Sheets

Specification includes a Sequence Listing.

(56) References Cited

OTHER PUBLICATIONS

Baron-Benhamou et al, "Using the LambdaN Peptide to Tether Proteins to RNAs," Methods in Molecular Biology, Jan. 2004, 257:135-153.

Bikard et al., "Programmable repression and activation of bacterial gene expression using an engineered CRISPR-Cas system," Nucleic Acids Research, Jun. 2013, 41(15):7429-7437.

Bird et al., "A dual role for zinc fingers in both DNA binding and zinc sensing by the Zap1 transcriptional activator," EMBO J., Jul. 2000, 19(14):3704-3713.

Chavez et al., "Comparison of Cas9 activators in multiple species," Nature Methods, Jul. 2016, 13(7):563-567, 7 pages.

Chavez et al., "Highly efficient Cas9-mediated transcriptional programming," Nature Methods, Apr. 2015, 12(4):326-328.

Cong et al., "Multiplex genome engineering using CRISPR/Cas systems," Science, Feb. 2013, 339(6121):819-823.

Deltcheva et al., "CRISPR RNA maturation by trans-encoded small RNA and host factor RNase III," Nature, Mar. 2011, 471(7340):602-607.

Dong et al., "The crystal structure of Cpf1 in complex with CRISPR RNA," Nature, Apr. 2016, 532(7600):522-526.

Doudna & Charpentier., "Genome editing. The new frontier of genome engineering with CRISPR-Cas9," Science, Nov. 2014, 346(6213):1258096, 12 pages.

EP Extended European Search Report in European Appln. No. 18787309.6, dated Jan. 11, 2021, 11 pages.

Fagerlund et al., "The Cpf1 CRISPR-Cas protein expands genome-editing tools," Genome Biol., Dec. 2015, 16(1):251, 3 pages.

Fonfara et al., "The CRISPR-associated DNA-cleaving enzyme Cpf1 also processes precursor CRISPR RNA," Nature, Apr. 2016, 532(7600):517-521, 19 pages.

Frock et al., "Genome-wide detection of DNA double-stranded breaks induced by engineered nucleases," Nat. Biotechnol., Feb. 2015, 33(2):179-186, 10 pages.

Gao et al., "Complex transcriptional modulation with orthogonal and inducible dCas9 regulators," Nature Methods, Dec. 2016, 13(12):1043-1049.

Gilbert et al., "Genome-Scale CRISPR-Mediated Control of Gene Repression and Activation," Cell, Oct. 2014, 159(3):647-661.

Guo et al., "An inducible CRISPR-ON system for controllable gene activation in human pluripotent stem cells," Protein & Cell, May 2017, 8(5):379-393.

Han al., "Synergistic drug combinations for cancer identified in a CRISPR screen for pairwise genetic interactions," Nature Biotechnology, May 2017, 35(5):463, 15 pages.

Hsu et al., "Development and applications of CRISPR-Cas9 for genome engineering," Cell, Jun. 2014, 157(6):1262-1278.

International Preliminary Report on Patentability in International Appln. No. PCT/US18/28898, dated Oct. 22, 2019, 9 pages.

International Search Report and Written Opinion in International Appln. No. PCT/US18/28898, dated Jul. 23, 2018, 12 pages.

International Search Report and Written Opinion in International Appln. No. PCT/US2014/027335, dated Jul. 16, 2014, 13 pages.

International Search Report and Written Opinion in International Appln. No. PCT/US2017/056738, dated Mar. 6, 2018, 16 pages.

International Search Report and Written Opinion in International Appln. No. PCT/US2019/032937, dated Oct. 17, 2019, 17 pages.

International Search Report and Written Opinion in International Appln. No. PCT/US2020/062166, dated May 4, 2021, 13 pages.

International Search Report and Written Opinion in International Appln. No. PCT/US2021/034996, dated Sep. 16, 2021, 12 pages.

Jinek et al., "A programmable dual-RNA-guided DNA endonuclease in adaptive bacterial immunity," Science, Aug. 2012, 337(6096):816-821.

Jinek et al., "RNA-programmed genome editing in human cells," Elife 2, Jan. 2013, 2:e00471, 9 pages.

Kabadi et al., "Multiplex CRISPR/Cas9-based genome engineering from a single lentiviral vector," Nucleic Acids Res., 2014, 42(19):e147.

Khalil et al., "A Synthetic Biology Framework for Programming Eukaryotic Transcription Functions," Cell, Aug. 2012, 150(3):647-658.

Kim et al., "Digenome-seq: genome-wide profiling of CRISPR-Cas9 off-target effects in human cells," Nat. Methods, Mar. 2015, 12(3):237-243.

Kim et al., "Efficient Transcriptional Gene Repression by Type V-A CRISPR-Cpf1 from Eubacterium eligens," ACS Synthetic Biology, Jul. 2017, 6(7):1273-1282.

Kim et al., "Genome-wide analysis reveals specificities of Cpf1 endonucleases in human cells," Nature Biotechnology, Aug. 2016, 34(8):863-868.

Kleinstiver et al., "Genome-wide specificities of CRISPR-Cas Cpf1 nucleases in human cells," Nature Biotechnology, Aug. 2016, 34(8):869-874.

Kleinstiver et al., "High-fidelity CRISPR-Cas9 nucleases with no detectable genome-wide off-target effects," Nature, Jan. 2016, 529(7587):490-495, 17 pages.

Konermann et al., "Genome-scale transcriptional activation by an engineered CRISPR-Cas9 complex," Nature, Jan. 2015, 517(7536):583-588.

Li et al., "Identification of critical base pairs required for CTCF binding in motif M1 and M2," Protein Cell, Mar. 2017, 8(7):544-549, 6 pages.

Lin et al., "A CRISPR Approach for Reactivating Latent HIV-1," Molecular Therapy, Mar. 2016, 24(3):416-418.

Lin et al., "Cellular toxicity induced by SRF-mediated transcriptional squelching," Toxicological Sciences, Mar. 2007, 96(1):83-91.

Maeder et al., "CRISPR RNA-guided activation of endogenous human genes," Nat. Methods, Oct. 2013, 10(10):977-979.

Maeder et al., "Genome-editing Technologies for Gene and Cell Therapy," Mol. Ther., Mar. 2016, 24(3):430-446.

Maji et al., "Multidimensional chemical control of CRISPR-Cas9," Nature Chemical Biology, Jan. 2017, 13(1):9-11.

Makarova et al., "An updated evolutionary classification of CRISPR-Cas systems," Nat. Rev. Microbiol., Nov. 2015, 13(11):722-736.

Mali et al., "RNA-guided human genome engineering via Cas9," Science, Feb. 2013, 339(6121):823-826, 5 pages.

Matis et al., "Differential and opposed transcriptional effects of protein fusions containing the VP16 activation domain," FEBS Letters, Jun. 2001, 499(1-2):92-96.

Nissim et al., "Multiplexed and programmable regulation of gene networks with an integrated RNA and CRISPR/Cas toolkit in human cells," Molecular Cell, May 2014, 54(4):698-710.

Notice of Acceptance in Australian Appln. No. 2018254616, dated Jul. 13, 2022, 4 pages.

Office Action in Australian Appln. No. 2018254616, dated Oct. 11, 2021, 5 pages.

Office Action in Chinese Appln. No. 201880041218.8, dated Feb. 8, 2023, 27 pages (with English translation).

Office Action in Japanese Appln. No. 2019-556605, dated Mar. 29, 2022, 8 pages (with English translation).

Office Action in Japanese Appln. No. 2019-556605, dated Oct. 18, 2022, 6 pages (with English translation).

Perez-Pinera et al., "RNA-guided gene activation by CRISPR-Cas9-based transcription factors," Nat. Methods, Oct. 2013, 10(10):973-976.

Polstein & Gersbach, "A light-inducible CRISPR-Cas9 system for control of endogenous gene activation," Nature Chemical Biology, Mar. 2015, 11(3):198-200.

Qi et al, "Repurposing CRISPR as an RNA-Guided Platform for Sequence-Specific Control of Gene Expression," Cell, Feb. 2013, 152:1173-1183.

Rivera et al., "Dimerizer-mediated regulation of gene expression in vivo," Cold Spring Harbor Protocols, Jul. 2012, 2012(7):821-824.

Rojano et al., "Regulatory variants: from detection to predicting impact," Briefings in Bioinformatics, Sep. 2019, 20(5):1639-1654.

Sander & Joung, "CRISPR-Cas systems for editing, regulating and targeting genomes," Nat. Biotechnol., Apr. 2014, 32(4):347-355.

Schunder et al., "First indication for a functional CRISPR/Cas system in Francisella tularensis," Int. J. Med. Microbiol., Mar. 2013, 303(2):51-60.

(56) References Cited

OTHER PUBLICATIONS

Shen et al., "Combinatorial CRISPR-Cas9 screens for de novo mapping of genetic interactions," Nature Methods, Jun. 2017, 14(6):573, 9 pages.

Slaymaker et al., "Rationally engineered Cas9 nucleases with improved specificity," Science, Jan. 2016, 351(6268):84-88.

Tak et al.: "Inducible and multiplex gene regulation using CRISPR-Cpf1-based transcription factors," Nature Methods, Oct. 2017, 14(12):1163-1166.

Tang et al., "A CRISPR-Cpf1 system for efficient genome editing and transcriptional repression in plants," Nature Plants, Feb. 2017, 3:17018, 5 pages.

Tsai et al., "Dimeric CRISPR RNA-guided FokI nucleases for highly specific genome editing," Nat. Biotechnol., Jun. 2014, 32(6):569-576.

Tsai et al., "GUIDE-seq enables genome-wide profiling of off-target cleavage by CRISPR-Cas nucleases," Nat. Biotechnol., Feb. 2015, 33(2):187-197.

Wang et al., "Unbiased detection of off-target cleavage by CRISPR-Cas9 and TALENs using integrase-defective lentiviral vectors," Nat. Biotechnol., Feb. 2015, 33(2):175-178.

Wong et al., "Multiplexed barcoded CRISPR-Cas9 screening enabled by CombiGEM," Proc. Natl. Acad. Sci. USA., Mar. 2016, 113(9):2544-2549.

Wright et al., "Biology and Applications of CRISPR Systems: Harnessing Nature's Toolbox for Genome Engineering," Cell, Jan. 2016, 164(1-2):29-44.

Xie et al., "Boosting CRISPR/Cas9 multiplex editing capability with the endogenous tRNA-processing system," Proc. Natl. Acad. Sci. USA., Mar. 2015, 112(11):3570-3575.

Xu et al., "Empower multiplex cell and tissue-specific CRISPR-mediated gene manipulation with self-cleaving ribozymes and tRNA," Nucleic Acids Res., Mar. 2017, 45(5):e28, 9 pages.

Yamano et al., "Crystal structure of Cpf1 in complex with guide RNA and target DNA," Cell, May 2016, 165(4):949-962.

Zetsche et al., "A split-Cas9 architecture for inducible genome editing and transcription modulation," Nature Biotechnology, Feb. 2015, 33(2):139-142.

Zetsche et al., "Cpf1 is a single RNA-guided endonuclease of a class 2 CRISPR-Cas system," Cell, Oct. 2015, 163(3):759-771.

Zetsche et al., "Multiplex gene editing by CRISPR-Cpf1 using a single crRNA array," Nature Biotechnology, Jan. 2017, 35(1):31-34.

Zhang et al., "Multiplex gene regulation by CRISPR-ddCpf1," Cell Discovery, Jun. 2017, 3(6):17018, 9 pages.

Office Action in Canadian Appln. No. 3,059,208, dated May 9, 2024, 4 pages.

* cited by examiner

INDUCIBLE, TUNABLE, AND MULTIPLEX HUMAN GENE REGULATION USING CRISPR-Cpf1

CLAIM OF PRIORITY

This application is divisional application of U.S. patent application Ser. No. 16/606,680, which is a national stage application under 35 USC § 371 of International Application No. PCT/US2018/028898, filed Apr. 23, 2018, which claims the benefit of U.S. Patent Application Ser. No. 62/488,585, filed on Apr. 21, 2017.

The entire contents of the foregoing are hereby incorporated by reference.

FEDERALLY SPONSORED RESEARCH OR DEVELOPMENT

This invention was made with Government support under Grant Nos. GM107427 and GM118158 awarded by the National Institutes of Health. The Government has certain rights in the invention.

SEQUENCE LISTING

This application contains a Sequence Listing that has been submitted electronically as an XML file named "40978-0278002_SL_ST26.XML." The XML file, created on Jun. 22, 2023, is 114,826 bytes in size. The material in the XML file is hereby incorporated by reference in its entirety.

TECHNICAL FIELD

Described herein are drug-inducible, tunable, and multiplexable Cpf1-based activators, and methods of use thereof.

BACKGROUND

RNA-guided CRISPR nucleases have revolutionized both biology and therapeutics with their ease of reprogrammability to recognize target DNA sequences. The widely used Cas9 from *Streptococcus pyogenes* (SpCas9) can be targeted to a specific DNA sequence with an associated complementary guide RNA (gRNA) provided that a protospacer adjacent motif (PAM) of the form NGG is also present.

SUMMARY

The present invention is based, at least in part, on the development of constitutively active and chemically inducible dCpf1-based transcriptional activator platforms, and methods of use thereof, including methods that use multiplex Cpf1 gRNA expression to achieve synergistic or combinatorial activation of endogenous genes in human cells.

Thus, provided herein are fusion proteins that include a catalytically inactive (i.e., catalytically inactive for DNA endonuclease activity) Clustered Regularly Interspaced Short Palindromic Repeats from *Prevotella* and *Francisella* 1 (Cpf1) from Lachnospiraceae bacterium ND2006 protein Cpf1 (dLbCpf1) fused to at least one activation domain (e.g., 1, 2, 3, 4, or more activation domains), preferably wherein the activation domain is a synthetic VPR activator (i.e., comprising four copies of VP16, a human NF-κB p65 activation domain, and an Epstein-Barr virus R transactivator (Rta)). Other activation domains include VP64, Rta, NF-κB p65, and p300, with optional intervening linkers between the Cpf1 and/or each activation domain.

Further, provided herein are fusion proteins that include a catalytically inactive Lachnospiraceae bacterium ND2006 Cpf1 (dLbCpf1) fused to a conditional dimerization domain, with optional intervening linkers between the Cpf1 and/or each activation domain. In some embodiments, the conditional dimerization domain is DmrA or DmrC. These fusion proteins can be provided in compositions or kits that also include a second fusion protein comprising at least one activation domain (e.g., 1, 2, 3, 4, or more activation domains) fused to a second conditional dimerization domain that dimerizes with the conditional dimerization in the fusion protein of claim 2 in the presence of a dimerizing agent, with an optional intervening linker between each of the activation domain(s) and/or the second dimerizing domain. In some embodiments, the conditional dimerization in the fusion protein of claim 2 is DmrA, and the second conditional dimerization domain is DmrC, or (ii) the conditional dimerization in the fusion protein of claim 2 is DmrC, and the second conditional dimerization domain is DmrA. In some embodiments, the activation domain is VP64, Rta, NF-κB p65, VPR, or p300.

Also provided are kits comprising the fusion proteins, and/or nucleic acids encoding a fusion protein as described herein, optionally with the dimerizing agent.

Also provided herein are nucleic acids encoding the fusion proteins described herein, vectors comprising the nucleic acids, and cells comprising the nucleic acids and/or vectors and optionally expressing the fusion proteins.

Further, provided are methods for increasing expression of a target gene in a cell, the method comprising contacting the cell with, or expressing in the cell, one or more of:
  (i) a fusion protein that includes a catalytically inactive Lachnospiraceae bacterium ND2006 protein Cpf1 (dLbCpf1) fused to at least one activation domain (e.g., 1, 2, 3, 4, or more activation domains), and at least one crRNA that directs the fusion protein to a regulatory region, e.g., a promoter region, of the target gene; and/or
  (ii) a first fusion protein that includes a catalytically inactive Lachnospiraceae bacterium ND2006 Cpf1 (dLbCpf1) fused to a conditional dimerization domain, with optional intervening linkers between the Cpf1 and/or each activation domain, and a second fusion protein comprising an activation domain fused to a second conditional dimerization domain that dimerizes with the conditional dimerization in the first fusion protein in the presence of a dimerizing agent (with an optional intervening linker between the activation domain and the second dimerizing domain), and at least one crRNA that directs the fusion protein to a regulatory region, e.g., a promoter region, of the target gene.

Also provided are methods of increasing expression of a plurality of target genes (e.g., two, three, four, or more) in a cell, the method comprising contacting the cell with, or expressing in the cell, one or more of:
  (i) a fusion protein that includes a catalytically inactive Lachnospiraceae bacterium ND2006 protein Cpf1 (dLbCpf1) fused to at least one activation domain (e.g., 1, 2, 3, 4, or more activation domains), and at least one nucleic acid encoding a plurality of crRNAs that each direct the fusion protein to a regulatory region, e.g., a promoter region, of one of the target genes;
  (ii) a first fusion protein that includes a catalytically inactive Lachnospiraceae bacterium ND2006 Cpf1 (dLbCpf1) fused to a conditional dimerization domain, with optional intervening linkers between the Cpf1 and/or each activation domain, and a second fusion protein comprising an activation domain fused to a second conditional dimerization domain that dimerizes with the conditional dimerization in the first fusion protein in the presence of a dimerizing agent, and at least one nucleic acid encoding a plurality of crRNAs that each direct the fusion protein to a regulatory region, e.g., a promoter region, of one of the target genes.

In some embodiments, the cell is a mammalian cell, e.g., a human cell.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

Figure 1A:
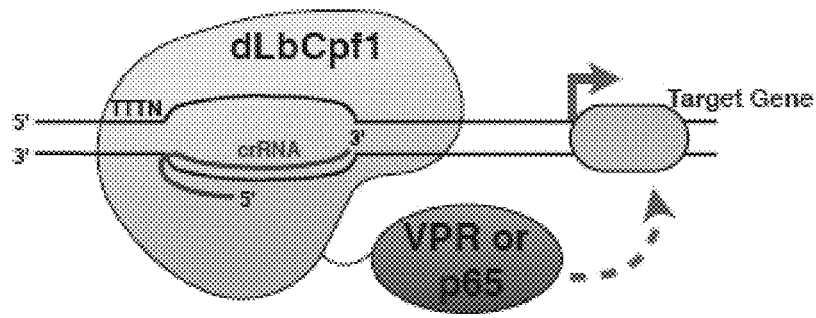
FIGS. 1A-1E. Targeted human endogenous gene regulation using individual crRNAs with dLbCpf1-based activators (A) Schematic showing direct dLbCpf1-VPR and dLbCpf-p65 activator fusion proteins.

(B) Activities of dLbCpf1-p65 or dLbCpf1-VPR using single crRNAs at three endogenous human genes (HBB, AR, and NPY1R) in human HEK293 cells. Relative activation of the indicated gene promoters was measured by RT-qPCR. Three separate individual crRNAs were targeted within promoter sequence 1 kb upstream of the transcription start site for each gene. Relative mRNA expression is calculated by comparison to the control sample in which no crRNA is expressed. (C) Analysis of various crRNAs targeted to the human CD5 and CD22 promoters. 32 crRNAs (16 for each gene) were designed to target sites located within promoter sequences 1 kb upstream or 500 bps downstream of the TSS of each gene. Repetitive sequences were not targeted. After 72 hours post-transfection, cells were stained with fluorescently labeled antibody for CD5 or CD22 protein and fluorescent-positive cells were quantified by flow cytometry. Error bars represent s.e.m. for three biological replicates. Black circles indicate samples that are significantly different (Student t-test, two-tailed test assuming equal variance, $p<0.05$) compared to controls in which no crRNA was expressed. (D) Schematic illustrating drug-inducible bi-partite dLbCpf1-based activator fusion proteins. dLbCpf1 is fused to one to four DmrA domains and VPR or p65 is fused to a DmrC domain. Because DmrA and DmrC interact only in the presence of an A/C-heterodimerizer drug (red diamond), the bi-partite activator is only reconstituted in the presence of the drug. (E) Activities of drug-inducible bi-partite dLbCpf1-based activators using single crRNAs at three endogenous human genes (HBB, AR, and NPY1R) in human HEK293 cells. Relative activation of the indicated gene promoters was measured by RT-qPCR. The crRNA used for each promoters was the one that showed the highest activity in (B) above. Data shown in (B) and (E) represent three biological independent replicates and error bars indicate standard deviation (SD) of three technical replicates.

FIGS. 2A-2I. Multiplex and synergistic regulation of endogenous human genes by dLbCpf1-based activators (A) Schematic of an expression cassette designed to express multiple gRNAs encoded on a single transcript. The arrows indicate cleavage sites being processed by the RNase activity of dLbCpf1. (B) Schematic illustrating multiplex expression of three crRNAs each targeted to a different endogenous gene promoter in a single cell. (C) Simultaneous activation of three endogenous human genes using crRNAs expressed from a multiplex transcript or from individual transcripts with dLbCpf1-VPR direct fusions (left panel), dLbCpf1-DmrA(×4) and DmrC-VPR fusions (middle panel), and dLbCpf1-DmrA(×4) and DmrC-p65 fusions (right panel). Transcripts were measured in HEK293 cells using RT-qPCR with relative mRNA expression calculated by comparison to the control sample in which no crRNA is expressed. (D) Activities of MST crRNA with different dLbCpf1-based activators in human U2OS cells. Graphs showing activation of three endogenous human genes with dLbCpf1-VPR direct fusions, dLbCpf1-DmrA(×4) and DmrC-p65 fusions, and dLbCpf1-DmrA(×4) and DmrC-VPR fusions and crRNAs expressed from a multiplex single transcript (MST) or from transcripts encoding a single crRNA. RNA expression was measured by RT-qPCR and relative expression shown was calculated by comparison to a control sample in which no crRNA is expressed. (E) Schematic illustrating multiplex expression of three crRNAs each targeted to the same endogenous gene promoter in the same cell. (F) Activities of direct dLbCpf1-p65 or dLbCpf1-VPR fusions with sets of three crRNAs expressed from a multiplex transcript or from individual transcripts on the HBB, AR, or NPY1R endogenous gene promoters. Transcripts were measured in HEK293 cells using RT-qPCR with relative mRNA expression calculated by comparison to the control sample in which no crRNA is expressed. (G) Activities of dLbCpf1-DmrA(×4) and DmrC-VPR fusions or with dLbCpf1-DmrA(×4) and DmrC-p65 fusions with sets of three crRNAs expressed from a multiplex transcript or from individual transcripts on the HBB, AR, or NPY1R endogenous gene promoters. Transcripts were measured in HEK293 cells using RT-qPCR with relative mRNA expression calculated by comparison to the control sample in which no crRNA is expressed. Data shown in (C), (D), (F) and (G) represent three biological independent replicates and error bars indicate standard deviation (SD) of three technical replicates. hU6, human U6 Polymerase III promoter; DR; direct repeat sequence. (H) Inducibility and reversibility of A/C heterodimerizer drug-regulated dLbCpf1-based activators. To measure the kinetics of activator induction, HEK293 cells were transfected with plasmids expressing dLbCpf1-DmrA(×4), DmrC-p65, and MST crRNAs targeting the human HBB or AR promoters. 34 hours after transfection, these cells were split into two cultures: one with media containing A/C heterodimerizer (500 uM) (top, black) and one with media lacking the A/C heterodimerizer (bottom, grey). Cells were collected at various time points and relative mRNA expression levels were measured by RT-qPCR compared to a negative control. (I) To measure the kinetics of reversibility, HEK293 cells were transfected as in (H). 24 hours after transfection, A/C heterodimerizer (500 uM) was added to the medium. 10 hours later, these cells were split into two cultures: one with media containing A/C heterodimerizer (500 uM) (top, blue) and one with media lacking the A/C heterodimerizer (bottom, purple). Cells were collected at various time points and relative mRNA expression levels were measured by RT-qPCR compared to a negative control. Error bars represent s.e.m. of three biological replicates.

DETAILED DESCRIPTION

Catalytically inactive forms of SpCas9 ("dead" SpCas9 or dSpCas9) nucleases have been fused with transcriptional activator or repressor domains to alter the expression of genes individually or genome-wide for library screens in mammalian cells[1-4], although efficient activation has required multiple regulatory domains to be recruited to a single promoter[5]. Both small molecule- and light-inducible dCas9-based gene regulatory fusions have also been described, providing additional important capabilities to this platform[6-10]. Recently described CRISPR-Cpf1 nucleases offer important additional capabilities beyond those of SpCas9 including shorter length gRNAs, the capability to target alternative T-rich PAM sequences, and processing of multiple guide RNAs from a single transcript by the Cpf1 nuclease itself[11]. However, to the present inventors' knowledge "dead" Cpf1-based gene regulators have only been used to date to repress gene expression in bacteria[12] and a plant (Arabidopsis)[13] and have not been shown to work in mammalian cells or for activating a target gene. Herein we describe constitutively active and chemically inducible dCpf1-based transcriptional activator platforms and show that multiplex Cpf1 gRNA expression can be leveraged to achieve synergistic or combinatorial activation of endogenous genes in human cells.

To our knowledge, the results reported here provide the first demonstrations that RNA-guided Cpf1-based fusions can be used to activate endogenous gene expression in any cell type and the first use of Cpf1-derived gene regulatory proteins in human cells. The orthogonal PAM recognition specificities of LbCpf1 compared with SpCas9 (TTTN versus NGG) open up a new range of targetable sequences for RNA-guided activator proteins. Given the reported higher genome-wide specificities of LbCpf1 compared with SpCas9[14,15] dLbCpf1 activators may have comparable specificities to dSpCas9 activators, which have been shown by RNA-seq to cause few, if any, off-target gene activation events.

The present work also established drug-inducible dLbCpf1 activators that can be used to control gene regulation in multiple ways. These activators include paired fusion proteins, a first fusion protein that includes a catalytically inactive Lachnospiraceae bacterium ND2006 Cpf1 (dLbCpf1) fused to a conditional dimerization domain, with optional intervening linkers between the Cpf1 and/or each activation domain, and a second fusion protein comprising an activation domain fused to a second conditional dimerization domain that dimerizes with the conditional dimerization in the first fusion protein in the presence of a dimerizing agent, with an optional intervening linker between the activation domain and the second dimerizing domain. The bi-partite nature of these activators enables turning their activity on or off with a cell-permeable A/C dimerizer drug, which provides a useful capability for experimental systems. In addition, the level of activation desired can be tuned by increasing the number of DmrA dimerizer domains fused to dLbCpf1, which presumably leads to recruitment of increasing numbers of DmrC-activator fusions to a given promoter.

Changing the activation domain used in the DmrC fusion influenced the extent of activation observed. Somewhat surprisingly and in contrast to previous results with dSpCas9-based activators, the p65 domain (with individual crRNAs) more consistently activated the three gene promoters examined than did the synthetic VPR activator (which contains six strong activation domains). With multiple crRNAs directed to a target promoter, the p65 domain provided stronger activation for the two genes on which synergism was observed. The ability to use the naturally occurring p65 activation domain rather than the synthetic VPR is advantageous as it avoids undesirable side effects (e.g., squelching) caused by very potent activators[16,17] Beyond its utility for gene activation, this drug-inducible, multiplex dCpf1-based platform can be used to enable targeted recruitment of other heterologous proteins or functional domains to any endogenous genomic locus of interest.

The present work also demonstrated that a key advantage of the Cpf1 platform, the ability to more simply encode multiple crRNAs on a single transcript, can be leveraged to achieve multiplex activation of endogenous human genes in the same single cell. Multiplex regulation using dSpCas9 gene regulatory proteins is challenging due to substantial recombination between promoters if gRNAs are expressed from separate promoters[18] or the need for additional accessory RNA sequences, promoters, or trans-acting factors if multiple gRNAs are expressed from a single transcript[19-25]. By contrast, the shorter ~40 nt length of crRNAs used by Cpf1 enables two or three crRNAs to be readily encoded on a single oligonucleotide thereby enabling the leveraging of chip-based synthesis to construct precise user-specified combinations of crRNAs targeted to genes of interest; doing the same with dSpCas9 gRNAs is more challenging due to the longer-length (~100 nt) guide RNAs required and the accessory sequences and factors required to enable processing from a single transcript. Thus, these results demonstrate the feasibility of performing methods including multiplex library screens in which the expression of two or more genes are simultaneously regulated, thereby enabling the analysis of more complex cellular phenotypes using this approach.

Cpf1

Clustered, regularly interspaced, short palindromic repeat (CRISPR) systems encode RNA-guided endonucleases that are essential for bacterial adaptive immunity[26]. CRISPR-associated (Cas) nucleases can be readily programmed to cleave target DNA sequences for genome editing in various organisms[27-30]. One class of these nucleases, referred to as Cas9 proteins, complex with two short RNAs: a crRNA and a trans-activating crRNA (tracrRNA)[31,32]. The most commonly used Cas9 ortholog, SpCas9, uses a crRNA that has 20 nucleotides (nt) at its 5' end that are complementary to the "protospacer" region of the target DNA site. Efficient cleavage also requires that SpCas9 recognizes a protospacer adjacent motif (PAM). The crRNA and tracrRNA are usually combined into a single ~100-nt guide RNA (gRNA)[31,33-35] that directs the DNA cleavage activity of SpCas9. The genome-wide specificities of SpCas9 nucleases paired with different gRNAs have been characterized using many different approaches[36-39]. SpCas9 variants with substantially improved genome-wide specificities have also been engineered[40-41].

Recently, a Cas protein named Cpf1 has been identified that can also be programmed to cleave target DNA sequences[42-45]. Unlike SpCas9, Cpf1 requires only a single 42-nt crRNA, which has 23 nt at its 3' end that are complementary to the protospacer of the target DNA sequence[44]. Furthermore, whereas SpCas9 recognizes an NGG PAM sequence that is 3' of the protospacer, AsCpf1 and LbCp1 recognize TTTN PAMs that are found 5' of the protospacer[44]. Early experiments with AsCpf1 and LbCpf1 showed that these nucleases can be programmed to edit target sites in human cells[44] but they were tested on only a small number of sites. On-target activities and genome-wide specificities of both AsCpf1 and LbCpf1 were characterized in Kleinstiver & Tsai et al., Nature Biotechnology 2016.

Provided herein are fusion proteins comprising LbCpf1. The LbCpf1 wild type protein sequence is as follows:

```
LbCpf1-Type V CRISPR-associated protein Cpf1 [Lachnospiraceae bacterium
ND2006], GenBank Acc No. WP 051666128.1
                                                              (SEQ ID NO: 1)
   1 MLKNVGIDRL DVEKGRKN MS KLEKFTNCYS LSKTLRFKAI PVGKTQENID NKRLLVEDEK

61 RAEDYKGVKK LLDRYYLSFI NDVLHSIKLK NLNNYISLER KKTRTEKENK ELENLEINLR

121 KEIAKAFKGN EGYKSLFKKD IIETILPEFL DDKDEIALVN SENGFTTAFT GFFDNRENME

181 SEEAKSTSIA FRCINENLTR YISNMDIFEK VDAIFDKHEV QEIKEKILNS DYDVEDFFEG

241 EFFNFVLTQE GIDVYNAIIG GFVTESGEKI KGLNEYINLY NQKTKQKLPK FKPLYKQVLS

301 DRESLSFYGE GYTSDEEVLE VERNTLNKNS EIFSSIKKLE KLFKNFDEYS SAGIFVKNGP

361 AISTISKDIF GEWNVIRDKW NAEYDDIHLK KKAVVTEKYE DDRRKSFKKI GSFSLEQLQE

421 YADADLSVVE KLKEIIIQKV DEIYKVYGSS EKLFDADFVL EKSLKKNDAV VAIMKDLLDS

481 VKSFENYIKA FFGEGKETNR DESFYGDEVL AYDILLKVDH IYDAIRNYVT QKPYSKDKFK

541 LYFQNPQFMG GWDKDKETDY RATILRYGSK YYLAIMDKKY AKCLQKIDKD DVNGNYEKIN

601 YKLLPGPNKM LPKVFFSKKW MAYYNPSEDI QKIYKNGTEK KGDMENLNDC HKLIDFFKDS

661 ISRYPKWSNA YDENESETEK YKDIAGFYRE VEEQGYKVSF ESASKKEVDK LVEEGKLYMF

721 QIYNKDESDK SHGTPNLHTM YFKLLEDENN HGQIRLSGGA ELFMRRASLK KEELVVHPAN

781 SPIANKNPDN PKKTTTLSYD VYKDKRFSED QYELHIPIAI NKCPKNIFKI NTEVRVLLKH

841 DDNPYVIGID RGERNLLYIV VVDGKGNIVE QYSLNEIINN FNGIRIKTDY HSLLDKKEKE

901 RFEARQNWTS IENIKELKAG YISQVVHKIC ELVEKYDAVI ALEDLNSGFK NSRVKVEKQV

961 YQKFEKMLID KLNYMVDKKS NPCATGGALK GYQITNKFES FKSMSTQNGF IFYIPAWLTS

1021 KIDPSTGFVN LLKTKYTSIA DSKKFISSED RIMYVPEEDL FEFALDYKNF SRTDADYIKK

1081 WKLYSYGNRI RIFRNPKKNN VEDWEEVCLT SAYKELENKY GINYQQGDIR ALLCEQSDKA

1141 FYSSFMALMS LMLQMRNSIT GRTDVDFLIS PVKNSDGIFY DSRNYEAQEN AILPKNADAN

1201 GAYNIARKVL WAIGQFKKAE DEKLDKVKIA ISNKEWLEYA QTSVKH

Mature LbCpf1 without 18 amino acid signal sequence:
                                                              (SEQ ID NO: 2)
MSKLEKFTNCYSLSKTLRFKAIPVGKTQENIDNKRLLVEDEKRAEDYKGVKKLL

DRYYLSFINDVLHSIKLKNLNNYISLFRKKTRTEKENKELENLEINLRKEIAKAFK

GNEGYKSLFKKDIIETILPEFLDDKDEIALVNSFNGFTTAFTGFFDNRENMFSEEA

KSTSIAFRCINENLTRYISNMDIFEKVDAIFDKHEVQEIKEKILNSDYDVEDFFEGE

FFNFVLTQEGIDVYNAIIGGFVTESGEKIKGLNEYINLYNQKTKQKLPKFKPLYKQ

VLSDRESLSFYGEGYTSDEEVLEVFRNTLNKNSEIFSSIKKLEKLFKNFDEYSSAG

IFVKNGPAISTISKDIFGEWNVIRDKWNAEYDDIHLKKKAVVTEKYEDDRRKSFK

KIGSFSLEQLQEYADADLSVVEKLKEIIIQKVDEIYKVYGSSEKLFDADFVLEKSL

KKNDAVVAIMKDLLDSVKSFENYIKAFFGEGKETNRDESFYGDFVLAYDILLKV

DHIYDAIRNYVTQKPYSKDKFKLYFQNPQFMGGWDKDKETDYRATILRYGSKY

YLAIMDKKYAKCLQKIDKDDVNGNYEKINYKLLPGPNKMLPKVFFSKKWMAY

YNPSEDIQKIYKNGTFKKGDMFNLNDCHKLIDFFKDSISRYPKWSNAYDFNFSET

EKYKDIAGFYREVEEQGYKVSFESASKKEVDKLVEEGKLYMFQIYNKDFSDKSH
```

-continued

```
GTPNLHTMYFKLLFDENNHGQIRLSGGAELFMRRASLKKEELVVHPANSPIANK

NPDNPKKTTTLSYDVYKDKRFSEDQYELHIPIAINKCPKNIFKINTEVRVLLKHD

DNPYVIGIDRGERNLLYIVVVDGKGNIVEQYSLNEIINNFNGIRIKTDYHSLLDKK

EKERFEARQNWTSIENIKELKAGYISQVVHKICELVEKYDAVIALEDLNSGFKNS

RVKVEKQVYQKFEKMLIDKLNYMVDKKSNPCATGGALKGYQITNKFESFKSMS

TQNGFIFYIPAWLTSKIDPSTGFVNLLKTKYTSIADSKKFISSFDRIMYVPEEDLFEF

ALDYKNFSRTDADYIKKWKLYSYGNRIRIFRNPKKNNVFDWEEVCLTSAYKELF

NKYGINYQQGDIRALLCEQSDKAFYSSFMALMSLMLQMRNSITGRTDVDFLISP

VKNSDGIFYDSRNYEAQENAILPKNADANGAYNIARKVLWAIGQFKKAEDEKL

DKVKIAISNKEWLEYAQTSVKH
```

The LbCpf1 variants described herein can include the amino acid sequence of SEQ ID NO:1, e.g., at least comprising amino acids 23-1246 of SEQ ID NO:1, with mutations (i.e., replacement of the native amino acid with a different amino acid, e.g., alanine, glycine, or serine), at one or more of the positions in Table A; amino acids 19-1246 of SEQ ID NO:1 are identical to amino acids 1-1228 of SEQ ID NO:2 (amino acids 1-1246 of SEQ ID NO:1 are referred to herein as LbCPF1 (+18)). In some embodiments, the LbCpf1 variants are at least 80%, e.g., at least 85%, 90%, or 95% identical to the amino acid sequence of SEQ ID NO:2, e.g., have differences at up to 5%, 10%, 15%, or 20% of the residues of SEQ ID NO:2 replaced, e.g., with conservative mutations, in addition to the mutations described herein. In preferred embodiments, the variant retains desired activity of the parent, e.g., the nuclease activity (except where the parent is a nickase or a dead Cpf1), and/or the ability to interact with a guide RNA and target DNA). The version of LbCpf1 used in the present working examples is SEQ ID NO:2, omitting the first 18 amino acids boxed above as described in Zetsche et al. Cell 163, 759-771 (2015).

In some embodiments, the Cpf1 variants also include one of the following mutations listed in Table A, which reduce or destroy the nuclease activity of the Cpf1 (i.e., render them catalytically inactive):

TABLE A

Residues involved in DNA and RNA catalysis

| | LbCpf1 (+18) | LbCpf1 |
|---|---|---|
| DNA targeting | D850 | D832 |
| | E853 | E835 |
| | N855 | N837 |
| | Y858 | Y840 |
| | E943 | E925 |
| | R1156 | R1138 |
| | S1158 | S1140 |
| | D1166 | D1148 |
| | D1198 | D1180 |
| RNA processing | H777 | H759 |
| | K786 | K768 |
| | K803 | K785 |
| | F807 | F789 |
| Mutations that turn Cpf1 into a nickase | | |
| | R1156A | R1138A |

See, e.g., Yamano et al., Cell. 2016 May 5; 165(4):949-62; Fonfara et al., Nature. 2016 Apr. 28; 532(7600):517-21; Dong et al., Nature. 2016 Apr. 28; 532(7600):522-6; and Zetsche et al., Cell. 2015 Oct. 22; 163(3):759-71. Note that "LbCpf1 (+18)" refers to the full sequence of amino acids 1-1246 of SEQ ID NO:1, while the LbCpf1 refers to the sequence of LbCpf1 in Zetsche et al., also shown herein as amino acids 1-1228 of SEQ ID NO:2 and amino acids 19-1246 of SEQ ID NO:1. Thus, in some embodiments, for LbCpf1 catalytic activity-destroying mutations are made at D832 and E925, e.g., D832A and E925A.

The Cpf1 variants, preferably comprising one or more nuclease-reducing or killing mutation, can be fused on the N or C terminus of the Cpf1 to a transcriptional activation domain (e.g., a transcriptional activation domain from the VP16 domain form herpes simplex virus (Sadowski et al., 1988, Nature, 335:563-564) or VP64; the p65 domain from the cellular transcription factor NF-kappaB (Ruben et al., 1991, Science, 251:1490-93); a tripartite effector fused to dCas9, composed of activators VP64, p65, and Rta (VPR) linked in tandem, Chavez et al., Nat Methods. 2015 April; 12(4):326-8); or the p300 HAT domain. p300/CBP is a histone acetyltransferase (HAT) whose function is critical for regulating gene expression in mammalian cells. The p300 HAT domain (1284-1673) is catalytically active and can be fused to nucleases for targeted epigenome editing. See Hilton et al., Nat Biotechnol. 2015 May; 33(5):510-7.

Any inducible protein dimerizing system can be used, e.g., based on the FK506-binding protein (FKBP), see, e.g., Rollins et al., Proc Natl Acad Sci USA. 2000 Jun. 20; 97(13): 7096-7101; the iDIMERIZE™ Inducible Heterodimer System from Clontech/Takara, wherein the proteins of interest are fused to the DmrA and DmrC binding domains respectively, and dimerization is induced by adding the A/C Heterodimerizer (AP21967). Others are also known, e.g., FKBP with CyP-Fas and FKCsA dimerizing agent (see Belshaw et al., Proceedings of the National Academy of Sciences of the United States of America. 93 (10): 4604-7 (1996)); FKBP and FRB domain of mTOR with Rapamycin dimerizing agent (Rivera et al., Nature Medicine. 2 (9): 1028-32 (1996)); GyrB domain with coumermycin dimerizing agent (Farrar et al., Nature. 383 (6596): 178-81 (1996)); gibberellin-induced dimerization (see Miyamoto et al., Nature Chemical Biology. 8 (5): 465-70 (2012); Miyamoto et al., Nature Chemical Biology. 8 (5): 465-70 (2012)); and protein heterodimerization system based on small molecules cross-linking fusion proteins derived from HaloTags and SNAP-tags (Erhart et al., Chemistry and Biology. 20 (4): 549-57 (2013).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plusrm, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

In some embodiments, the mutants have alanine in place of the wild type amino acid. In some embodiments, the mutants have any amino acid other than arginine or lysine (or the native amino acid).

Also provided herein are isolated nucleic acids encoding the Cpf1 fusion proteins, vectors comprising the isolated nucleic acids, optionally operably linked to one or more regulatory domains for expressing the variant proteins, and host cells, e.g., mammalian host cells, comprising the nucleic acids, and optionally expressing the variant proteins.

The fusion proteins described herein can be used for altering the genome of a cell; the methods generally include expressing the variant proteins in the cells, along with a guide RNA having a region complementary to a selected portion of the genome of the cell. Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922; US20150056629; US20150044772; US20150024500; US20150024499; US20150020223; US20140356867; US20140295557; US20140273235; US20140273226; US20140273037; US20140189896; US20140113376; US20140093941; US20130330778; US20130288251; US20120088676; US20110300538; US20110236530; US20110217739; US20110002889; US20100076057; US20110189776; US20110223638; US20130130248; US20150050699; US20150071899; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753; WO/2008/108989; WO/2010/054108; WO/2012/164565; WO/2013/098244; WO/2013/176772; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

The fusion proteins described herein can be used in place of or in addition to any of the Cas9 or Cpf1 proteins described in the foregoing references, or in combination with analogous mutations described therein, with a guide RNA appropriate for the selected Cpf1, i.e., with guide RNAs that target selected sequences.

In addition, the fusion proteins described herein can be used in place of the wild-type Cas9, Cpf1 or other Cas9 or Cpf1 mutations (such as the dCpf1 or Cpf1 nickase) as known in the art, e.g., a fusion protein with a heterologous functional domain as described in U.S. Pat. No. 8,993,233; US 20140186958; U.S. Pat. No. 9,023,649; WO/2014/099744; WO 2014/089290; WO2014/144592; WO144288;

WO2014/204578; WO2014/152432; WO2115/099850; U.S. Pat. No. 8,697,359; US2010/0076057; US2011/0189776; US2011/0223638; US2013/0130248; WO/2008/108989; WO/2010/054108; WO/2012/164565; WO/2013/098244; WO/2013/176772; US20150050699; US 20150071899 and WO 2014/124284.

In some embodiments, the fusion proteins include a linker between the Cpf1 variant and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:3) or GGGGS (SEQ ID NO:4), e.g., two, three, four, or more repeats of the GGGS (SEQ ID NO:3) or GGGGS (SEQ ID NO:4) unit. Other linker sequences can also be used.

In some embodiments, the variant protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton FL 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLoS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140). See also Ramsey and Flynn, Pharmacol Ther. 2015 Jul. 22. pii: S0163-7258(15)00141-2.

Alternatively or in addition, the variant proteins can include a nuclear localization sequence, e.g., SV40 large T antigen NLS (PKKKRRV (SEQ ID NO:5)) and nucleoplasmin NLS (KRPAATKKAGQAKKKK (SEQ ID NO:6)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the variants include a moiety that has a high affinity for a ligand, for example GST, FLAG or hexahistidine sequences. Such affinity tags can facilitate the purification of recombinant variant proteins.

For methods in which the variant proteins are delivered to cells, the proteins can be produced using any method known in the art, e.g., by in vitro translation, or expression in a suitable host cell from nucleic acid encoding the variant protein; a number of methods are known in the art for producing proteins. For example, the proteins can be produced in and purified from yeast, E. coli, insect cell lines, plants, transgenic animals, or cultured mammalian cells; see, e.g., Palomares et al., "Production of Recombinant Proteins: Challenges and Solutions," Methods Mol Biol. 2004; 267: 15-52. In addition, the variant proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1):180-194.

Expression Systems

To use the Cpf1 fusion proteins described herein, it may be desirable to express them from a nucleic acid that encodes them. This can be performed in a variety of ways. For example, the nucleic acid encoding the Cpf1 fusion proteins can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the Cpf1 fusion proteins for production of the Cpf1 fusion proteins. The nucleic acid encoding the Cpf1 fusion proteins can also be cloned into an expression vector, for administration to a plant cell, animal cell, preferably a mammalian cell or a human cell, fungal cell, bacterial cell, or protozoan cell.

To obtain expression, a sequence encoding a Cpf1 fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the Cpf1 fusion protein is to be administered in vivo for gene regulation, either a constitutive or an inducible promoter can be used, depending on the particular use of the Cpf1 fusion protein. In addition, a preferred promoter for administration of the Cpf1 fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the Cpf1 fusion proteins, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the Cpf1 fusion proteins, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the Cpf1 fusion proteins can include RNA Pol III promoters to drive expression of the guide RNAs, e.g., the H1, U6 or 7SK promoters. These human promoters allow for expression of Cpf1 fusion proteins in mammalian cells following plasmid transfection.

In some embodiments, a single nucleic acid encoding a plurality of Cpf1 gRNAs is used, e. g., as follows

```
                                          (SEQ ID NO: 7)
GAGGGCCTATTTCCCATGATTCCTTCATATTTGCATATACGA

TACAAGGCTGTTAGAGAGATAATTAGAATTAATTTGACTGTA

AACACAAAGATATTAGTACAAAATACGTGACGTAGAAAGTAA

TAATTTCTTGGGTAGTTTGCAGTTTTAAAATTATGTTTTAAA

ATGGACTATCATATGCTTACCGTAACTTGAAAGTATTTCGAT

TTCTTGGCTTTATATATCTTGTGGAAAGGACGAAACACCGAA

TTTCTACTAAGTGTAGAT[spacer_sequence_1]

AATTTCTACTAAGTGTAGAT[spacer_sequence_2]

AATTTCTACTAAGTGTAGAT[spacer_sequence_3]

AATTTCTACTAAGTGTAGATTTTTTTT
```
The hU6 promoter is shown in bold above.

The Lb crRNA direct repeats are AATTTCTACTAAGTGTAGAT (SEQ ID NO: 38, shown in italics above. The spacer sequences of 17-20 nts (preferably 20) that direct the Cpf1 to the target gene are indicated as spacer sequence_1, 2, or 3.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the Cpf1 variant.

The present invention also includes the vectors and cells comprising the vectors, and cells and transgenic animals expressing the fusion proteins.

EXAMPLES

The invention is further described in the following examples, which do not limit the scope of the invention described in the claims.

Methods

The following materials and methods were used in the Examples below.

Plasmids and oligonucleotides.

A list of plasmids, and related sequences used in this study are found in the Sequences section, below; LbCpf1 crRNA information is in Table 1.

TABLE 1

Single Cpf1 crRNAs

| Name | Spacer Sequence with Cpf1 PAM | SEQ ID NO | Genomic coordinates |
|---|---|---|---|
| HBB_P_1 guide | TTTGTACTGATGG TATGGGCCAA | 39 | Chr11: 5248505-5248528 |
| HBB_P_2 guide | TTTGAAGTCCAAC TCCTAAGCCAG | 40 | Chr11: 5248452-5248475 |
| HBB_P_3 guide | TTTGCAAGTGTAT TTACGTAATAT | 41 | Chr11: 5248550-5248573 |
| AR_P_1 guide | TTTGAGAGTCTGG ATGAGAAATGC | 42 | ChrX: 66763209-66763232 |
| AR_P_2 guide | TTTCTACCCTCTT CTCTGCCTTTC | 43 | ChrX: 66763260-66763283 |
| AR_P_3 guide | TTTGCTCTAGGAA CCCTCAGCCCC | 44 | ChrX: 66763299-66763322 |
| NPY1R_P_1 guide | TTTCAAGCCTCGG GAAACTGCCCT | 45 | Chr4: 164254005-164254028 |
| NPY1R_P_2 guide | TTTCTTTGTTTGC AGGTCAGTGCC | 46 | Chr4: 164254048-164254071 |
| NPY1R_P_3 guide | TTTGGGCTGGCGC TCGAGCTCTCC | 47 | Chr4: 164254099-164254122 | dLbCpf1-p65 and dLbCpf1-VPR plasmids (JG1202 and JG1211, respectively) were constructed by cloning p65 and VPR into dLbCpf1 (MMW1578) using BstZ17I and Not I sites through Gibson assembly. VPR was amplified from SP-dCas9-VPR which was a gift from George Church (Addgene plasmid #63798)[46]. dLbCpf1-DmrA(×1) to dLbCpf1-DmrA(×4) (JG674, JG676, JG693, and YET1000, respectively) were generated by inserting dLbCpf1 into AgeI and XhoI digested constructs that have different numbers of DmrA domains (BPK1019, BPK1033, BPK1140, BPK1179 for dCas9-DmrA(×4) to dCas9-DmrA(×4), respectively) using Gibson cloning method. A previously described plasmid encoding DmrC was digested with NruI and p65 or VPR with G4S-linker were added via Gibson assembly for DmrC-P65 (BPK1169) and DmrC-VPR (MMW948). For constructing single crRNA plasmids, oligonucleotide pairs for crRNA spacers were annealed and ligated into BsmBI-digested LbCpf1 crRNA backbone plasmid, BPK3082 (Addgene #78742)[14]. For the cloning of multiplexed crRNAs used in this study, three pairs of oligonucleotides were designed to have overhangs. Each oligonucleotides pair was annealed in the presence of T4 PNK, and all three oligo pairs are ligated to BsmBI and HindIII-digested LbCpf1 crRNA backbone plasmid, BPK3082 in one reaction. Sequences for all oligo pairs are listed in Tables 2A-B.

TABLE 2A

Multiplexed Cpf1 crRNAs targeting a single promoter

| Name | Pair # | Oligonucleotides sequences to be ordered | Orientation | SEQ ID NO: |
|---|---|---|---|---|
| HBB Multiplexed | Pair1 | AGATTACTGATGGTATGGGCCAAA | Top | 8 |
| | | TAGTAGAAATTTTGGCCCCATACC ATCAGTA | Bottom | 9 |
| | Pair 2 | ATTTCTACTAAGTGTAGATAAGTCC AACTCCTAAGCCAGAATTTCTACT AA | Top | 10 |
| | | ATCTACACTTAGTAGAAATTCTGGC TTAGGAGTTGGACTTATCTACACT | Bottom | 11 |
| | Pair 3 | GTGTAGATCAAGTGTATTTACGTAA TATAATTTCTACTAAGTGTAGATTT TTTTTA | Top | 12 |
| | | AGCTTAAAAAAATCTACACTTAG TAGAAATTATATTACGTAAATACA CTTG | Bottom | 13 |
| AR_ Multiplexed | Pair1 | AGATAGAGTCTGGATGAGAAATGCA | Top | 14 |
| | | TAGTAGAAATTGCATTTCTCATCCA GACTCT | Bottom | 15 |
| | Pair 2 | ATTTCTACTAAGTGTAGATTACCCT CTTCTCTGCCTTTCAATTTCTACTAA | Top | 16 |
| | | ATCTACACTTAGTAGAAATTGAAAG GCAGAGAAGAGGGTAATCTACACT | Bottom | 17 |
| | Pair 3 | GTGTAGATCTCTAGGAACCCTCAGC CCCAATTTCTACTAAGTGTAGATTT TTTTTA | Top | 18 |
| | | AGCTTAAAAAAATCTACACTTAGT AGAAATTGGGGCTGAGGGTTCCTAG AG | Bottom | 19 |
| NPY1R Multiplexed | Pair1 | AGATAAGCCTCGGGAAACTGCCCTA | Top | 20 |
| | | TAGTAGAAATTAGGGCAGTTTCCC GAGGCTT | Bottom | 21 |
| | Pair 2 | ATTTCTACTAAGTGTAGATTTTGTT TGCAGGTCAGTGCCAATTTCTACTAA | Top | 22 |
| | | ATCTACACTTAGTAGAAATTGGCAC TGACCTGCAAACAAAATCTACACT | Bottom | 23 |
| | Pair 3 | GTGTAGATGGCTGGCGCTCGAGCTC TCCAATTTCTACTAAGTGTAGATTT TTTTTA | Top | 24 |
| | | AGCTTAAAAAAATCTACACTTAG TAGAAATTGGAGAGCTCGAGCGCCA GCC | Bottom | 25 |

TABLE 2B

Multiplexed Cpf1 crRNAs targeting multiple promoters

| Name | Pair # | Oligonucleotides sequences to be ordered | Orientation | SEQ ID NO: |
|---|---|---|---|---|
| HBB_AR NPY1R Multiplexed | Pair 1 | AGATTACTGATGGTAT GGGGCCAAA | Top | 26 |
| | | TAGTAGAAATTTTGGC CCCATACCATCAGTA | Bottom | 27 |
| | Pair 2 | ATTTCTACTAAGTGTA GATCTCTAGGAACCCT CAGCCCCAATTTCTAC TAA | Top | 28 |
| | | ATCTACACTTAGTAGAA ATTGGGGCTGAGGGTTC CTAGAGATCTACACT | Bottom | 29 |
| | Pair 3 | GTGTAGATAAGCCTCGG GAAACTGCCCTAATTTC TACTAAGTGTAGATTTT TTTTA | Top | 30 |
| | | AGCTTAAAAAAAATCTA CACTTAGTAGAAATTAG GGCAGTTTCCCGAGGC TT | Bottom | 31 |

Human Cell Culture and Transfection.

HEK293 cells were grown at 37°, in 5% CO2 in Dulbecco's Modified Eagle Medium (DMEM) with 10% fetal bovine serum and 1% penicillin and streptomycin. 750 ng of dLbCpf1-p65/VPR with 250 ng of LbCpf1 crRNAs were co-transfected using a 3 ul of TransIT®-LT1 Transfection Reagent (Mirus, cat #MIR2300) into HEK293 cells in a 12-well plate. 400 ng of dLbCpf1 fused with different numbers of DmrA, 200 ng of DmrC-p65/VPR, and 400 ng of LbCpf1 crRNAs were co-transfected using 3 ul of LT-1 into HEK293 cells in a 12-well plate.

Reverse Transcription Quantitative PCR.

Total RNA was extracted from the transfected cells 72 hours post-transfection using the NucleoSpin® RNA Plus (Clontech, cat #740984.250), and 250 ng of purified RNA was used for cDNA synthesis using High-Capacity RNA-cDNA kit (ThermoFisher, cat #4387406). cDNA was diluted 1:20 and 3 ul of cDNA was used for quantitative PCR (qPCR). qPCR reaction samples were prepared using cDNA, SYBR (ThermoFisher, cat #4385612), and primers detecting each target transcript. Primer sequences are listed in Table 3. qPCR was performed using Roche LightCycler480. When Ct values are over 35, we considered them as 35, because Ct values fluctuate for very low expressed transcripts. Samples that were transfected with LbCpf1 crRNA backbone plasmid, BPK3082 were used as negative controls, and the levels of fold activation over negative controls were normalized to the expression of HPRT1.

TABLE 3

RT-qPCR primers

| Primer name | Sequence | SEQ ID NO: | Orientation | Target Gene |
|---|---|---|---|---|
| oET_173 | ATGGTGAGCAGAGTGCCCTATC | 32 | F | NPY1R |
| oET_174 | ATGGTCCCTGGCAGTCTCCAAA | 33 | R | |
| oET_175 | CCATCGGACTCTCATAGGTTGTC | 34 | F | AR |
| oET_176 | GACCTGTACTTATTGTCTCT-CATC | 35 | R | |
| oET_225 | GCACGTGGATCCTGAGAACT | 36 | F | HBB |
| oET_226 | ATTGGACAGCAAGAAAGCGAG | 37 | R | |

F, Forward; R, Reverse

Figure 1B:
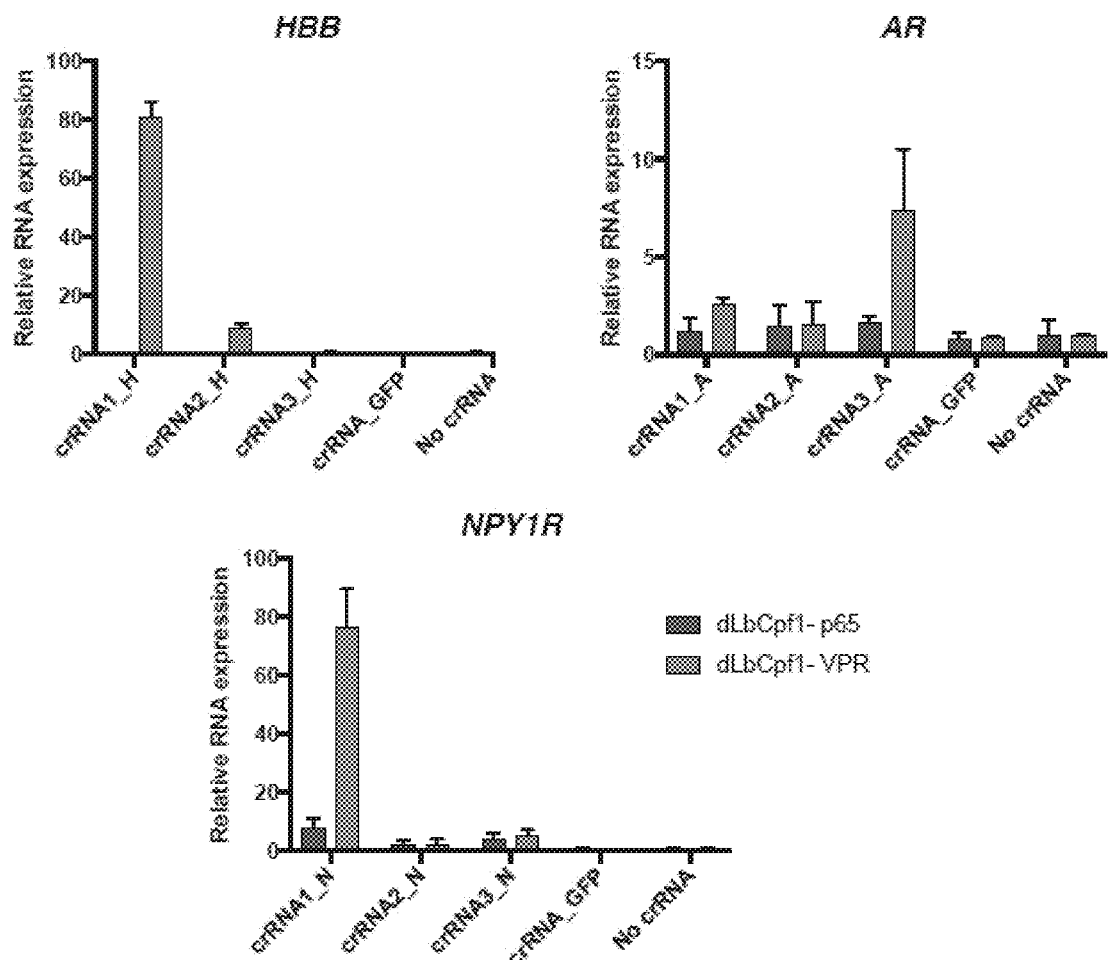

Example 1. Targeted Human Endogenous Gene Regulation Using Individual crRNAs with dLbCpf1-Based Activators In initial experiments, we tested whether direct fusions of a catalytically inactive Cpf1 nuclease to transcriptional activation domains (FIG. 1A) could activate endogenous human gene promoters. We targeted the promoters of three different endogenous genes that are not expressed in human HEK293 cells (HBB, AR, and NPY1R) by designing three crRNAs for each promoter (See Tables 2A-B). We used a catalytically inactive nuclease-dead version of Cpf1 from Lachnospiraceae bacterium ND2006 (dLbCpf1) because we and others have shown this has higher nuclease activities compared to the other Cpf1 nuclease reported to be active in human cells (AsCpf1 from Acidaminococcus sp. BV3L6)[14,36,44]. dLbCpf1 fusions to a single human NF-KB p65 activation domain tested with the nine individual crRNAs either failed to increase or only weakly increased transcription from the three human gene target promoters (FIG. 1B), consistent with previously published results with single activation domain fusions to dSpCas9[46]. By contrast, dLbCpf1 fusions to the synthetic multimerized VPR activator (consisting of four copies of the viral-based VP16 activator, the human NF-KB p65 activation domain, and the Epstein-Barr virus R transactivator Rta) could significantly activate transcription with at least one crRNA for each of the three target genes (FIG. 1B). This result is similar to previous experiments with dSpCas9 activators, which demonstrated the need to recruit multiple transcriptional activation domains to achieve efficient upregulation of target gene promoter activity[46,47].

Figure 1C:
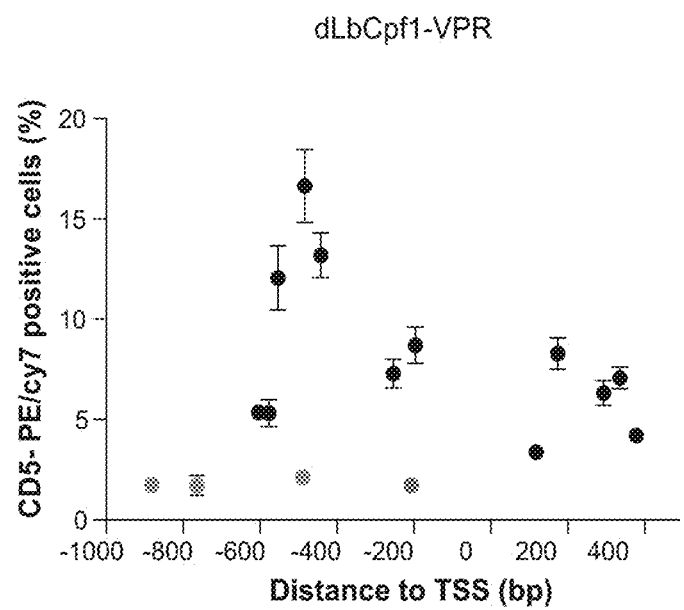
Figure 1C:
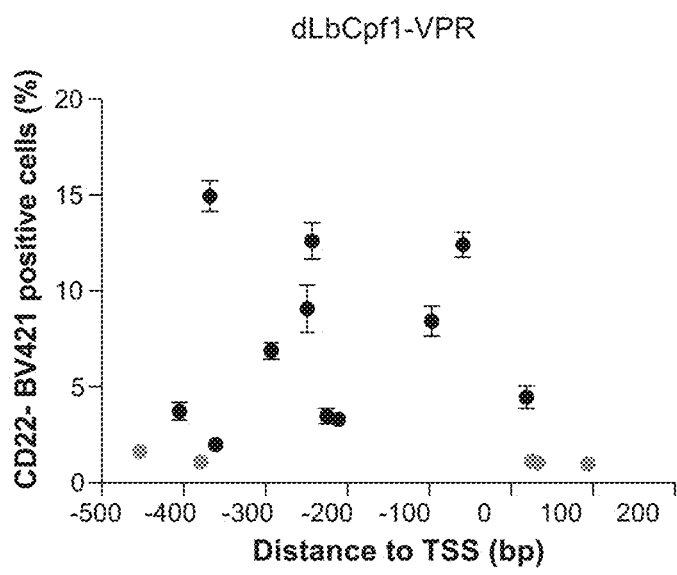

We also tested a larger series of 32 crRNAs positioned within 1 kb upstream or 500 bp downstream of the TSSs of two additional endogenous genes, CD5 and CD22, which encode cell surface proteins. Most of the 32 crRNAs tested could significantly activate the target gene promoter when positioned between −600 bp upstream and ~400 bp downstream of the TSSs (FIG. 1C), consistent with results obtained using dSpCas9 activators[3]. The levels of activation observed with dLbCpf1-based activators are comparable to what might be observed in naturally occurring biological systems and are similar to what has been reported previously for analogous dCas9-based activators[5].

Figure 1D:
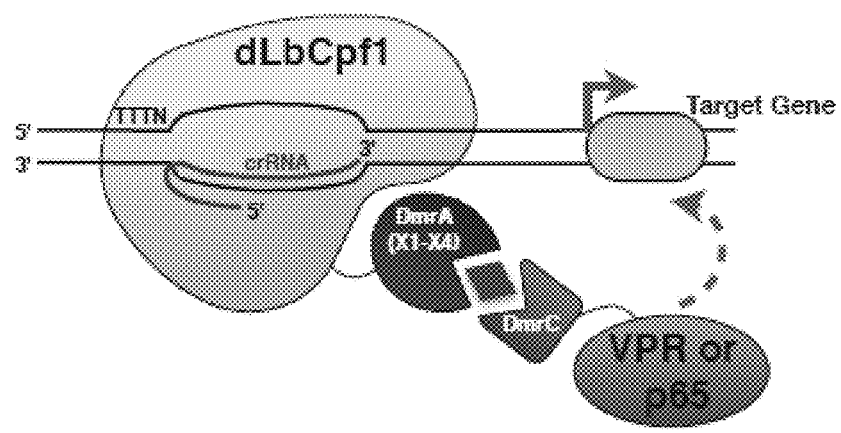
Figure 1E:
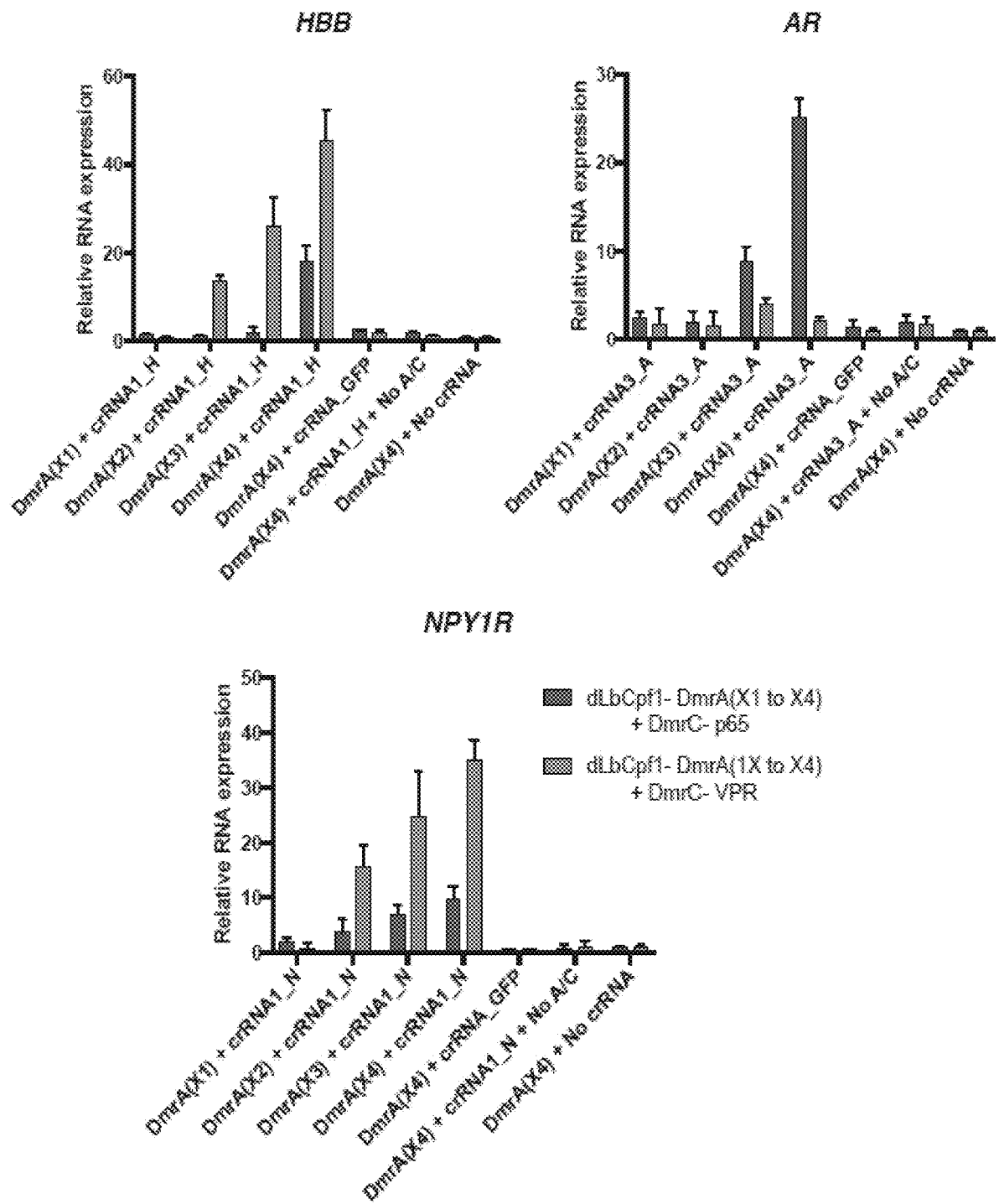

We next sought to develop chemically inducible, bi-partite dLbCpf1-based transcriptional activators. We envisioned using a dimerization system of fragments of the FK506-binding protein (FKBP) and FKBP-rapamycin-binding protein (FRB) known as the DmrA and DmrC domains, respectively, that interact only in the presence of a rapamycin analog known as the A/C heterodimerizer[41], to split dLbCpf1 activators into two parts that would assemble only in the presence of the A/C drug (FIG. 1D). dLbCpf1 fused to a single DmrA domain together with a DmrC domain fused to either NF-KB p65 or VPR failed to activate transcription of the HBB, AR, or NPY1R genes with any of the single crRNAs that had worked efficiently at these promoters with the direct dLbCpf1 activator fusions (FIG. 1E). Reasoning that increasing the number of DmrA domains linked to dLbCpf1 might increase the efficiency of gene activation, we constructed fusions harboring two, three or four DmrA domains. Testing of these fusions with DmrC-VPR with single crRNAs revealed activation at two of the three endogenous gene promoters (HBB and NPY1R; FIG. 1E), with increasing effects observed with more DmrA domains and with maximum levels reaching approximately half of that observed with direct dLbCpf1-VPR fusions. This maximal level of activation was dependent on the presence of the A/C heterodimerizer drug (FIG. 1E), demonstrating that this system is drug-inducible.

Surprisingly, these dLbCpf1 fusions together with DmrC-p65 could robustly activate transcription from all three target gene promoters using single crRNAs (FIG. 1E), an unexpected finding given the lack of activation observed with direct dLbCpf1-p65 fusions with the same crRNAs (FIG. 1B). For the AR promoter, DmrC-p65 could activate transcription by ~25-fold compared with the lack of an effect by DmrC-VPR. For the HBB and NPY1R promoters, the levels of activation observed with DmrC-p65 were somewhat less (~50% and ~30%, respectively) than those obtained with DmrC-VPR but still robust in absolute terms (~20-fold and ~10-fold activation). Maximal activation with DmrC-p65 fusions was again dependent on the presence of A/C heterodimerizer drug. Taken together, these findings demonstrate that p65 can provide an important alternative to VPR for the drug-inducible dLbCpf1 activator platform.

Figure 2A:
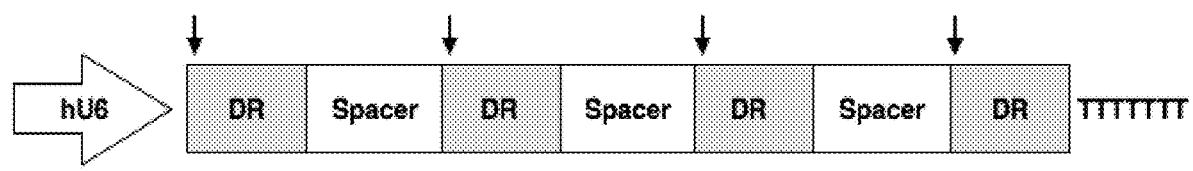
Figure 2B:
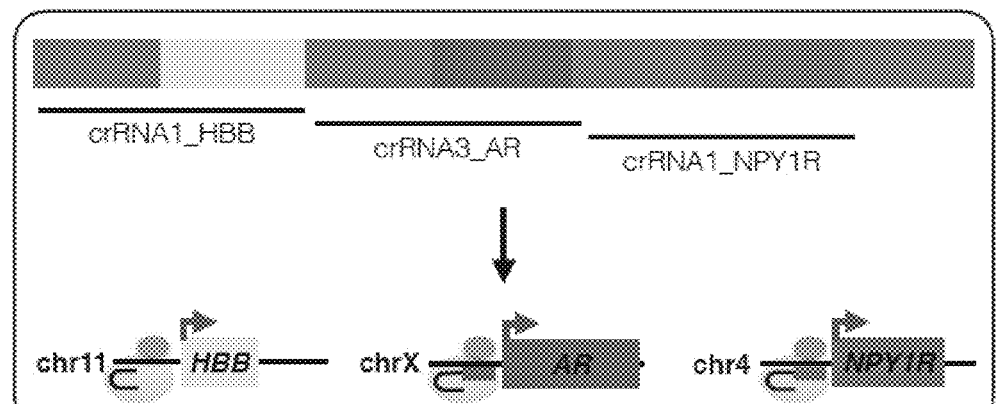
Figure 2C:
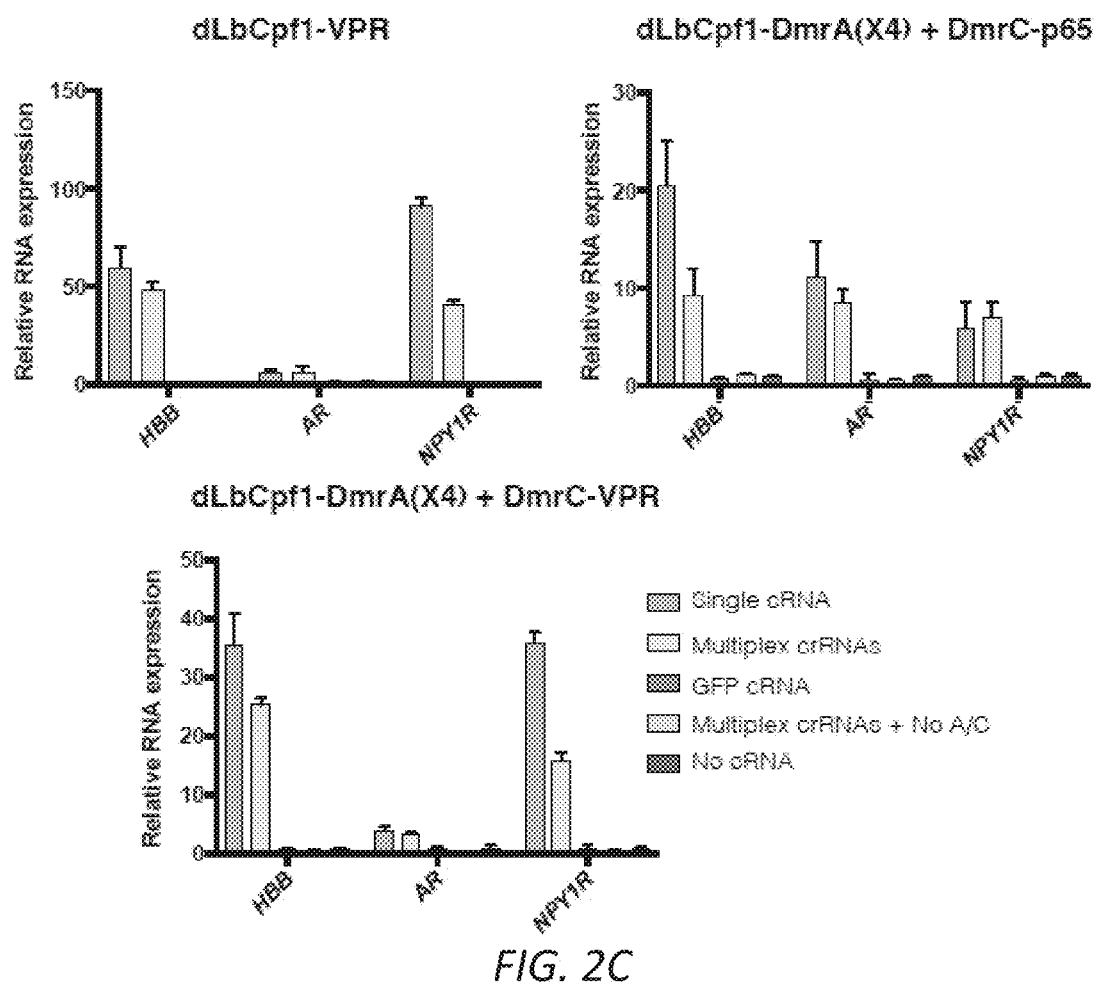

Example 2. Multiplex and Synergistic Regulation of Endogenous Human Genes by dLbCpf1-Based Activators A major advantage of Cpf1 nuclease relative to Cas9 nuclease is the ability to more easily express more than one guide RNA for multiplex applications. Previous work has shown that multiple crRNAs encoded in a single transcript driven by a U6 promoter can be processed into individual crRNAs by Cpf1 itself (FIG. 2A), enabling multiplex induction of mutagenic genome editing events[49]. We tested whether we could use dLbCpf1-based systems to activate three different endogenous human genes using three crRNAs, each already shown to be active with a dLbCpf1-based activator and all encoded on a single transcript (FIG. 2B). Testing of these multiplex crRNA transcripts revealed that these could be used together with dLbCpf1-VPR direct fusions, with dLbCpf1-DmrA(x4) and DmrC-VPR fusions, and with dLbCpf1-DmrA(x4) and DmrC-p65 fusions to mediate transcriptional activation of multiple endogenous gene promoters in human HEK293 cells (FIG. 2C). The magnitudes of activation observed with the multiplex crRNAs were somewhat lower (~18 to 55%) than those observed with expression of a single crRNA. One possible explanation for this difference might be greater competition for binding to dLbCpf1 fusion proteins due to the presumably three-fold higher levels of crRNA present in cells expressing the multiplex transcript. Nonetheless, these results demonstrate that as many as three crRNAs encoded in a larger multiplex transcript can be used to activate transcription of multiple gene targets using dLbCpf1-based activators.

Figure 2D:
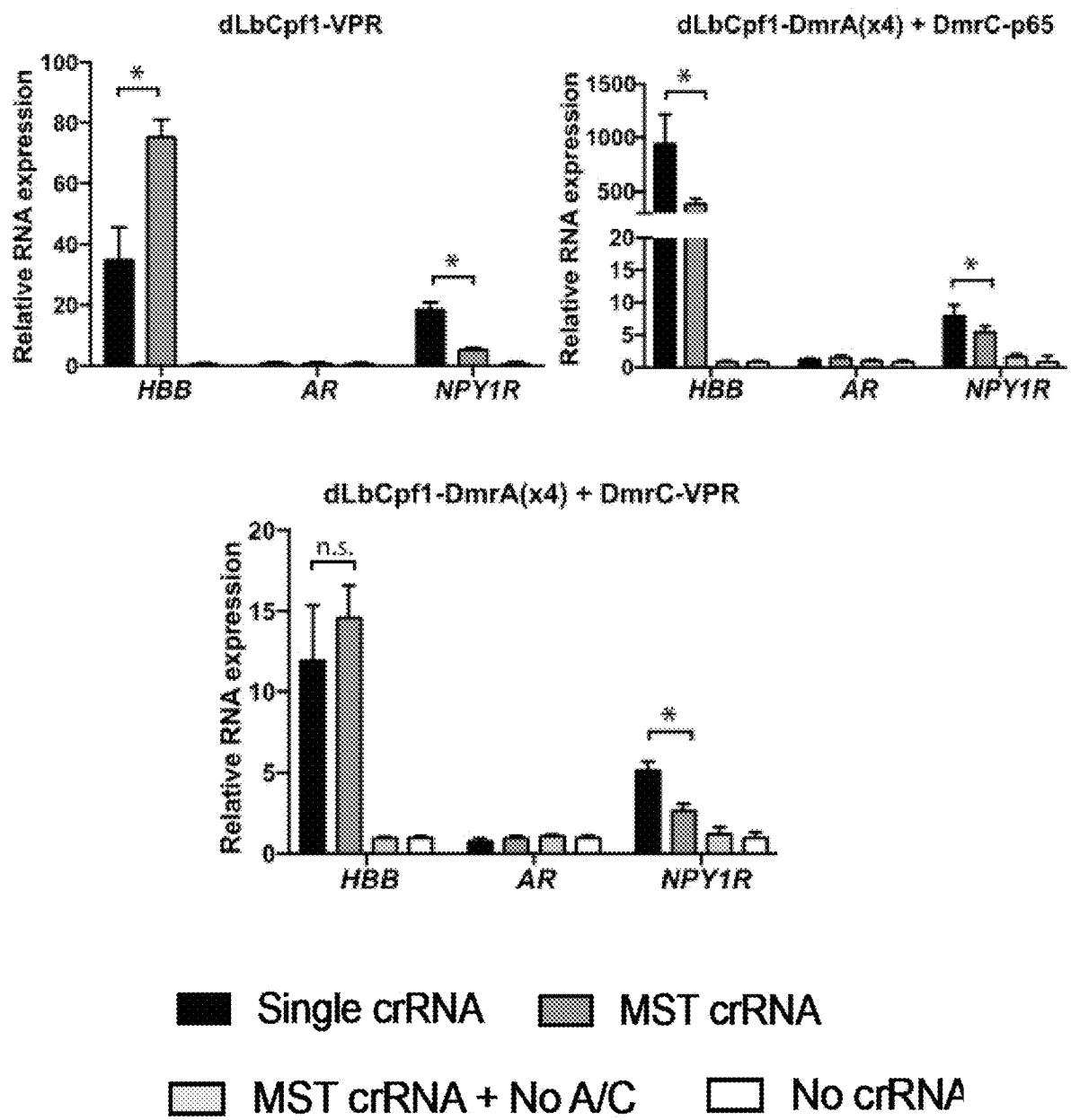
Figure 2E:
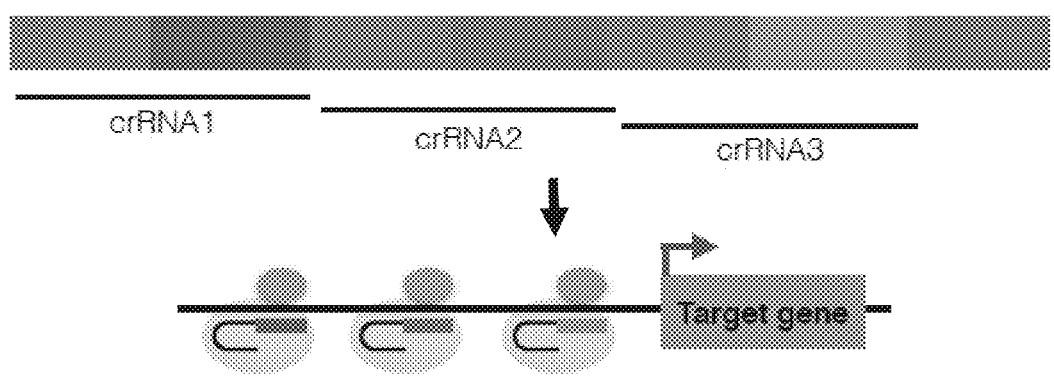

To extend our findings to another human cell line, we also tested the direct VPR activator fusions and drug-regulated VPR and p65 activators in human U2OS cells, targeting the same genes (HBB, AR, and NPY1R) with MST crRNAs and single crRNAs (FIG. 2D). We observed that HBB and NPY1R were highly upregulated and that HBB activation with DmrC-p65 was even greater than in HEK293s. We did not observe activation of the AR gene but this is likely because its baseline expression is already highly elevated in U2OS cells (with a basal quantitative RT-PCR Ct value of ~28). Relative differences in the efficacies of crRNAs expressed singly or in MSTs were similar to what we observed in HEK293s.

Figure 2F:
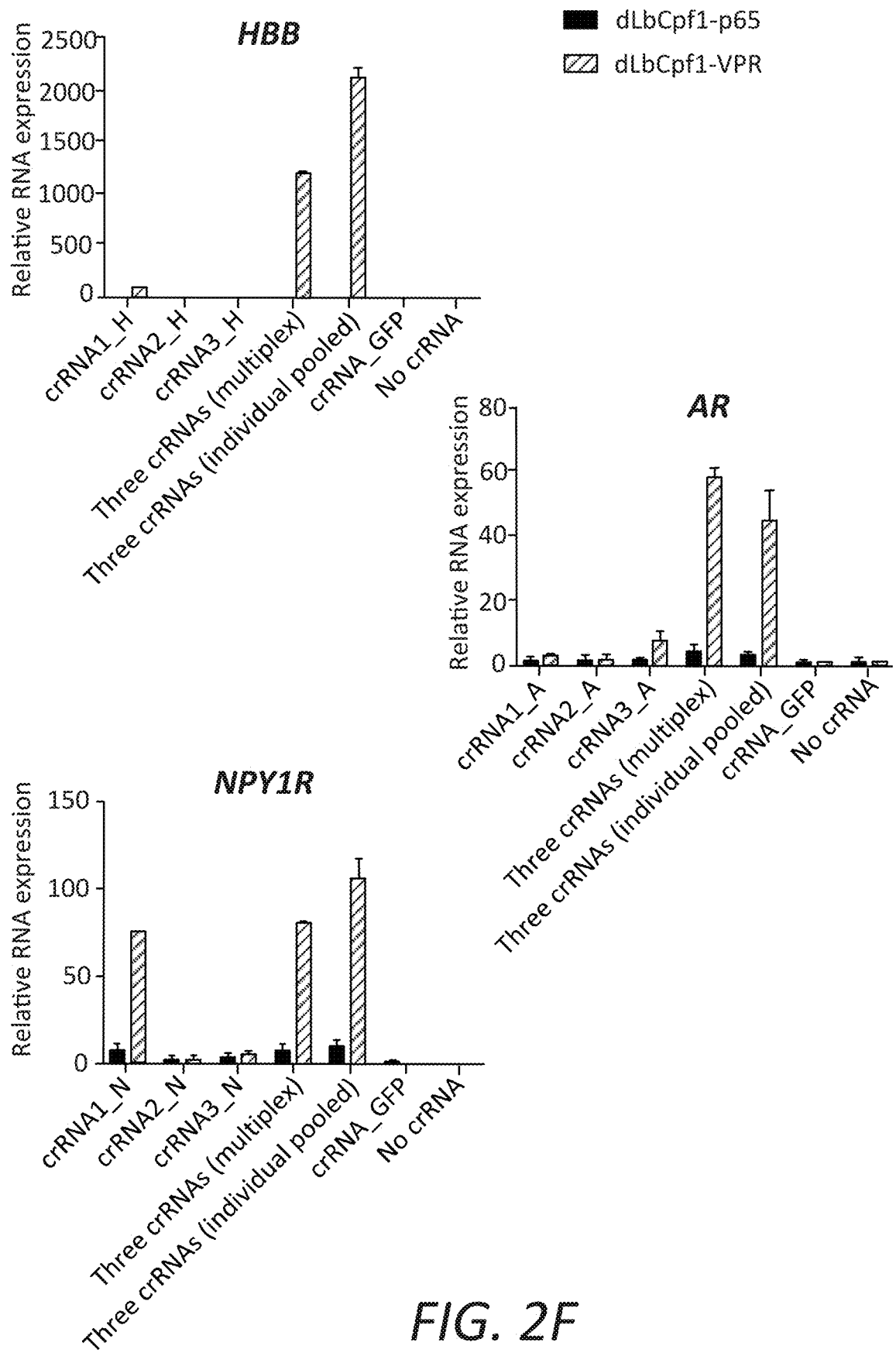
Figure 2G:
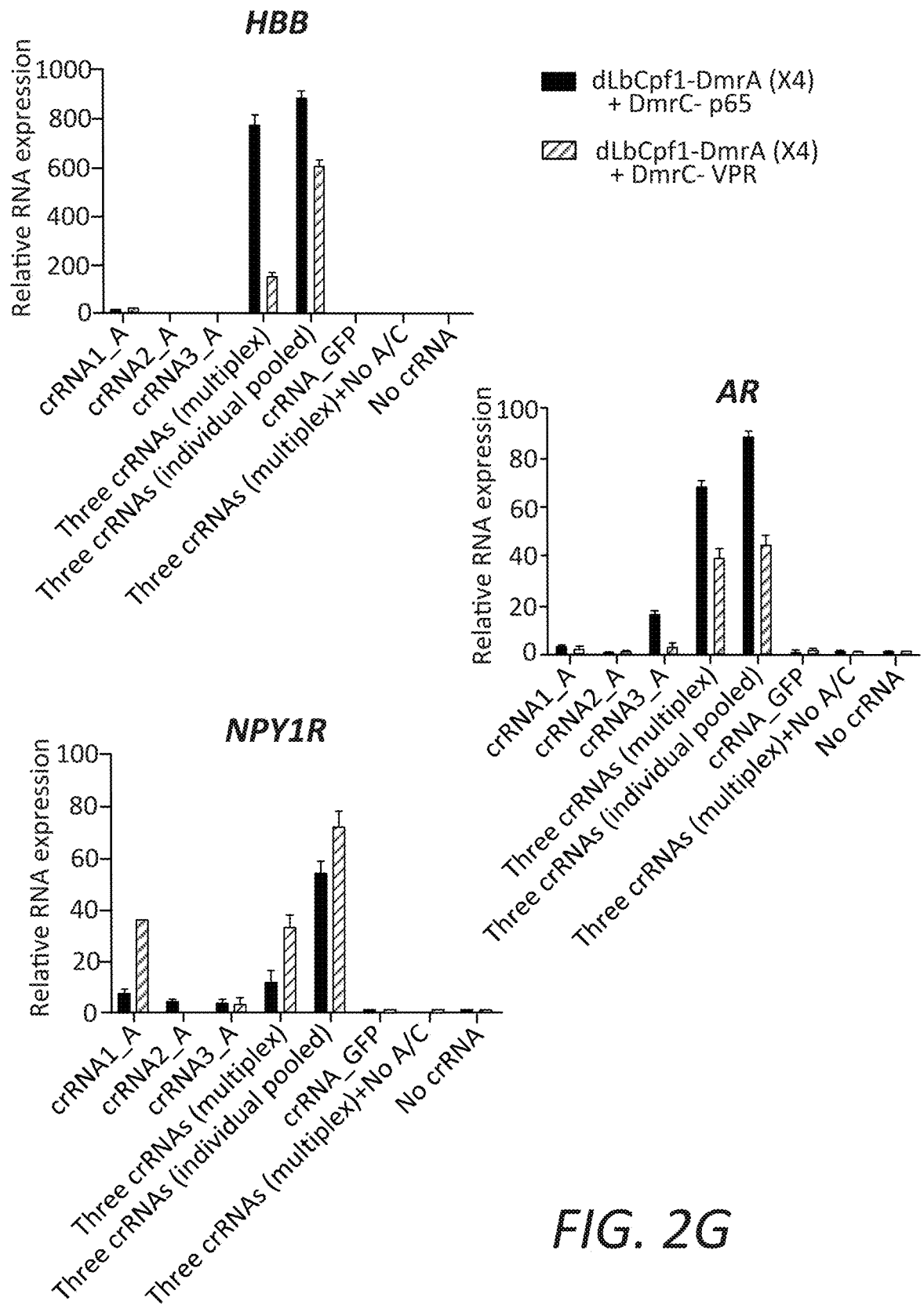
Figure 2H:
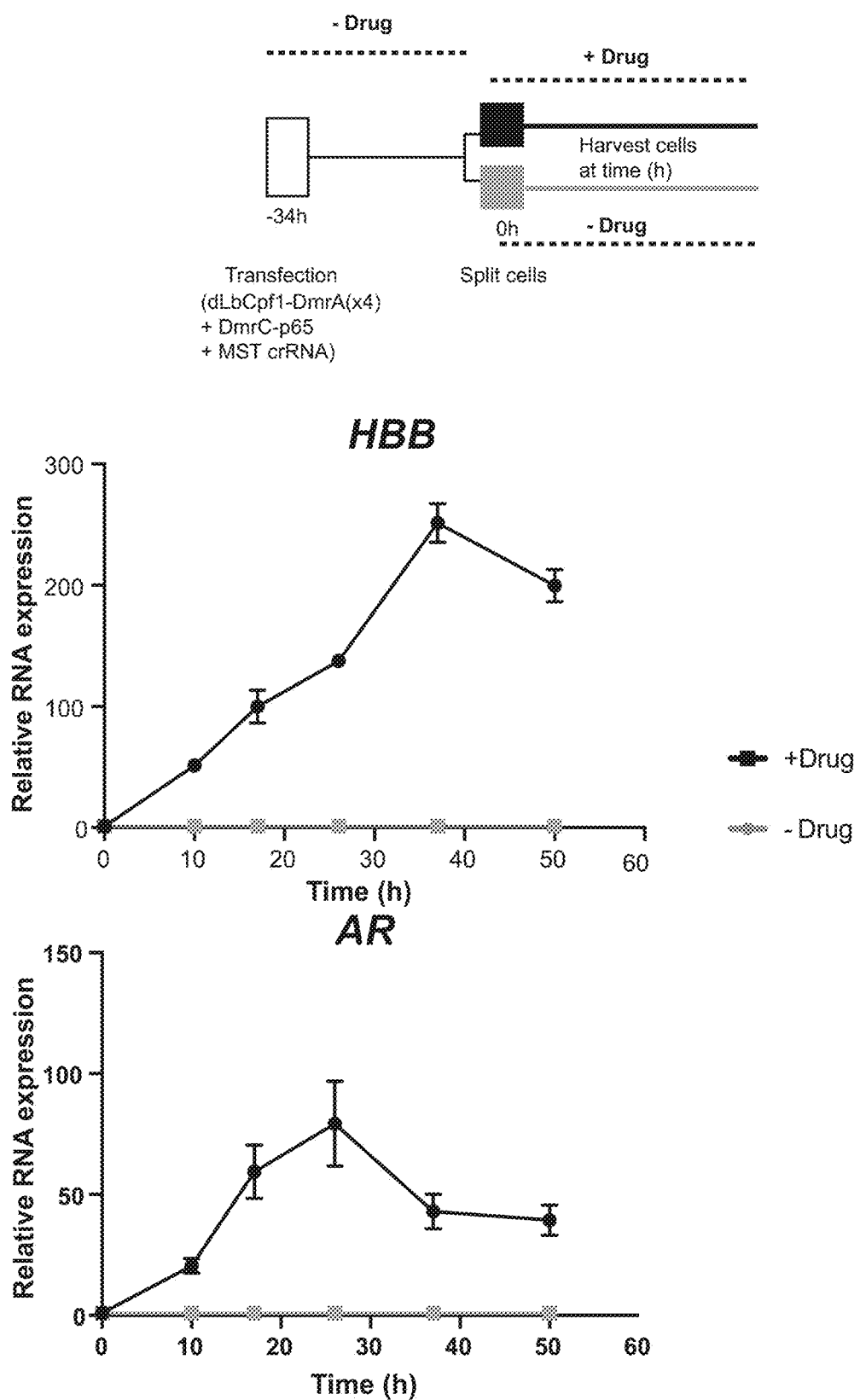

We also sought to determine whether multiple crRNAs expressed from a single construct are actually active in the same cell. Because our experiments were performed on populations of cells with transient transfection of expression vectors, it is formally possible that the multiplex gene activation we observed above was due to different crRNAs being active in different cells within the population of transfected cells. To rule out this possibility, we reasoned that if multiple crRNAs designed against sites within the same gene promoter are expressed from the same transcript within a single cell, this should lead to synergistic increases in transcription from the target gene promoter (FIG. 2E) (synergistic activation is defined as greater than additive effects or two or more activators acting on the same promoter[2]). With direct fusions of VPR to dLbCpf1, we observed synergistic activation using three crRNAs expressed in a single transcript for two of the three endogenous gene promoters we examined (HBB and AR; FIG. 2F). For the third gene promoter (NPY1R), we did not observe synergistic activation with the three crRNAs when expressed from the same transcript but did see synergy in a control experiment when they were expressed as separate RNAs introduced simultaneously (FIG. 2F). We also did not observe synergistic activation with direct fusions of p65 to dLbCpf1 at any of the three genes with three crRNAs expressed either from the same transcript or from separate transcripts (FIG. 2F). With the drug-inducible dLbCpf1 and VPR activator system, we again observed synergy at the HBB and AR promoters but only with the transcripts expressed separately at the NPY1R promoter (FIG. 2G). A similar pattern of results was observed with the drug-inducible LbCpf1 and p65 system (FIG. 2G). Importantly, the synergistic activation levels observed with the p65 activation domain on the HBB and AR genes were again higher than comparable experiments performed with the VPR activator (FIG. 2G). Taken together, we conclude that multiple active crRNAs can be expressed from a single transcript in the same cell, albeit with somewhat lower activity than if they are expressed from multiple separate expression vectors.

Figure 2I:
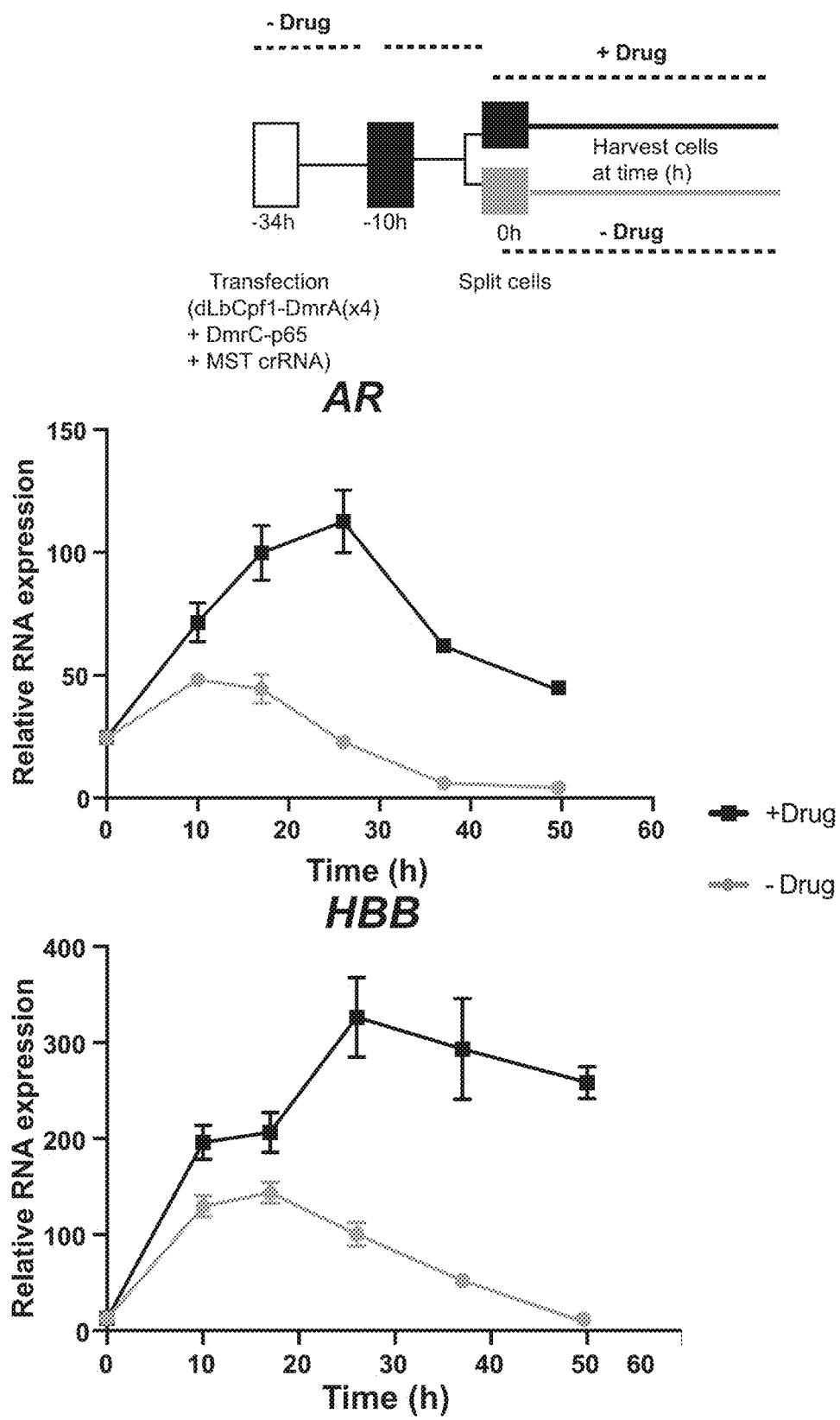

In addition, we assessed the kinetics of activator effects to the addition and withdrawal of A/C heterodimerizer. We found that maximum activation of the HBB and AR genes was observed ~25 to 35 hours after the addition of drug (FIG. 2H) and return of activated gene expression to baseline occurred ~35 to 45 hours after withdrawal of the drug (FIG. 2I). We envision that drug-inducibility could be easily extended to other orthologues and we have successfully used these same strategies to regulate and tune dSpCas9-based activators

Sequences

| Name | Addgene # | Description |
|---|---|---|
| MMW1578 | 104563 | CAG-human dLbCpf1(D832A)-NLS-3xHA |
| BPK1169 | | CAG-DmrC-NLS-FLAG-P65 |
| MMW948 | 104565 | CAG-DmrC-NLS-FLAG-VPR |
| JG1202 | | CAG-human dLbCpf1(D832A)-NLS-3xHA-P65 |
| JG1211 | 104567 | CAG-human dLbCpf1(D832A)-NLS-3xHA-VPR |
| JG674 | 104568 | CAG-human dLbCpf1(D832A)-NLS-3xHA-DmrA(X1) |
| JG676 | 104569 | CAG-human dLbCpf1(D832A)-NLS-3xHA-DmrA(X2) |
| JG693 | 104570 | CAG-human dLbCpf1(D832A)-NLS-3xHA-DmrA(X3) |
| YET1000 | 104571 | CAG-human dLbCpf1(D832A)-NLS-3xHA-DmrA(X4) |
| BPK3082 | 78742 | U6-LbCpf1-crRNA-BsmBIcassette |

1.
MMW1578: CAG-human dLbCpf1(D832A)-NLS-3xHA
Human codon optimized dLbCpf1: bold,
NLS: italic, 3xHA: lower case
(SEQ ID NO: 48)
ATGAGCAAGCTGGAGAAGTTTACAAAACTGCTACTCCCTGT

CTAAGACCCTGAGGTTCAAGGCCATCCCTGTGGGCAAGAC

CCAGGAGAACATCGACAATAAGCGGCTGCTGGTGGAGGAC

GAGAAGAGAGCCGAGGATTATAAGGGCGTGAAGAAGCTGC

TGGATCGCTACTATCTGTCTTTTATCAACGACGTGCTGCA

CAGCATCAAGCTGAAGAATCTGAACAATTACATCAGCCTG

TTCCGGAAGAAAACCAGAACCGAGAAGGAGAATAAGGAGC

TGGAGAACCTGGAGATCAATCTGCGGAAGGAGATCGCCAA

GGCCTTCAAGGGCAACGAGGGCTACAAGTCCCTGTTTAAG

AAGGATATCATCGAGACAATCCTGCCAGAGTTCCTGGACG

ATAAGGACGAGATCGCCCTGGTGAACAGCTTCAATGGCTT

TACCACAGCCTTCACCGGCTTCTTTGATAACAGAGAGAAT

ATGTTTTCCGAGGAGGCCAAGAGCACATCCATCGCCTTCA

GGTGTATCAACGAGAATCTGACCCGCTACATCTCTAATAT

GGACATCTTCGAGAAGGTGGACGCCATCTTTGATAAGCAC

GAGGTGCAGGAGATCAAGGAGAAGATCCTGAACAGCGACT

ATGATGTGGAGGATTTCTTTGAGGGCGAGTTCTTTAACTT

TGTGCTGACACAGGAGGGCATCGACGTGTATAACGCCATC

ATCGGCGGCTTCGTGACCGAGAGCGGCGAGAAGATCAAGG

GCCTGAACGAGTACATCAACCTGTATAATCAGAAAACCAA

GCAGAAGCTGCCTAAGTTTAAGCCACTGTATAAGCAGGTG

CTGAGCGATCGGGAGTCTCTGAGCTTCTACGGCGAGGGCT

ATACATCCGATGAGGAGGTGCTGGAGGTGTTTAGAAACAC

CCTGAACAAGAACAGCGAGATCTTCAGCTCCATCAAGAAG

CTGGAGAAGCTGTTCAAGAATTTTGACGAGTACTCTAGCG

CCGGCATCTTTGTGAAGAACGGCCCCGCCATCAGCACAAT

CTCCAAGGATATCTTCGGCGAGTGGAACGTGATCCGGGAC

AAGTGGAATGCCGAGTATGACGATATCCACCTGAAGAAGA

AGGCCGTGGTGACCGAGAAGTACGAGGACGATCGGAGAAA

-continued

GTCCTTCAAGAAGATCGGCTCCTTTTCTCTGGAGCAGCTG

CAGGAGTACGCCGACGCCGATCTGTCTGTGGTGGAGAAGC

TGAAGGAGATCATCATCCAGAAGGTGGATGAGATCTACAA

GGTGTATGGCTCCTCTGAGAAGCTGTTCGACGCCGATTTT

GTGCTGGAGAAGAGCCTGAAGAAGAACGACGCCGTGGTGG

CCATCATGAAGGACCTGCTGGATTCTGTGAAGAGCTTCGA

GAATTACATCAAGGCCTTCTTTGGCGAGGGCAAGGAGACA

AACAGGGACGAGTCCTTCTATGGCGATTTTGTGCTGGCCT

ACGACATCCTGCTGAAGGTGGACCACATCTACGATGCCAT

CCGCAATTATGTGACCCAGAAGCCCTACTCTAAGGATAAG

TTCAAGCTGTATTTTCAGAACCCTCAGTTCATGGGCGGCT

GGGACAAGGATAAGGAGACAGACTATCGGGCCACCATCCT

GAGATACGGCTCCAAGTACTATCTGGCCATCATGGATAAG

AAGTACGCCAAGTGCCTGCAGAAGATCGACAAGGACGATG

TGAACGGCAATTACGAGAAGATCAACTATAAGCTGCTGCC

CGGCCCTAATAAGATGCTGCCAAAGGTGTTCTTTTCTAAG

AAGTGGATGGCCTACTATAACCCCAGCGAGGACATCCAGA

AGATCTACAAGAATGGCACATTCAAGAAGGGCGATATGTT

TAACCTGAATGACTGTCACAAGCTGATCGACTTCTTTAAG

GATAGCATCTCCCGGTATCCAAAGTGGTCCAATGCCTACG

ATTTCAACTTTTCTGAGACAGAGAAGTATAAGGACATCGC

CGGCTTTTACAGAGAGGTGGAGGAGCAGGGCTATAAGGTG

AGCTTCGAGTCTGCCAGCAAGAAGGAGGTGGATAAGCTGG

TGGAGGAGGGCAAGCTGTATATGTTCCAGATCTATAACAA

GGACTTTTCCGATAAGTCTCACGGCACACCCAATCTGCAC

ACCATGTACTTCAAGCTGCTGTTTGACGAGAACAATCACG

GACAGATCAGGCTGAGCGGAGGAGCAGAGCTGTTCATGAG

GCGCGCCTCCCTGAAGAAGGAGGAGCTGGTGGTGCACCCA

GCCAACTCCCCTATCGCCAACAAGAATCCAGATAATCCCA

AGAAAACCACAACCCTGTCCTACGACGTGTATAAGGATAA

GAGGTTTTCTGAGGACCAGTACGAGCTGCACATCCCAATC

GCCATCAATAAGTGCCCCAAGAACATCTTCAAGATCAATA

CAGAGGTGCGCGTGCTGCTGAAGCACGACGATAACCCCTA

TGTGATCGGCATCGCCAGGGGCGAGCGCAATCTGCTGTAT

ATCGTGGTGGTGGACGGCAAGGGCAACATCGTGGAGCAGT

ATTCCCTGAACGAGATCATCAACAACTTCAACGGCATCAG

GATCAAGACAGATTACCACTCTCTGCTGGACAAGAAGGAG

AAGGAGAGGTTCGAGGCCCGCCAGAACTGGACCTCCATCG

AGAATATCAAGGAGCTGAAGGCCGGCTATATCTCTCAGGT

GGTGCACAAGATCTGCGAGCTGGTGGAGAAGTACGATGCC

GTGATCGCCCTGGAGGACCTGAACTCTGGCTTTAAGAATA

GCCGCGTGAAGGTGGAGAAGCAGGTGTATCAGAAGTTCGA

GAAGATGCTGATCGATAAGCTGAACTACATGGTGGACAAG

AAGTCTAATCCTTGTGCAACAGGCGGCGCCCTGAAGGGCT

ATCAGATCACCAATAAGTTCGAGAGCTTTAAGTCCATGTC

TACCCAGAACGGCTTCATCTTTTACATCCCTGCCTGGCTG

ACATCCAAGATCGATCCATCTACCGGCTTTGTGAACCTGC

TGAAAACCAAGTATACCAGCATCGCCGATTCCAAGAAGTT

CATCAGCTCCTTTGACAGGATCATGTACGTGCCCGAGGAG

GATCTGTTCGAGTTTGCCCTGGACTATAAGAACTTCTCTC

GCACAGACGCCGATTACATCAAGAAGTGGAAGCTGTACTC

CTACGGCAACCGGATCAGAATCTTCCGGAATCCTAAGAAG

AACAACGTGTTCGACTGGGAGGAGGTGTGCCTGACCAGCG

CCTATAAGGAGCTGTTCAACAAGTACGGCATCAATTATCA

GCAGGGCGATATCAGAGCCCTGCTGTGCGAGCAGTCCGAC

AAGGCCTTCTACTCTAGCTTTATGGCCCTGATGAGCCTGA

TGCTGCAGATGCGGAACAGCATCACAGGCCGCACCGACGT

GGATTTTCTGATCAGCCCTGTGAAGAACTCCGACGGCATC

TTCTACGATAGCCGGAACTATGAGGCCCAGGAGAATGCCA

TCCTGCCAAAGAACGCCGACGCCAATGGCGCCTATAACAT

CGCCAGAAAGGTGCTGTGGGCCATCGGCCAGTTCAAGAAG

GCCGAGGACGAGAAGCTGGATAAGGTGAAGATCGCCATCT

CTAACAAGGAGTGGCTGGAGTACGCCCAGACCAGCGTGAA

GCAC*AAAAGGCCGGCGGCCACGAAAAAGGCCGGCCAGGCA*

*AAAAGAAAAAGGGATCC*tacccatacgatgttccagatt acgcttatccctacgacgtgcctgattatgcatacccata tgatgtccccgactatgccTAA 2. BPK1169: CAG-DmrC-NLS-FLAG-P65
DmrC: bold, NLS-Flag: italic,
P65: lower case
(SEQ ID NO: 50)

ATGGGATCCAGAATCCTCTGGCATGAGATGTGGCATGAAG

GCCTGGAAGAGGCATCTCGTTTGTACTTTGGGGAAAGGAA

CGTGAAAGGCATGTTTGAGGTGCTGGAGCCCTTGCATGCT

ATGATGGAACGGGGACCCCAGACTCTGAAGGAAACATCCT

TTAATCAGGCCTATGGTCGAGATTTAATGGAGGCCCAAGA

GTGGTGCAGGAAGTACATGAAATCAGGGAATGTCAAGGAC

CTCCTCCAAGCCTGGGACCTCTATTATCATGTGTTCCGAC

GAATCTCAAGGGCGGCGGATCCCCCAAGAAGAAGAGGAA

*AGTCTCGAGCGACTACAAAGACCATGACGGTGATTATAAA*

*GATCATGACATCGATTACAAGGATGACGATGACAAGGCTG*

CAGGAGGCGGTGGAAGCGGAtggagttccagtacctgcc agatacagacgatcgtcaccggattgaggagaaacgtaaa aggacatatgagacctttcaagagcatcatgaagaagagtc ctttcagcggacccaccgaccccggcctccacctcgacg cattgctgtgccttcccgcagctcagcttctgtccccaag ccagcaccccagccctatcccttt acgtcatccctgagca ccatcaactatgatgagtttcccaccatggtgtttccttc tgggcagatcagccaggcctcggccttggcccggcccct ccccaagtcctgcccaggctccagcccctgccctgctc cagccatggtatcagctctggcccaggcccagcccctgt cccagtcctagcccaggccctcctcaggctgtggcccca cctgccccaagcccacccaggctggggaaggaacgctgt cagaggccctgctgcagctgcagtttgatgatgaagacct ggggggccttgcttggcaacagcacagacccagctgtgttc acagacctggcatccgtcgataactccgagtttcagcagc tgctgaaccagggcataccctgtggccccccacacaactga gcccatgctgatggagtaccctgaggctataactcgccta gtgacaggggcccagaggcccccgacccagctcctgctc cactgggggcccggggctccccaatggcctcctttcagg agatgaagacttctcctccattgcggacatggacttctca gccctgctgagtcagatcagctctTAA 3. MMW948: CAG-DmrC-NLS-FLAG-VPR
DmrC: bold, NLS-Flag: italic,
VPR: lowercase
(SEQ ID NO: 49)

ATGGGATCCAGA

ATCCTCTGGCATGAGATGTGGCATGAAGGCCTGGAAGAGG

CATCTCGTTTGTACTTTGGGGAAAGGAACGTGAAAGGCAT

GTTTGAGGTGCTGGAGCCCTTGCATGCTATGATGGAACGG

-continued

GGACCCCAGACTCTGAAGGAAACATCCTTTAATCAGGCCT

ATGGTCGAGATTTAATGGAGGCCCAAGAGTGGTGCAGGAA

GTACATGAAATCAGGGAATGTCAAGGACCTCCTCCAAGCC

TGGGACCTCTATTATCATGTGTTCCGACGAATCTCAAAGG

GGGGGGATCCCCCAAGAAGAAGAGGAAAGTCTCGAGCGAC

*TACAAAGACCATGACGGTGATTATAAAGATCATGACATCG*

*ATTACAAGGATGACGATGACAAGGCTGCAGGAGGCGGTGG*

*AAGCGGGTCG*gaggccagcggttccggacgggctgacgca ttggacgattttgatctggatatgctgggaagtgacgccc tcgatgattttgaccttgacatgcttggttcggatgccct tgatgactttgacctcgacatgctcggcagtgacgccctt gatgatttcgacctggacatgctgattaactctagaagtt ccggatctccgaaaagaaacgcaaagttggtagccagta cctgcccgacaccgacgaccggcaccggatcgaggaaaag cggaagcggacctacgagacattcaagagcatcatgaaga agtccccttcagcggccccaccgaccctagacctccacc tagaagaatcgccgtgcccagcagatccagcgccagcgtg ccaaaacctgccccccagccttacccttcaccagcagcc tgagcaccatcaactacgacgagttccctaccatggtgtt cccagcggccagatctctcaggcctctgctctggctcca gcccctcctcaggtgctgcctcaggctcctgctcctgcac cagctccagccatggtgtctgcactggctcaggcaccagc acccgtgcctgtgctggcctcctgacctccacaggctgtg gctccaccagcccctaaacctacacaggccggcgagggca cactgtctgaagctctgctgcagctgcagttcgacgacga ggatctgggagccctgctgggaaacagcaccgatcctgcc gtgttcaccgacctggccagcgtggacaacagcgagttcc agcagctgctgaaccagggcatccctgtggcccctcacac caccgagcccatgctgatggaataccccgaggccatcacc cggctcgtgacaggcgctcagaggcctcctgatccagctc ctgcccctctgggagcaccaggcctgcctaatggactgct gtctggcgacgaggacttcagctctatcgccgatatggat ttctcagccttgctgggctctggcagcggcagccgggatt ccagggaagggatgtttttgccgaagcctgaggccggctc cgctattagtgacgtgtttgaggccgcgaggtgtgccag ccaaaacgaatccggccatttcatcctccaggaagtccat gggccaaccgccactccccgccagcctcgcaccaacacc aaccggtccagtacatgagccagtcgggtcactgaccccg gcaccagtccctcagccactggatccagcgcccgcagtga ctcccgaggccagtcacctgttggaggatccgatgaaga gacgagccaggctgtcaaagcccttcgggagatggccgat -continued actgtgattccccagaaggaagaggctgcaatctgtggcc aaatggacctttcccatccgcccccaagggggccatctgga tgagctgacaaccacacttgagtccatgaccgaggatctg aacctggactcacccctgaccccggaattgaacgagattc tggataccttcctgaacgacgagtgcctcttgcatgccat gcatatcagcacaggactgtccatcttcgacacatctctg

TTT

4.
JG1202: CAG-human dLbCpf1(D832A)-NLS-3xHA-P65
Human codon optimized dLbCpf1: bold,
NLS: italic, 3xHA: lower case,
P65: lower case and bold
(SEQ ID NO: 51)

ATGAGCAAGCTGGAGAAGTTTACAAACTGCTACTCCCTGT

CTAAGACCCTGAGGTTCAAGGCCATCCCTGTGGGCAAGAC

CCAGGAGAACATCGACAATAAGCGGCTGCTGGTGGAGGAC

GAGAAGAGAGCCGAGGATTATAAGGGCGTGAAGAAGCTGC

TGGATCGCTACTATCTGTCTTTTATCAACGACGTGCTGCA

CAGCATCAAGCTGAAGAATCTGAACAATTACATCAGCCTG

TTCCGGAAGAAAACCAGAACCGAGAAGGAGAATAAGGAGC

TGGAGAACCTGGAGATCAATCTGCGGAAGGAGATCGCCAA

GGCCTTCAAGGGCAACGAGGGCTACAAGTCCCTGTTTAAG

AAGGATATCATCGAGACAATCCTGCCAGAGTTCCTGGACG

ATAAGGACGAGATCGCCCTGGTGAACAGCTTCAATGGCTT

TACCACAGCCTTCACCGGCTTCTTTGATAACAGAGAGAAT

ATGTTTTCCGAGGAGGCCAAGAGCACATCCATCGCCTTCA

GGTGTATCAACGAGAATCTGACCCGCTACATCTCTAATAT

GGACATCTTCGAGAAGGTGGACGCCATCTTTGATAAGCAC

GAGGTGCAGGAGATCAAGGAGAAGATCCTGAACAGCGACT

ATGATGTGGAGGATTTCTTTGAGGGCGAGTTCTTTAACTT

TGTGCTGACACAGGAGGGCATCGACGTGTATAACGCCATC

ATCGGCGGCTTCGTGACCGAGAGCGGCGAGAAGATCAAGG

GCCTGAACGAGTACATCAACCTGTATAATCAGAAAACCAA

GCAGAAGCTGCCTAAGTTTAAGCCACTGTATAAGCAGGTG

CTGAGCGATCGGGAGTCTCTGAGCTTCTACGGCGAGGGCT

ATACATCCGATGAGGAGGTGCTGGAGGTGTTTAGAAACAC

CCTGAACAAGAACAGCGAGATCTTCAGCTCCATCAAGAAG

CTGGAGAAGCTGTTCAAGAATTTTGACGAGTACTCTAGCG

CCGGCATCTTTGTGAAGAACGGCCCCGCCATCAGCACAAT

CTCCAAGGATATCTTCGGCGAGTGGAACGTGATCCGGGAC

AAGTGGAATGCCGAGTATGACGATATCCACCTGAAGAAGA

AGGCCGTGGTGACCGAGAAGTACGAGGACGATCGGAGAAA

GTCCTTCAAGAAGATCGGCTCCTTTTCTCTGGAGCAGCTG

-continued

CAGGAGTACGCCGACGCCGATCTGTCTGTGGTGGAGAAGC
TGAAGGAGATCATCATCCAGAAGGTGGATGAGATCTACAA
GGTGTATGGCTCCTCTGAGAAGCTGTTCGACGCCGATTTT
GTGCTGGAGAAGAGCCTGAAGAAGAACGACGCCGTGGTGG
CCATCATGAAGGACCTGCTGGATTCTGTGAAGAGCTTCGA
GAATTACATCAAGGCCTTCTTTGGCGAGGGCAAGGAGACA
AACAGGGACGAGTCCTTCTATGGCGATTTTGTGCTGGCCT
ACGACATCCTGCTGAAGGTGGACCACATCTACGATGCCAT
CCGCAATTATGTGACCCAGAAGCCCTACTCTAAGGATAAG
TTCAAGCTGTATTTTCAGAACCCTCAGTTCATGGGCGGCT
GGGACAAGGATAAGGAGACAGACTATCGGGCCACCATCCT
GAGATACGGCTCCAAGTACTATCTGGCCATCATGGATAAG
AAGTACGCCAAGTGCCTGCAGAAGATCGACAAGGACGATG
TGAACGGCAATTACGAGAAGATCAACTATAAGCTGCTGCC
CGGCCCTAATAAGATGCTGCCAAAGGTGTTCTTTTCTAAG
AAGTGGATGGCCTACTATAACCCCAGCGAGGACATCCAGA
AGATCTACAAGAATGGCACATTCAAGAAGGGCGATATGTT
TAACCTGAATGACTGTCACAAGCTGATCGACTTCTTTAAG
GATAGCATCTCCCGGTATCCAAAGTGGTCCAATGCCTACG
ATTTCAACTTTTCTGAGACAGAGAAGTATAAGGACATCGC
CGGCTTTTACAGAGAGGTGGAGGAGCAGGGCTATAAGGTG
AGCTTCGAGTCTGCCAGCAAGAAGGAGGTGGATAAGCTGG
TGGAGGAGGGCAAGCTGTATATGTTCCAGATCTATAACAA
GGACTTTTCCGATAAGTCTCACGGCACACCCAATCTGCAC
ACCATGTACTTCAAGCTGCTGTTTGACGAGAACAATCACG
GACAGATCAGGCTGAGCGGAGGAGCAGAGCTGTTCATGAG
GCGCGCCTCCCTGAAGAAGGAGGAGCTGGTGGTGCACCCA
GCCAACTCCCCTATCGCCAACAAGAATCCAGATAATCCCA
AGAAAACCACAACCCTGTCCTACGACGTGTATAAGGATAA
GAGGTTTTCTGAGGACCAGTACGAGCTGCACATCCCAATC
GCCATCAATAAGTGCCCCAAGAACATCTTCAAGATCAATA
CAGAGGTGCGCGTGCTGCTGAAGCACGACGATAACCCCTA
TGTGATCGGCATCGCCAGGGGCGAGCGCAATCTGCTGTAT
ATCGTGGTGGTGGACGGCAAGGGCAACATCGTGGAGCAGT
ATTCCCTGAACGAGATCATCAACAACTTCAACGGCATCAG
GATCAAGACAGATTACCACTCTCTGCTGGACAAGAAGGAG
AAGGAGAGGTTCGAGGCCCGCCAGAACTGGACCTCCATCG
AGAATATCAAGGAGCTGAAGGCCGGCTATATCTCTCAGGT
GGTGCACAAGATCTGCGAGCTGGTGGAGAAGTACGATGCC
GTGATCGCCCTGGAGGACCTGAACTCTGGCTTTAAGAATA
GCCGCGTGAAGGTGGAGAAGCAGGTGTATCAGAAGTTCGA

-continued

GAAGATGCTGATCGATAAGCTGAACTACATGGTGGACAAG
AAGTCTAATCCTTGTGCAACAGGCGGCGCCCTGAAGGGCT
ATCAGATCACCAATAAGTTCGAGAGCTTTAAGTCCATGTC
TACCCAGAACGGCTTCATCTTTTACATCCCTGCCTGGCTG
ACATCCAAGATCGATCCATCTACCGGCTTTGTGAACCTGC
TGAAAACCAAGTATACCAGCATCGCCGATTCCAAGAAGTT
CATCAGCTCCTTTGACAGGATCATGTACGTGCCCGAGGAG
GATCTGTTCGAGTTTGCCCTGGACTATAAGAACTTCTCTC
GCACAGACGCCGATTACATCAAGAAGTGGAAGCTGTACTC
CTACGGCAACCGGATCAGAATCTTCCGGAATCCTAAGAAG
AACAACGTGTTCGACTGGGAGGAGGTGTGCCTGACCAGCG
CCTATAAGGAGCTGTTCAACAAGTACGGCATCAATTATCA
GCAGGGCGATATCAGAGCCCTGCTGTGCGAGCAGTCCGAC
AAGGCCTTCTACTCTAGCTTTATGGCCCTGATGAGCCTGA
TGCTGCAGATGCGGAACAGCATCACAGGCCGCACCGACGT
GGATTTTCTGATCAGCCCTGTGAAGAACTCCGACGGCATC
TTCTACGATAGCCGGAACTATGAGGCCCAGGAGAATGCCA
TCCTGCCAAAGAACGCCGACGCCAATGGCGCCTATAACAT
CGCCAGAAAGGTGCTGTGGGCCATCGGCCAGTTCAAGAAG
GCCGAGGACGAGAAGCTGGATAAGGTGAAGATCGCCATCT
CTAACAAGGAGTGGCTGGAGTACGCCCAGACCAGCGTGAA
GCAC*AAAAGGCCGGCGGCCACGAAAAAGGCCGGCCAGGCA*
*AAAAAGAAAAAGGGATCC*tacccatacgatgttccagatt
acgcttatccctacgacgtgcctgattatgcatacccata
tgatgtccccgactatgccGGAAGCatggagttccagtac
ctgccagatacagacgatcgtcaccggattgaggagaaac
gtaaaaggacatatgagaccttcaagagcatcatgaagaa
gagtcctttcagcggacccaccgaccccggcctccacct
cgacgcattgctgtgccttcccgcagctcagcttctgtcc
ccaagccagcacccagccctatccctttacgtcatccct
gagcaccatcaactatgatgagtttccaccatggtgttt
ccttctgggcagatcagccaggcctcggccttggcccgg
cccctccccaagtcctgcccaggctccagccctgcccc
tgctccagccatggtatcagctctggcccaggccccagcc
cctgtcccagtcctagcccaggccctcctcaggctgtgg
ccccacctgcccccaagcccacccaggctggggaaggaac
gctgtcagaggccctgctgcagctgcagtttgatgatgaa
gacctgggggccttgcttggcaacagcacagacccagctg
tgttcacagacctggcatccgtcgataactccgagtttca
gcagctgctgaaccagggcataccgtggccccccacaca -continued actgagcccatgctgatggagtaccctgaggctataactc gcctagtgacaggggcccagaggcccccgacccagctcc tgctccactgggggccccggggctcccaatggcctcctt tcaggagatgaagacttctcctccattgcggacatggact tctcagccctgctgagtcagatcagctctTAA

5.
JG1211: CAG-human dLbCpf1(D832A)-NLS-3xHA-VPR
Human codon optimized dLbCpf1: bold,
NLS: italic, 3xHA: lower case,
VPR: lower case and bold
(SEQ ID NO: 52)

ATGAGCAAGCTGGAGAAGTTTACAAACTGCTACTCCCTGT

CTAAGACCCTGAGGTTCAAGGCCATCCCTGTGGGCAAGAC

CCAGGAGAACATCGACAATAAGCGGCTGCTGGTGGAGGAC

GAGAAGAGAGCCGAGGATTATAAGGGCGTGAAGAAGCTGC

TGGATCGCTACTATCTGTCTTTTATCAACGACGTGCTGCA

CAGCATCAAGCTGAAGAATCTGAACAATTACATCAGCCTG

TTCCGGAAGAAAACCAGAACCGAGAAGGAGAATAAGGAGC

TGGAGAACCTGGAGATCAATCTGCGGAAGGAGATCGCCAA

GGCCTTCAAGGGCAACGAGGGCTACAAGTCCCTGTTTAAG

AAGGATATCATCGAGACAATCCTGCCAGAGTTCCTGGACG

ATAAGGACGAGATCGCCCTGGTGAACAGCTTCAATGGCTT

TACCACAGCCTTCACCGGCTTCTTTGATAACAGAGAGAAT

ATGTTTTCCGAGGAGGCCAAGAGCACATCCATCGCCTTCA

GGTGTATCAACGAGAATCTGACCCGCTACATCTCTAATAT

GGACATCTTCGAGAAGGTGGACGCCATCTTTGATAAGCAC

GAGGTGCAGGAGATCAAGGAGAAGATCCTGAACAGCGACT

ATGATGTGGAGGATTTCTTTGAGGGCGAGTTCTTTAACTT

TGTGCTGACACAGGAGGGCATCGACGTGTATAACGCCATC

ATCGGCGGCTTCGTGACCGAGAGCGGCGAGAAGATCAAGG

GCCTGAACGAGTACATCAACCTGTATAATCAGAAAACCAA

GCAGAAGCTGCCTAAGTTTAAGCCACTGTATAAGCAGGTG

CTGAGCGATCGGGAGTCTCTGAGCTTCTACGGCGAGGGCT

ATACATCCGATGAGGAGGTGCTGGAGGTGTTTAGAAACAC

CCTGAACAAGAACAGCGAGATCTTCAGCTCCATCAAGAAG

CTGGAGAAGCTGTTCAAGAATTTTGACGAGTACTCTAGCG

CCGGCATCTTTGTGAAGAACGGCCCCGCCATCAGCACAAT

CTCCAAGGATATCTTCGGCGAGTGGAACGTGATCCGGGAC

AAGTGGAATGCCGAGTATGACGATATCCACCTGAAGAAGA

AGGCCGTGGTGACCGAGAAGTACGAGGACGATCGGAGAAA

GTCCTTCAAGAAGATCGGCTCCTTTTCTCTGGAGCAGCTG

CAGGAGTACGCCGACGCCGATCTGTCTGTGGTGGAGAAGC

TGAAGGAGATCATCATCCAGAAGGTGGATGAGATCTACAA

GGTGTATGGCTCCTCTGAGAAGCTGTTCGACGCCGATTTT

GTGCTGGAGAAGAGCCTGAAGAAGAACGACGCCGTGGTGG

CCATCATGAAGGACCTGCTGGATTCTGTGAAGAGCTTCGA

GAATTACATCAAGGCCTTCTTTGGCGAGGGCAAGGAGACA

AACAGGGACGAGTCCTTCTATGGCGATTTTGTGCTGGCCT

ACGACATCCTGCTGAAGGTGGACCACATCTACGATGCCAT

CCGCAATTATGTGACCCAGAAGCCCTACTCTAAGGATAAG

TTCAAGCTGTATTTTCAGAACCCTCAGTTCATGGGCGGCT

GGGACAAGGATAAGGAGACAGACTATCGGGCCACCATCCT

GAGATACGGCTCCAAGTACTATCTGGCCATCATGGATAAG

AAGTACGCCAAGTGCCTGCAGAAGATCGACAAGGACGATG

TGAACGGCAATTACGAGAAGATCAACTATAAGCTGCTGCC

CGGCCCTAATAAGATGCTGCCAAAGGTGTTCTTTTCTAAG

AAGTGGATGGCCTACTATAACCCCAGCGAGGACATCCAGA

AGATCTACAAGAATGGCACATTCAAGAAGGGCGATATGTT

TAACCTGAATGACTGTCACAAGCTGATCGACTTCTTTAAG

GATAGCATCTCCCGGTATCCAAAGTGGTCCAATGCCTACG

ATTTCAACTTTTCTGAGACAGAGAAGTATAAGGACATCGC

CGGCTTTTACAGAGAGGTGGAGGAGCAGGGCTATAAGGTG

AGCTTCGAGTCTGCCAGCAAGAAGGAGGTGGATAAGCTGG

TGGAGGAGGGCAAGCTGTATATGTTCCAGATCTATAACAA

GGACTTTTCCGATAAGTCTCACGGCACACCCAATCTGCAC

ACCATGTACTTCAAGCTGCTGTTTGACGAGAACAATCACG

GACAGATCAGGCTGAGCGGAGGAGCAGAGCTGTTCATGAG

GCGCGCCTCCCTGAAGAAGGAGGAGCTGGTGGTGCACCCA

GCCAACTCCCCTATCGCCAACAAGAATCCAGATAATCCCA

AGAAAACCACAACCCTGTCCTACGACGTGTATAAGGATAA

GAGGTTTTCTGAGGACCAGTACGAGCTGCACATCCCAATC

GCCATCAATAAGTGCCCCAAGAACATCTTCAAGATCAATA

CAGAGGTGCGCGTGCTGCTGAAGCACGACGATAACCCCTA

TGTGATCGGCATCGCCAGGGGCGAGCGCAATCTGCTGTAT

ATCGTGGTGGTGGACGGCAAGGGCAACATCGTGGAGCAGT

ATTCCCTGAACGAGATCATCAACAACTTCAACGGCATCAG

GATCAAGACAGATTACCACTCTCTGCTGGACAAGAAGGAG

AAGGAGAGGTTCGAGGCCCGCCAGAACTGGACCTCCATCG

AGAATATCAAGGAGCTGAAGGCCGGCTATATCTCTCAGGT

GGTGCACAAGATCTGCGAGCTGGTGGAGAAGTACGATGCC

GTGATCGCCCTGGAGGACCTGAACTCTGGCTTTAAGAATA

GCCGCGTGAAGGTGGAGAAGCAGGTGTATCAGAAGTTCGA

GAAGATGCTGATCGATAAGCTGAACTACATGGTGGACAAG

AAGTCTAATCCTTGTGCAACAGGCGGCGCCCTGAAGGGCT

-continued
ATCAGATCACCAATAAGTTCGAGAGCTTTAAGTCCATGTC

TACCCAGAACGGCTTCATCTTTTACATCCCTGCCTGGCTG

ACATCCAAGATCGATCCATCTACCGGCTTTGTGAACCTGC

TGAAAACCAAGTATACCAGCATCGCCGATTCCAAGAAGTT

CATCAGCTCCTTTGACAGGATCATGTACGTGCCCGAGGAG

GATCTGTTCGAGTTTGCCCTGGACTATAAGAACTTCTCTC

GCACAGACGCCGATTACATCAAGAAGTGGAAGCTGTACTC

CTACGGCAACCGGATCAGAATCTTCCGGAATCCTAAGAAG

AACAACGTGTTCGACTGGGAGGAGGTGTGCCTGACCAGCG

CCTATAAGGAGCTGTTCAACAAGTACGGCATCAATTATCA

GCAGGGCGATATCAGAGCCCTGCTGTGCGAGCAGTCCGAC

AAGGCCTTCTACTCTAGCTTTATGGCCCTGATGAGCCTGA

TGCTGCAGATGCGGAACAGCATCACAGGCCGCACCGACGT

GGATTTTCTGATCAGCCCTGTGAAGAACTCCGACGGCATC

TTCTACGATAGCCGGAACTATGAGGCCCAGGAGAATGCCA

TCCTGCCAAAGAACGCCGACGCCAATGGCGCCTATAACAT

CGCCAGAAAGGTGCTGTGGGCCATCGGCCAGTTCAAGAAG

GCCGAGGACGAGAAGCTGGATAAGGTGAAGATCGCCATCT

CTAACAAGGAGTGGCTGGAGTACGCCCAGACCAGCGTGAA

GCAC*AAAAGGCCGGCGGCCACGAAAAAGGCCGGCCAGGCA*

*AAAAAGAAAAAGGG*ATCCtacccatacgatgttccagatt acgcttatccctacgacgtgcctgattatgcatacccata tgatgtccccgactatgccGGAAGCgaggccagcggttcc ggacgggctgacgcattggacgattttgatctggatatgc tgggaagtgacgccctcgatgattttgaccttgacatgct tggttcggatgcccttgatgactttgacctcgacatgctc ggcagtgacgcccttgatgatttcgacctggacatgctga ttaactctagaagttccggatctccgaaaaagaaacgcaa agttggtagccagtacctgcccgacaccgacgaccggcac cggatcgaggaaaagcggaagcggacctacgagacattca gagcatcatgaagaagtcccccttcagcggccccaccga ccctagacctccacctagaagaatcgccgtgcccagcaga tccagcgccagcgtgccaaaacctgccccccagccttacc ccttcaccagcagcctgagcaccatcaactacgacgagtt ccctaccatggtgttcccagcggccagatctctcaggcc tctgctctggctccagccctcctcaggtgctgcctcagg ctcctgctcctgcaccagctccagccatggtgtctgcact ggctcaggcaccagcaccgtgcctgtgctggctcctgga cctccacaggctgtggctccaccagccctaaacctacac aggccggcgagggcacactgtctgaagctctgctgcagct gcagttcgacgacgaggatctgggagccctgctgggaaac

-continued
agcaccgatcctgccgtgttcaccgacctggccagcgtgg acaacagcgagttccagcagctgctgaaccagggcatccc tgtggcccctcacaccaccgagcccatgctgatggaatac cccgaggccatcaccggctcgtgacaggcgctcagaggc ctcctgatccagctcctgcccctctgggagcaccaggcct gcctaatggactgctgtctggcgacgaggacttcagctct atcgccgatatggatttctcagccttgctgggctctggca gcggcagccgggattccagggaagggatgttttttgccgaa gcctgaggccggctccgctattagtgacgtgtttgagggc cgcgaggtgtgccagccaaaacgaatccggccatttcatc ctccaggaagtccatgggccaaccgcccactcccgccag cctcgcaccaacaccaaccggtccagtacatgagccagtc gggtcactgaccccggcaccagtccctcagccactggatc cagcgcccgcagtgactcccgaggccagtcacctgttgga ggatcccgatgaagagacgagccaggctgtcaaagccctt cgggagatggccgatactgtgattcccagaaggaagagg ctgcaatctgtggccaaatggaccttcccatccgcccc aagggggccatctggatgagctgacaaccacacttgagtcc atgaccgaggatctgaacctggactcacccctgaccccgg aattgaacgagattctggataccttcctgaacgacgagtg cctcttgcatgccatgcatatcagcacaggactgtccatc ttcgacacatctctgTTT

6. JG674: CAG-human dLbCpf1
(D832A)-NLS-3xHA-DmrA(X1)
Human codon optimized dLbCpf1: bold,
NLS: italic,
3xHA: lower case,
DmrA: lowercase and bold
(SEQ ID NO: 53)
ATGAGCAAGCTGGAGAAGTTTACAAACTGCTACTCCCTGT

CTAAGACCCTGAGGTTCAAGGCCATCCCTGTGGGCAAGAC

CCAGGAGAACATCGACAATAAGCGGCTGCTGGTGGAGGAC

GAGAAGAGAGCCGAGGATTATAAGGGCGTGAAGAAGCTGC

TGGATCGCTACTATCGTCTTTTATCAACGACGTGCTGCA

CAGCATCAAGCTGAAGAATCTGAACAATTACATCAGCCTG

TTCCGGAAGAAAACCAGAACCGAGAAGGAGAATAAGGAGC

TGGAGAACCTGGAGATCAATCTGCGGAAGGAGATCGCCAA

GGCCTTCAAGGGCAACGAGGGCTACAAGTCCCTGTTTAAG

AAGGATATCATCGAGACAATCCTGCCAGAGTTCCTGGACG

ATAAGGACGAGATCGCCCTGGTGAACAGCTTCAATGGCTT

TACCACAGCCTTCACCGGCTTCTTTGATAACAGAGAGAAT

ATGTTTTCCGAGGAGGCCAAGAGCACATCCATCGCCTTCA

GGTGTATCAACGAGAATCTGACCCGCTACATCTCTAATAT

GGACATCTTCGAGAAGGTGGACGCCATCTTTGATAAGCAC

GAGGTGCAGGAGATCAAGGAGAAGATCCTGAACAGCGACT

ATGATGTGGAGGATTTCTTTGAGGGCGAGTTCTTTAACTT

TGTGCTGACACAGGAGGGCATCGACGTGTATAACGCCATC

ATCGGCGGCTTCGTGACCGAGAGCGGCGAGAAGATCAAGG

GCCTGAACGAGTACATCAACCTGTATAATCAGAAAACCAA

GCAGAAGCTGCCTAAGTTTAAGCCACTGTATAAGCAGGTG

CTGAGCGATCGGGAGTCTCTGAGCTTCTACGGCGAGGGCT

ATACATCCGATGAGGAGGTGCTGGAGGTGTTTAGAAACAC

CCTGAACAAGAACAGCGAGATCTTCAGCTCCATCAAGAAG

CTGGAGAAGCTGTTCAAGAATTTTGACGAGTACTCTAGCG

CCGGCATCTTTGTGAAGAACGGCCCCGCCATCAGCACAAT

CTCCAAGGATATCTTCGGCGAGTGGAACGTGATCCGGGAC

AAGTGGAATGCCGAGTATGACGATATCCACCTGAAGAAGA

AGGCCGTGGTGACCGAGAAGTACGAGGACGATCGGAGAAA

GTCCTTCAAGAAGATCGGCTCCTTTTCTCTGGAGCAGCTG

CAGGAGTACGCCGACGCCGATCTGTCTGTGGTGGAGAAGC

TGAAGGAGATCATCATCCAGAAGGTGGATGAGATCTACAA

GGTGTATGGCTCCTCTGAGAAGCTGTTCGACGCCGATTTT

GTGCTGGAGAAGAGCCTGAAGAAGAACGACGCCGTGGTGG

CCATCATGAAGGACCTGCTGGATTCTGTGAAGAGCTTCGA

GAATTACATCAAGGCCTTCTTTGGCGAGGGCAAGGAGACA

AACAGGGACGAGTCCTTCTATGGCGATTTTGTGCTGGCCT

ACGACATCCTGCTGAAGGTGGACCACATCTACGATGCCAT

CCGCAATTATGTGACCCAGAAGCCCTACTCTAAGGATAAG

TTCAAGCTGTATTTTCAGAACCCTCAGTTCATGGGCGGCT

GGGACAAGGATAAGGAGACAGACTATCGGGCCACCATCCT

GAGATACGGCTCCAAGTACTATCTGGCCATCATGGATAAG

AAGTACGCCAAGTGCCTGCAGAAGATCGACAAGGACGATG

TGAACGGCAATTACGAGAAGATCAACTATAAGCTGCTGCC

CGGCCCTAATAAGATGCTGCCAAAGGTGTTCTTTTCTAAG

AAGTGGATGGCCTACTATAACCCCAGCGAGGACATCCAGA

AGATCTACAAGAATGGCACATTCAAGAAGGGCGATATGTT

TAACCTGAATGACTGTCACAAGCTGATCGACTTCTTTAAG

GATAGCATCTCCCGGTATCCAAAGTGGTCCAATGCCTACG

ATTTCAACTTTTCTGAGACAGAGAAGTATAAGGACATCGC

CGGCTTTTACAGAGAGGTGGAGGAGCAGGGCTATAAGGTG

AGCTTCGAGTCTGCCAGCAAGAAGGAGGTGGATAAGCTGG

TGGAGGAGGGCAAGCTGTATATGTTCCAGATCTATAACAA

GGACTTTTCCGATAAGTCTCACGGCACACCCAATCTGCAC

ACCATGTACTTCAAGCTGCTGTTTGACGAGAACAATCACG

GACAGATCAGGCTGAGCGGAGGAGCAGAGCTGTTCATGAG

GCGCGCCTCCCTGAAGAAGGAGGAGCTGGTGGTGCACCCA

GCCAACTCCCCTATCGCCAACAAGAATCCAGATAATCCCA

AGAAAACCACAACCCTGTCCTACGACGTGTATAAGGATAA

GAGGTTTTCTGAGGACCAGTACGAGCTGCACATCCCAATC

GCCATCAATAAGTGCCCCAAGAACATCTTCAAGATCAATA

CAGAGGTGCGCGTGCTGCTGAAGCACGACGATAACCCCTA

TGTGATCGGCATCGCCAGGGGCGAGCGCAATCTGCTGTAT

ATCGTGGTGGTGGACGGCAAGGGCAACATCGTGGAGCAGT

ATTCCCTGAACGAGATCATCAACAACTTCAACGGCATCAG

GATCAAGACAGATTACCACTCTCTGCTGGACAAGAAGGAG

AAGGAGAGGTTCGAGGCCCGCCAGAACTGGACCTCCATCG

AGAATATCAAGGAGCTGAAGGCCGGCTATATCTCTCAGGT

GGTGCACAAGATCTGCGAGCTGGTGGAGAAGTACGATGCC

GTGATCGCCCTGGAGGACCTGAACTCTGGCTTTAAGAATA

GCCGCGTGAAGGTGGAGAAGCAGGTGTATCAGAAGTTCGA

GAAGATGCTGATCGATAAGCTGAACTACATGGTGGACAAG

AAGTCTAATCCTTGTGCAACAGGCGGCGCCCTGAAGGGCT

ATCAGATCACCAATAAGTTCGAGAGCTTTAAGTCCATGTC

TACCCAGAACGGCTTCATCTTTTACATCCCTGCCTGGCTG

ACATCCAAGATCGATCCATCTACCGGCTTTGTGAACCTGC

TGAAAACCAAGTATACCAGCATCGCCGATTCCAAGAAGTT

CATCAGCTCCTTTGACAGGATCATGTACGTGCCCGAGGAG

GATCTGTTCGAGTTTGCCCTGGACTATAAGAACTTCTCTC

GCACAGACGCCGATTACATCAAGAAGTGGAAGCTGTACTC

CTACGGCAACCGGATCAGAATCTTCCGGAATCCTAAGAAG

AACAACGTGTTCGACTGGGAGGAGGTGTGCCTGACCAGCG

CCTATAAGGAGCTGTTCAACAAGTACGGCATCAATTATCA

GCAGGGCGATATCAGAGCCCTGCTGTGCGAGCAGTCCGAC

AAGGCCTTCTACTCTAGCTTTATGGCCCTGATGAGCCTGA

TGCTGCAGATGCGGAACAGCATCACAGGCCGCACCGACGT

GGATTTTCTGATCAGCCCTGTGAAGAACTCCGACGGCATC

TTCTACGATAGCCGGAACTATGAGGCCCAGGAGAATGCCA

TCCTGCCAAAGAACGCCGACGCCAATGGCGCCTATAACAT

CGCCAGAAAGGTGCTGTGGGCCATCGGCCAGTTCAAGAAG

GCCGAGGACGAGAAGCTGGATAAGGTGAAGATCGCCATCT

CTAACAAGGAGTGGCTGGAGTACGCCCAGACCAGCGTGAA

GCAC*AAAAGGCCGGCGGCCACGAAAAAGGCCGGCCAGGCA*

*AAAAAGAAAAAGGGATCC*tacccatacgatgttccagatt acgcttatccctacgacgtgcctgattatgcatacccata tgatgtccccgactatgccTCGAGCGACTACAAAGACCAT

GACGGTGATTATAAAGATCATGACATCGATTACAAGGATG

ACGATGACAAGGCTGCAGGAGGCGGTGGAAGCGGGaggggagtgcaggtggaaaccatctccccaggagacgggcgcaccttccccaagcgcggccagacctgcgtggtgcactacaccggatgcttgaagatggaaagaaatttgattcctcccggacagaaacaagcccttaagtttatgctaggcaagcaggaggtgatccgaggctgggaagaaggggttgcccagatgagtgtgggtcagagagccaaactgactatatctccagattatgcctatggtgccactgggcacccaggcatcatcccaccacatgccactctcgtcttcgatgtggagcttctaaaactggaaG

GATAA

7. JG676: CAG-human dLbCpf1(D832A)-NLS-3xHA-DmrA(X2)
Human codon optimized dLbCpf1: bold,
NLS: italic,
3xHA: lower case,
DmrA: lowercase and bold (SEQ ID NO: 54)

ATGAGCAAGCTGGAGAAGTTTACAAACTGCTACTCCCTGT

CTAAGACCCTGAGGTTCAAGGCCATCCCTGTGGGCAAGAC

CCAGGAGAACATCGACAATAAGCGGCTGCTGGTGGAGGAC

GAGAAGAGAGCCGAGGATTATAAGGGCGTGAAGAAGCTGC

TGGATCGCTACTATCTGTCTTTTATCAACGACGTGCTGCA

CAGCATCAAGCTGAAGAATCTGAACAATTACATCAGCCTG

TTCCGGAAGAAAACCAGAACCGAGAAGGAGAATAAGGAGC

TGGAGAACCTGGAGATCAATCTGCGGAAGGAGATCGCCAA

GGCCTTCAAGGGCAACGAGGGCTACAAGTCCCTGTTTAAG

AAGGATATCATCGAGACAATCCTGCCAGAGTTCCTGGACG

ATAAGGACGAGATCGCCCTGGTGAACAGCTTCAATGGCTT

TACCACAGCCTTCACCGGCTTCTTTGATAACAGAGAGAAT

ATGTTTTCCGAGGAGGCCAAGAGCACATCCATCGCCTTCA

GGTGTATCAACGAGAATCTGACCCGCTACATCTCTAATAT

GGACATCTTCGAGAAGGTGGACGCCATCTTTGATAAGCAC

GAGGTGCAGGAGATCAAGGAGAAGATCCTGAACAGCGACT

ATGATGTGGAGGATTTCTTTGAGGGCGAGTTCTTTAACTT

TGTGCTGACACAGGAGGGCATCGACGTGTATAACGCCATC

ATCGGCGGCTTCGTGACCGAGAGCGGCGAGAAGATCAAGG

GCCTGAACGAGTACATCAACCTGTATAATCAGAAAACCAA

GCAGAAGCTGCCTAAGTTTAAGCCACTGTATAAGCAGGTG

CTGAGCGATCGGGAGTCTCTGAGCTTCTACGGCGAGGGCT

ATACATCCGATGAGGAGGTGCTGGAGGTGTTTAGAAACAC

CCTGAACAAGAACAGCGAGATCTTCAGCTCCATCAAGAAG

CTGGAGAAGCTGTTCAAGAATTTTGACGAGTACTCTAGCG

CCGGCATCTTTGTGAAGAACGGCCCCGCCATCAGCACAAT

CTCCAAGGATATCTTCGGCGAGTGGAACGTGATCCGGGAC

AAGTGGAATGCCGAGTATGACGATATCCACCTGAAGAAGA

AGGCCGTGGTGACCGAGAAGTACGAGGACGATCGGAGAAA

GTCCTTCAAGAAGATCGGCTCCTTTTCTCTGGAGCAGCTG

CAGGAGTACGCCGACGCCGATCTGTCTGTGGTGGAGAAGC

TGAAGGAGATCATCATCCAGAAGGTGGATGAGATCTACAA

GGTGTATGGCTCCTCTGAGAAGCTGTTCGACGCCGATTTT

GTGCTGGAGAAGAGCCTGAAGAAGAACGACGCCGTGGTGG

CCATCATGAAGGACCTGCTGGATTCTGTGAAGAGCTTCGA

GAATTACATCAAGGCCTTCTTTGGCGAGGGCAAGGAGACA

AACAGGGACGAGTCCTTCTATGGCGATTTTGTGCTGGCCT

ACGACATCCTGCTGAAGGTGGACCACATCTACGATGCCAT

CCGCAATTATGTGACCCAGAAGCCCTACTCTAAGGATAAG

TTCAAGCTGTATTTTCAGAACCCTCAGTTCATGGGCGGCT

GGGACAAGGATAAGGAGACAGACTATCGGGCCACCATCCT

GAGATACGGCTCCAAGTACTATCTGGCCATCATGGATAAG

AAGTACGCCAAGTGCCTGCAGAAGATCGACAAGGACGATG

TGAACGGCAATTACGAGAAGATCAACTATAAGCTGCTGCC

CGGCCCTAATAAGATGCTGCCAAAGGTGTTCTTTTCTAAG

AAGTGGATGGCCTACTATAACCCCAGCGAGGACATCCAGA

AGATCTACAAGAATGGCACATTCAAGAAGGGCGATATGTT

TAACCTGAATGACTGTCACAAGCTGATCGACTTCTTTAAG

GATAGCATCTCCCGGTATCCAAAGTGGTCCAATGCCTACG

ATTTCAACTTTTCTGAGACAGAGAAGTATAAGGACATCGC

CGGCTTTTACAGAGAGGTGGAGGAGCAGGGCTATAAGGTG

AGCTTCGAGTCTGCCAGCAAGAAGGAGGTGGATAAGCTGG

TGGAGGAGGGCAAGCTGTATATGTTCCAGATCTATAACAA

GGACTTTTCCGATAAGTCTCACGGCACACCCAATCTGCAC

ACCATGTACTTCAAGCTGCTGTTTGACGAGAACAATCACG

GACAGATCAGGCTGAGCGGAGGAGCAGAGCTGTTCATGAG

GCGCGCCTCCCTGAAGAAGGAGGAGCTGGTGGTGCACCCA

GCCAACTCCCCTATCGCCAACAAGAATCCAGATAATCCCA

AGAAAACCACAACCCTGTCCTACGACGTGTATAAGGATAA

GAGGTTTTCTGAGGACCAGTACGAGCTGCACATCCCAATC

GCCATCAATAAGTGCCCCAAGAACATCTTCAAGATCAATA

CAGAGGTGCGCGTGCTGCTGAAGCACGACGATAACCCCTA

TGTGATCGGCATCGCCAGGGGCGAGCGCAATCTGCTGTAT

ATCGTGGTGGTGGACGGCAAGGGCAACATCGTGGAGCAGT

ATTCCCTGAACGAGATCATCAACAACTTCAACGGCATCAG

GATCAAGACAGATTACCACTCTCTGCTGGACAAGAAGGAG

```
AAGGAGAGGTTCGAGGCCCGCCAGAACTGGACCTCCATCG
AGAATATCAAGGAGCTGAAGGCCGGCTATATCTCTCAGGT
GGTGCACAAGATCTGCGAGCTGGTGGAGAAGTACGATGCC
GTGATCGCCCTGGAGGACCTGAACTCTGGCTTTAAGAATA
GCCGCGTGAAGGTGGAGAAGCAGGTGTATCAGAAGTTCGA
GAAGATGCTGATCGATAAGCTGAACTACATGGTGGACAAG
AAGTCTAATCCTTGTGCAACAGGCGGCGCCCTGAAGGGCT
ATCAGATCACCAATAAGTTCGAGAGCTTTAAGTCCATGTC
TACCCAGAACGGCTTCATCTTTTACATCCCTGCCTGGCTG
ACATCCAAGATCGATCCATCTACCGGCTTTGTGAACCTGC
TGAAAACCAAGTATACCAGCATCGCCGATTCCAAGAAGTT
CATCAGCTCCTTTGACAGGATCATGTACGTGCCCGAGGAG
GATCTGTTCGAGTTTGCCCTGGACTATAAGAACTTCTCTC
GCACAGACGCCGATTACATCAAGAAGTGGAAGCTGTACTC
CTACGGCAACCGGATCAGAATCTTCCGGAATCCTAAGAAG
AACAACGTGTTCGACTGGGAGGAGGTGTGCCTGACCAGCG
CCTATAAGGAGCTGTTCAACAAGTACGGCATCAATTATCA
GCAGGGCGATATCAGAGCCCTGCTGTGCGAGCAGTCCGAC
AAGGCCTTCTACTCTAGCTTTATGGCCCTGATGAGCCTGA
TGCTGCAGATGCGGAACAGCATCACAGGCCGCACCGACGT
GGATTTTCTGATCAGCCCTGTGAAGAACTCCGACGGCATC
TTCTACGATAGCCGGAACTATGAGGCCCAGGAGAATGCCA
TCCTGCCAAAGAACGCCGACGCCAATGGCGCCTATAACAT
CGCCAGAAAGGTGCTGTGGGCCATCGGCCAGTTCAAGAAG
GCCGAGGACGAGAAGCTGGATAAGGTGAAGATCGCCATCT
CTAACAAGGAGTGGCTGGAGTACGCCCAGACCAGCGTGAA
GCACAAAAGGCCGGCGGCCACGAAAAAGGCCGGCCAGGCA
AAAAAGAAAAAGGGATCCtacccatacgatgttccagatt
acgcttatccctacgacgtgcctgattatgcatacccata
tgatgtccccgactatgccTCGAGCGACTACAAAGACCAT
GACGGTGATTATAAAGATCATGACATCGATTACAAGGATG
ACGATGACAAGGCTGCAGGAGGCGGTGGAAGCGGGagggg
agtgcaggtggaaaccatctccccaggagacgggcgcacc
ttccccaagcgcggccagacctgcgtggtgcactacaccg
ggatgcttgaagatggaaagaaatttgattcctcccggga
cagaaacaagcccttaagtttatgctaggcaagcaggag
gtgatccgaggctgggaagaaggggttgcccagatgagtg
tgggtcagagagccaaactgactatatctccagattatgc
ctatggtgccactgggcacccaggcatcatcccaccacat
gccactctcgtcttcgatgtggagcttctaaaactggaaG
GTTCtaggggagtgcaggtggaaaccatctccccaggaga
```

```
cgggcgcaccttccccaagcgcggccagacctgcgtggtg
cactacaccgggatgcttgaagatggaaagaaatttgatt
cctcccgggacagaaacaagcccttaagtttatgctagg
caagcaggaggtgatccgaggctgggaagaaggggttgcc
cagatgagtgtgggtcagagagccaaactgactatatctc
cagattatgcctatggtgccactgggcacccaggcatcat
cccaccacatgccactctcgtcttcgatgtggagcttcta
aaactggaaGGATAA 8.
JG693: CAG-human dLbCpf1(D832A)-
NLS-3xHA-DmrA(X3)
Human codon optimized dLbCpf1: bold,
NLS: italic, 3xHA: lower case,
DmrA: lowercase and bold
                              (SEQ ID NO: 55)
ATGAGCAAGCTGGAGAAGTTTACAAACTGCTACTCCCTGT
CTAAGACCCTGAGGTTCAAGGCCATCCCTGTGGGCAAGAC
CCAGGAGAACATCGACAATAAGCGGCTGCTGGTGGAGGAC
GAGAAGAGAGCCGAGGATTATAAGGGCGTGAAGAAGCTGC
TGGATCGCTACTATCTGTCTTTTATCAACGACGTGCTGCA
CAGCATCAAGCTGAAGAATCTGAACAATTACATCAGCCTG
TTCCGGAAGAAAACCAGAACCGAGAAGGAGAATAAGGAGC
TGGAGAACCTGGAGATCAATCTGCGGAAGGAGATCGCCAA
GGCCTTCAAGGGCAACGAGGGCTACAAGTCCCTGTTTAAG
AAGGATATCATCGAGACAATCCTGCCAGAGTTCCTGGACG
ATAAGGACGAGATCGCCCTGGTGAACAGCTTCAATGGCTT
TACCACAGCCTTCACCGGCTTCTTTGATAACAGAGAGAAT
ATGTTTTCCGAGGAGGCCAAGAGCACATCCATCGCCTTCA
GGTGTATCAACGAGAATCTGACCCGCTACATCTCTAATAT
GGACATCTTCGAGAAGGTGGACGCCATCTTTGATAAGCAC
GAGGTGCAGGAGATCAAGGAGAAGATCCTGAACAGCGACT
ATGATGTGGAGGATTTCTTTGAGGGCGAGTTCTTTAACTT
TGTGCTGACACAGGAGGGCATCGACGTGTATAACGCCATC
ATCGGCGGCTTCGTGACCGAGAGCGGCGAGAAGATCAAGG
GCCTGAACGAGTACATCAACCTGTATAATCAGAAAACCAA
GCAGAAGCTGCCTAAGTTTAAGCCACTGTATAAGCAGGTG
CTGAGCGATCGGGAGTCTCTGAGCTTCTACGGCGAGGGCT
ATACATCCGATGAGGAGGTGCTGGAGGTGTTTAGAAACAC
CCTGAACAAGAACAGCGAGATCTTCAGCTCCATCAAGAAG
CTGGAGAAGCTGTTCAAGAATTTTGACGAGTACTCTAGCG
CCGGCATCTTTGTGAAGAACGGCCCCGCCATCAGCACAAT
CTCCAAGGATATCTTCGGCGAGTGGAACGTGATCCGGGAC
AAGTGGAATGCCGAGTATGACGATATCCACCTGAAGAAGA
AGGCCGTGGTGACCGAGAAGTACGAGGACGATCGGAGAAA
```

GTCCTTCAAGAAGATCGGCTCCTTTTCTCTGGAGCAGCTG
CAGGAGTACGCCGACGCCGATCTGTCTGTGGTGGAGAAGC
TGAAGGAGATCATCATCCAGAAGGTGGATGAGATCTACAA
GGTGTATGGCTCCTCTGAGAAGCTGTTCGACGCCGATTTT
GTGCTGGAGAAGAGCCTGAAGAAGAACGACGCCGTGGTGG
CCATCATGAAGGACCTGCTGGATTCTGTGAAGAGCTTCGA
GAATTACATCAAGGCCTTCTTTGGCGAGGGCAAGGAGACA
AACAGGGACGAGTCCTTCTATGGCGATTTTGTGCTGGCCT
ACGACATCCTGCTGAAGGTGGACCACATCTACGATGCCAT
CCGCAATTATGTGACCCAGAAGCCCTACTCTAAGGATAAG
TTCAAGCTGTATTTTCAGAACCCTCAGTTCATGGGCGGCT
GGGACAAGGATAAGGAGACAGACTATCGGGCCACCATCCT
GAGATACGGCTCCAAGTACTATCTGGCCATCATGGATAAG
AAGTACGCCAAGTGCCTGCAGAAGATCGACAAGGACGATG
TGAACGGCAATTACGAGAAGATCAACTATAAGCTGCTGCC
CGGCCCTAATAAGATGCTGCCAAAGGTGTTCTTTTCTAAG
AAGTGGATGGCCTACTATAACCCCAGCGAGGACATCCAGA
AGATCTACAAGAATGGCACATTCAAGAAGGGCGATATGTT
TAACCTGAATGACTGTCACAAGCTGATCGACTTCTTTAAG
GATAGCATCTCCCGGTATCCAAAGTGGTCCAATGCCTACG
ATTTCAACTTTTCTGAGACAGAGAAGTATAAGGACATCGC
CGGCTTTTACAGAGAGGTGGAGGAGCAGGGCTATAAGGTG
AGCTTCGAGTCTGCCAGCAAGAAGGAGGTGGATAAGCTGG
TGGAGGAGGGCAAGCTGTATATGTTCCAGATCTATAACAA
GGACTTTTCCGATAAGTCTCACGGCACACCCAATCTGCAC
ACCATGTACTTCAAGCTGCTGTTTGACGAGAACAATCACG
GACAGATCAGGCTGAGCGGAGGAGCAGAGCTGTTCATGAG
GCGCGCCTCCCTGAAGAAGGAGGAGCTGGTGGTGCACCCA
GCCAACTCCCCTATCGCCAACAAGAATCCAGATAATCCCA
AGAAAACCACAACCCTGTCCTACGACGTGTATAAGGATAA
GAGGTTTTCTGAGGACCAGTACGAGCTGCACATCCCAATC
GCCATCAATAAGTGCCCCAAGAACATCTTCAAGATCAATA
CAGAGGTGCGCGTGCTGCTGAAGCACGACGATAACCCCTA
TGTGATCGGCATCGCCAGGGGCGAGCGCAATCTGCTGTAT
ATCGTGGTGGTGGACGGCAAGGGCAACATCGTGGAGCAGT
ATTCCCTGAACGAGATCATCAACAACTTCAACGGCATCAG
GATCAAGACAGATTACCACTCTCTGCTGGACAAGAAGGAG
AAGGAGAGGTTCGAGGCCCGCCAGAACTGGACCTCCATCG
AGAATATCAAGGAGCTGAAGGCCGGCTATATCTCTCAGGT
GGTGCACAAGATCTGCGAGCTGGTGGAGAAGTACGATGCC

GTGATCGCCCTGGAGGACCTGAACTCTGGCTTTAAGAATA
GCCGCGTGAAGGTGGAGAAGCAGGTGTATCAGAAGTTCGA
GAAGATGCTGATCGATAAGCTGAACTACATGGTGGACAAG
AAGTCTAATCCTTGTGCAACAGGCGGCGCCCTGAAGGGCT
ATCAGATCACCAATAAGTTCGAGAGCTTTAAGTCCATGTC
TACCCAGAACGGCTTCATCTTTTACATCCCTGCCTGGCTG
ACATCCAAGATCGATCCATCTACCGGCTTTGTGAACCTGC
TGAAAACCAAGTATACCAGCATCGCCGATTCCAAGAAGTT
CATCAGCTCCTTTGACAGGATCATGTACGTGCCCGAGGAG
GATCTGTTCGAGTTTGCCCTGGACTATAAGAACTTCTCTC
GCACAGACGCCGATTACATCAAGAAGTGGAAGCTGTACTC
CTACGGCAACCGGATCAGAATCTTCCGGAATCCTAAGAAG
AACAACGTGTTCGACTGGGAGGAGGTGTGCCTGACCAGCG
CCTATAAGGAGCTGTTCAACAAGTACGGCATCAATTATCA
GCAGGGCGATATCAGAGCCCTGCTGTGCGAGCAGTCCGAC
AAGGCCTTCTACTCTAGCTTTATGGCCCTGATGAGCCTGA
TGCTGCAGATGCGGAACAGCATCACAGGCCGCACCGACGT
GGATTTTCTGATCAGCCCTGTGAAGAACTCCGACGGCATC
TTCTACGATAGCCGGAACTATGAGGCCCAGGAGAATGCCA
TCCTGCCAAAGAACGCCGACGCCAATGGCGCCTATAACAT
CGCCAGAAAGGTGCTGTGGGCCATCGGCCAGTTCAAGAAG
GCCGAGGACGAGAAGCTGGATAAGGTGAAGATCGCCATCT
CTAACAAGGAGTGGCTGGAGTACGCCCAGACCAGCGTGAA
GCACAAAAGGCCGGCGGCCACGAAAAAGGCCGGCCAGGCA
AAAAAGAAAAAGGGATCCtacccatacgatgttccagatt
acgcttatccctacgacgtgcctgattatgcatacccata
tgatgtccccgactatgccTCGAGCGACTACAAAGACCAT
GACGGTGATTATAAAGATCATGACATCGATTACAAGGATG
ACGATGACAAGGCTGCAGGAGGCGGTGGAAGCGGGaggggg
agtgcaggtggaaaccatctccccaggagacgggcgcacc
ttccccaagcgcggccagacctgcgtggtgcactacaccg
ggatgcttgaagatggaaagaaatttgattcctcccggga
cagaaacaagcccttaagtttatgctaggcaagcaggag
gtgatccgaggctgggaagaaggggttgcccagatgagtg
tgggtcagagagccaaactgactatatctccagattatgc
ctatggtgccactgggcacccaggcatcatccaccacat
gccactctcgtcttcgatgtggagcttctaaaactggaag
gatctggtggaaGCGGaggggagtgcaggtggaaaccat
ctccccaggagacgggcgcaccttccccaagcgcggccag
acctgcgtggtgcactacaccgggatgcttgaagatgaa
agaaatttgattcctcccgggacagaaacaagcccttaa -continued gtttatgctaggcaagcaggaggtgatccgaggctgggaa gaaggggttgcccagatgagtgtgggtcagagagccaaac tgactatatctccagattatgcctatggtgccactgggca cccaggcatcatcccaccacatgccactctcgtcttcgat gtggagcttctaaaactggaaGGTTCTaggggagtgcagg tggaaaccatctcccaggagacgggcgcaccttccccaa gcgcggccagacctgcgtggtgcactacaccgggatgctt gaagatggaaagaaatttgattcctcccgggacagaaaca agcccctttaagtttatgctaggcaagcaggaggtgatccg aggctgggaagaaggggttgcccagatgagtgtgggtcag agagccaaactgactatatctccagattatgcctatggtg ccactgggcacccaggcatcatcccaccacatgccactct cgtcttcgatgtggagcttctaaaactggaaGGATAA 9. YET1000: CAG-human dLbCpf1(D832A)-NLS-3xHA-DmrA(X4)
Human codon optimized dLbCpf1: bold, NLS: italic, 3xHA: lower case, DmrA: lowercase and bold (SEQ ID NO: 56)
ATGAGCAAGCTGGAGAAGTTTACAAACTGCTACTCCCTGT

CTAAGACCCTGAGGTTCAAGGCCATCCCTGTGGGCAAGAC

CCAGGAGAACATCGACAATAAGCGGCTGCTGGTGGAGGAC

GAGAAGAGAGCCGAGGATTATAAGGGCGTGAAGAAGCTGC

TGGATCGCTACTATCTGTCTTTTATCAACGACGTGCTGCA

CAGCATCAAGCTGAAGAATCTGAACAATTACATCAGCCTG

TTCCGGAAGAAAACCAGAACCGAGAAGGAGAATAAGGAGC

TGGAGAACCTGGAGATCAATCTGCGGAAGGAGATCGCCAA

GGCCTTCAAGGGCAACGAGGGCTACAAGTCCCTGTTTAAG

AAGGATATCATCGAGACAATCCTGCCAGAGTTCCTGGACG

ATAAGGACGAGATCGCCCTGGTGAACAGCTTCAATGGCTT

TACCACAGCCTTCACCGGCTTCTTTGATAACAGAGAGAAT

ATGTTTTCCGAGGAGGCCAAGAGCACATCCATCGCCTTCA

GGTGTATCAACGAGAATCTGACCCGCTACATCTCTAATAT

GGACATCTTCGAGAAGGTGGACGCCATCTTTGATAAGCAC

GAGGTGCAGGAGATCAAGGAGAAGATCCTGAACAGCGACT

ATGATGTGGAGGATTTCTTTGAGGGCGAGTTCTTTAACTT

TGTGCTGACACAGGAGGGCATCGACGTGTATAACGCCATC

ATCGGCGGCTTCGTGACCGAGAGCGGCGAGAAGATCAAGG

GCCTGAACGAGTACATCAACCTGTATAATCAGAAAACCAA

GCAGAAGCTGCCTAAGTTTAAGCCACTGTATAAGCAGGTG

CTGAGCGATCGGGAGTCTCTGAGCTTCTACGGCGAGGGCT

ATACATCCGATGAGGAGGTGCTGGAGGTGTTTAGAAACAC

CCTGAACAAGAACAGCGAGATCTTCAGCTCCATCAAGAAG

CTGGAGAAGCTGTTCAAGAATTTTGACGAGTACTCTAGCG

CCGGCATCTTTGTGAAGAACGGCCCCGCCATCAGCACAAT

CTCCAAGGATATCTTCGGCGAGTGGAACGTGATCCGGGAC

AAGTGGAATGCCGAGTATGACGATATCCACCTGAAGAAGA

AGGCCGTGGTGACCGAGAAGTACGAGGACGATCGGAGAAA

GTCCTTCAAGAAGATCGGCTCCTTTTCTCTGGAGCAGCTG

CAGGAGTACGCCGACGCCGATCTGTCTGTGGTGGAGAAGC

TGAAGGAGATCATCATCCAGAAGGTGGATGAGATCTACAA

GGTGTATGGCTCCTCTGAGAAGCTGTTCGACGCCGATTTT

GTGCTGGAGAAGAGCCTGAAGAAGAACGACGCCGTGGTGG

CCATCATGAAGGACCTGCTGGATTCTGTGAAGAGCTTCGA

GAATTACATCAAGGCCTTCTTTGGCGAGGGCAAGGAGACA

AACAGGGACGAGTCCTTCTATGGCGATTTTGTGCTGGCCT

ACGACATCCTGCTGAAGGTGGACCACATCTACGATGCCAT

CCGCAATTATGTGACCCAGAAGCCCTACTCTAAGGATAAG

TTCAAGCTGTATTTTCAGAACCCTCAGTTCATGGGCGGCT

GGGACAAGGATAAGGAGACAGACTATCGGGCCACCATCCT

GAGATACGGCTCCAAGTACTATCTGGCCATCATGGATAAG

AAGTACGCCAAGTGCCTGCAGAAGATCGACAAGGACGATG

TGAACGGCAATTACGAGAAGATCAACTATAAGCTGCTGCC

CGGCCCTAATAAGATGCTGCCAAAGGTGTTCTTTTCTAAG

AAGTGGATGGCCTACTATAACCCCAGCGAGGACATCCAGA

AGATCTACAAGAATGGCACATTCAAGAAGGGCGATATGTT

TAACCTGAATGACTGTCACAAGCTGATCGACTTCTTTAAG

GATAGCATCTCCCGGTATCCAAAGTGGTCCAATGCCTACG

ATTTCAACTTTTCTGAGACAGAGAAGTATAAGGACATCGC

CGGCTTTTACAGAGAGGTGGAGGAGCAGGGCTATAAGGTG

AGCTTCGAGTCTGCCAGCAAGAAGGAGGTGGATAAGCTGG

TGGAGGAGGGCAAGCTGTATATGTTCCAGATCTATAACAA

GGACTTTTCCGATAAGTCTCACGGCACACCCAATCTGCAC

ACCATGTACTTCAAGCTGCTGTTTGACGAGAACAATCACG

GACAGATCAGGCTGAGCGGAGGAGCAGAGCTGTTCATGAG

GCGCGCCTCCCTGAAGAAGGAGGAGCTGGTGGTGCACCCA

GCCAACTCCCCTATCGCCAACAAGAATCCAGATAATCCCA

AGAAAACCACAACCCTGTCCTACGACGTGTATAAGGATAA

GAGGTTTTCTGAGGACCAGTACGAGCTGCACATCCCAATC

GCCATCAATAAGTGCCCCAAGAACATCTTCAAGATCAATA

CAGAGGTGCGCGTGCTGCTGAAGCACGACGATAACCCCTA

TGTGATCGGCATCGCCAGGGGCGAGCGCAATCTGCTGTAT

ATCGTGGTGGTGGACGGCAAGGGCAACATCGTGGAGCAGT

ATTCCCTGAACGAGATCATCAACAACTTCAACGGCATCAG

-continued

GATCAAGACAGATTACCACTCTCTGCTGGACAAGAAGGAG

AAGGAGAGGTTCGAGGCCCGCCAGAACTGGACCTCCATCG

AGAATATCAAGGAGCTGAAGGCCGGCTATATCTCTCAGGT

GGTGCACAAGATCTGCGAGCTGGTGGAGAAGTACGATGCC

GTGATCGCCCTGGAGGACCTGAACTCTGGCTTTAAGAATA

GCCGCGTGAAGGTGGAGAAGCAGGTGTATCAGAAGTTCGA

GAAGATGCTGATCGATAAGCTGAACTACATGGTGGACAAG

AAGTCTAATCCTTGTGCAACAGGCGGCGCCCTGAAGGGCT

ATCAGATCACCAATAAGTTCGAGAGCTTTAAGTCCATGTC

TACCCAGAACGGCTTCATCTTTTACATCCCTGCCTGGCTG

ACATCCAAGATCGATCCATCTACCGGCTTTGTGAACCTGC

TGAAAACCAAGTATACCAGCATCGCCGATTCCAAGAAGTT

CATCAGCTCCTTTGACAGGATCATGTACGTGCCCGAGGAG

GATCTGTTCGAGTTTGCCCTGGACTATAAGAACTTCTCTC

GCACAGACGCCGATTACATCAAGAAGTGGAAGCTGTACTC

CTACGGCAACCGGATCAGAATCTTCCGGAATCCTAAGAAG

AACAACGTGTTCGACTGGGAGGAGGTGTGCCTGACCAGCG

CCTATAAGGAGCTGTTCAACAAGTACGGCATCAATTATCA

GCAGGGCGATATCAGAGCCCTGCTGTGCGAGCAGTCCGAC

AAGGCCTTCTACTCTAGCTTTATGGCCCTGATGAGCCTGA

TGCTGCAGATGCGGAACAGCATCACAGGCCGCACCGACGT

GGATTTTCTGATCAGCCCTGTGAAGAACTCCGACGGCATC

TTCTACGATAGCCGGAACTATGAGGCCCAGGAGAATGCCA

TCCTGCCAAAGAACGCCGACGCCAATGGCGCCTATAACAT

CGCCAGAAAGGTGCTGTGGGCCATCGGCCAGTTCAAGAAG

GCCGAGGACGAGAAGCTGGATAAGGTGAAGATCGCCATCT

CTAACAAGGAGTGGCTGGAGTACGCCCAGACCAGCGTGAA

GCACAAAAGGCCGGCGGCCACGAAAAAGGCCGGCCAGGCA

AAAAAGAAAAAGGGATCCtacccatacgatgttccagatt acgcttatccctacgacgtgcctgattatgcatacccata tgatgtccccgactatgccTCGAGCGACTACAAAGACCAT

GACGGTGATTATAAAGATCATGACATCGATTACAAGGATG

ACGATGACAAGGCTGCAGGAGGCGGTGGAAGCGGGGAAg ggagtgcaggtggaaaccatctccccaggagacgggcgc accttccccaagcgcggccagacctgcgtggtgcactaca ccgggatgcttgaagatggaaagaaatttgattcctcccg ggacagaaacaagccctttaagtttatgctaggcaagcag gaggtgatccgaggctgggaagaaggggttgcccagatga gtgtgggtcagagagccaaactgactatatctccagatta tgcctatggtgccactgggcacccaggcatcatcccacca catgccactctcgtcttcgatgtggagcttctaaaactgg aaGGTTCTaggggagtgcaggtggaaaccatctccccagg agacgggcgcaccttccccaagcgcggccagacctgcgtg gtgcactacaccgggatgcttgaagatggaaagaaatttg attcctcccgggacagaaacaagccctttaagtttatgct aggcaagcaggaggtgatccgaggctgggaagaaggggtt gcccagatgagtgtgggtcagagagccaaactgactatat ctccagattatgcctatggtgccactgggcacccaggcat catcccaccacatgccactctcgtcttcgatgtggagctt ctaaaactggaaGGGGGAAGCGGTGGAAGCGGGaggggag tgcaggtggaaaccatctccccaggagacgggcgcacctt ccccaagcgcggccagacctgcgtggtgcactacaccggg atgcttgaagatggaaagaaatttgattcctcccgggaca gaaacaagccctttaagtttatgctaggcaagcaggaggt gatccgaggctgggaagaaggggttgcccagatgagtgtg ggtcagagagccaaactgactatatctccagattatgcct atggtgccactgggcacccaggcatcatcccaccacatgc cactctcgtcttcgatgtggagcttctaaaactggaaGGT TCTaggggagtgcaggtggaaaccatctccccaggagacg ggcgcaccttccccaagcgcggccagacctgcgtggtgca ctacaccgggatgcttgaagatggaaagaaatttgattcc tcccgggacagaaacaagccctttaagtttatgctaggca agcaggaggtgatccgaggctgggaagaaggggttgccca gatgagtgtgggtcagagagccaaactgactatatctcca gattatgcctatggtgccactgggcacccaggcatcatcc caccacatgccactctcgtcttcgatgtggagcttctaaa actggaaGGATAA 10.
BPK3082: U6-Lb-crRNA-BsmBIcassette
U6 promoter: bold, Lb crRNA: italic,
BsmBI sites: lower case,
U6 terminator: italic and bold (SEQ ID NO: 57)

TGTACAAAAAAGCAGGCTTTAAAGGAACCAATTCAGTCGA

CTGGATCCGGTACCAAGGTCGGGCAGGAAGAGGGCCTATT

TCCCATGATTCCTTCATATTTGCATATACGATACAAGGCT

GTTAGAGAGATAATTAGAATTAATTTGACTGTAAACACAA

*AGATATTAGTACAAAATACGTGACGTAGAAAGTAATAATT*

*TCTTGGGTAGTTTGCAGTTTTAAAATTATGTTTTAAAATG*

*GACTATCATATGCTTACCGTAACTTGAAAGTATTTCGATT*

*TCTTGGCTTTATATATCTTGTGGAAAGGACGAAACACCGA*

*ATTTCTACTAAGTGTAGAT*GgagacgATTAATGcgtctcC

TTTTTTT

-continued

11. FIG. 2b_sequence
hU6 promoter: bold,
Lb crRNA direct repeats: italic,
crRNA1_HBB spacer sequence: lower case,
crRNA3_AR spacer sequence: lower case and bold,
crRNA1_NPY1R spacer sequence: lower case, bold and italic,
terminator: bold and italic (SEQ ID NO: 58)
GAGGGCCTATTTCCCATGATTCCTTCATATTTGCATATAC

GATACAAGGCTGTTAGAGAGATAATTAGAATTAATTTGAC

TGTAAACACAAAGATATTAGTACAAAATACGTGACGTAGA

AAGTAATAATTTCTTGGGTAGTTTGCAGTTTTAAAATTAT

GTTTTAAAATGGACTATCATATGCTTACCGTAACTTGAAA

GTATTTCGATTTCTTGGCTTTATATATCTTGTGGAAAGGA

CGAAACACCG*AATTTCTACTAAGTGTAGAT*tactgatggt atggggccaa*AATTTCTACTAAGTGTAGAT*ctctaggaac cctcagcccc*AATTTCTACTAAGTGTAGAT*aagcctcggg aaactgccct*AATTTCTACTAAGTGTAGAT*TTTTTTTT

REFERENCES

1. Maeder, M. L. et al. CRISPR RNA-guided activation of endogenous human genes. *Nat Methods* 10, 977-979 (2013).
2. Perez-Pinera, P. et al. RNA-guided gene activation by CRISPR-Cas9-based transcription factors. *Nat Methods* 10, 973-976 (2013).
3. Gilbert, L. A. et al. Genome-Scale CRISPR-Mediated Control of Gene Repression and Activation. *Cell* 159, 647-661 (2014).
4. Shen, J. P. et al. Combinatorial CRISPR-Cas9 screens for de novo mapping of genetic interactions. *Nature methods* (2017).
5. Chavez, A. et al. Comparison of Cas9 activators in multiple species. *Nature methods* 13, 563-567 (2016).
6. Zetsche, B., Volz, S. E. & Zhang, F. A split-Cas9 architecture for inducible genome editing and transcription modulation. *Nature biotechnology* 33, 139-142 (2015).
7. Guo, J. et al. An inducible CRISPR-ON system for controllable gene activation in human pluripotent stem cells. *Protein & cell* (2017).
8. Bao, Z., Jain, S., Jaroenpuntaruk, V. & Zhao, H. Orthogonal Genetic Regulation in Human Cells Using Chemically Induced CRISPR/Cas9 Activators. *ACS synthetic biology* (2017).
9. Polstein, L. R. & Gersbach, C. A. A light-inducible CRISPR-Cas9 system for control of endogenous gene activation. *Nature chemical biology* 11, 198-200 (2015).
10. Maji, B. et al. Multidimensional chemical control of CRISPR-Cas9. *Nature chemical biology* 13, 9-11 (2017).
11. Fonfara, I., Richter, H., Bratovic, M., Le Rhun, A. & Charpentier, E. The CRISPR-associated DNA-cleaving enzyme Cpf1 also processes precursor CRISPR RNA. *Nature* 532, 517-521 (2016).
12. Kim, S. K. et al. Efficient Transcriptional Gene Repression by Type V-A CRISPR-Cpf1 from *Eubacterium eligens*. *ACS synthetic biology* (2017).
13. Tang, X. et al. A CRISPR-Cpf1 system for efficient genome editing and transcriptional repression in plants. *Nature plants* 3, 17018 (2017).
14. Kleinstiver, B. P. et al. Genome-wide specificities of CRISPR-Cas Cpf1 nucleases in human cells. *Nature biotechnology* 34, 869-874 (2016).
15. Kim, D. et al. Genome-wide analysis reveals specificities of Cpf1 endonucleases in human cells. *Nature biotechnology* 34, 863-868 (2016).
16. Matis, C., Chomez, P., Picard, J. & Rezsohazy, R. Differential and opposed transcriptional effects of protein fusions containing the VP16 activation domain. *FEBS letters* 499, 92-96 (2001).
17. Lin, H., McGrath, J., Wang, P. & Lee, T. Cellular toxicity induced by SRF-mediated transcriptional squelching. *Toxicological sciences: an official journal of the Society of Toxicology* 96, 83-91 (2007).
18. Han, K. et al. Synergistic drug combinations for cancer identified in a CRISPR screen for pairwise genetic interactions. *Nature biotechnology* (2017).
19. Tsai, S. Q. et al. Dimeric CRISPR RNA-guided FokI nucleases for highly specific genome editing. *Nat Biotechnol* 32, 569-576 (2014).
20. Nissim, L., Perli, S. D., Fridkin, A., Perez-Pinera, P. & Lu, T. K. Multiplexed and programmable regulation of gene networks with an integrated RNA and CRISPR/Cas toolkit in human cells. *Molecular cell* 54, 698-710 (2014).
21. Xie, K., Minkenberg, B. & Yang, Y. Boosting CRISPR/Cas9 multiplex editing capability with the endogenous tRNA-processing system. *Proc Natl Acad Sci USA* 112, 3570-3575 (2015).
22. Xu, L., Zhao, L., Gao, Y., Xu, J. & Han, R. Empower multiplex cell and tissue-specific CRISPR-mediated gene manipulation with self-cleaving ribozymes and tRNA. *Nucleic Acids Res* (2016).
23. Kabadi, A. M., Ousterout, D. G., Hilton, I. B. & Gersbach, C. A. Multiplex CRISPR/Cas9-based genome engineering from a single lentiviral vector. *Nucleic Acids Res* 42, e147 (2014).
24. Wong, A. S. et al. Multiplexed barcoded CRISPR-Cas9 screening enabled by CombiGEM. *Proc Natl Acad Sci USA* 113, 2544-2549 (2016).
25. Adamson, B. et al. A Multiplexed Single-Cell CRISPR Screening Platform Enables Systematic Dissection of the Unfolded Protein Response. *Cell* 167, 1867-1882.e1821 (2016).
26. Wright, A. V., Nunez, J. K. & Doudna, J. A. Biology and Applications of CRISPR Systems. Harnessing Nature's Toolbox for Genome Engineering. *Cell* 164, 29-44 (2016).
27. Sander, J. D. & Joung, J. K. CRISPR-Cas systems for editing, regulating and targeting genomes. *Nat Biotechnol* 32, 347-355 (2014).
28. Hsu, P. D., Lander, E. S. & Zhang, F. Development and applications of CRISPR-Cas9 for genome engineering. *Cell* 157, 1262-1278 (2014).
29. Doudna, J. A. & Charpentier, E. Genome editing. The new frontier of genome engineering with CRISPR-Cas9. *Science* 346, 1258096 (2014).
30. Maeder, M. L. & Gersbach, C. A. Genome-editing Technologies for Gene and Cell Therapy. *Mol Ther* (2016).
31. Jinek, M. et al. A programmable dual-RNA-guided DNA endonuclease in adaptive bacterial immunity. *Science* 337, 816-821 (2012).
32. Deltcheva, E. et al. CRISPR RNA maturation by trans-encoded small RNA and host factor RNase III. *Nature* 471, 602-607 (2011).
33. Cong, L. et al. Multiplex genome engineering using CRISPR/Cas systems. *Science* 339, 819-823 (2013).

34. Mali, P. et al. RNA-guided human genome engineering via Cas9. *Science* 339, 823-826 (2013).
35. Jinek, M. et al. RNA-programmed genome editing in human cells. *Elife* 2, e00471 (2013).
36. Tsai, S. Q. et al. GUIDE-seq enables genome-wide profiling of off-target cleavage by CRISPR-Cas nucleases. *Nat Biotechnol* 33, 187-197 (2015).
37. Frock, R. L. et al. Genome-wide detection of DNA double-stranded breaks induced by engineered nucleases. *Nat Biotechnol* 33, 179-186 (2015).
38. Wang, X. et al. Unbiased detection of off-target cleavage by CRISPR-Cas9 and TALENs using integrase-defective lentiviral vectors. *Nat Biotechnol* 33, 175-178 (2015).
39. Kim, D. et al. Digenome-seq: genome-wide profiling of CRISPR-Cas9 off-target effects in human cells. *Nat Methods* 12, 237-243, 231 p following 243 (2015).
40. Kleinstiver, B. P. et al. High-fidelity CRISPR-Cas9 nucleases with no detectable genome-wide off-target effects. *Nature* 529, 490-495 (2016).
41. Slaymaker, I. M. et al. Rationally engineered Cas9 nucleases with improved specificity. *Science* 351, 84-88 (2016).
42. Schunder, E., Rydzewski, K., Grunow, R. & Heuner, K. First indication for a functional CRISPR/Cas system in *Francisella tularensis*. *Int J Med Microbiol* 303, 51-60 (2013).
43. Makarova, K. S. et al. An updated evolutionary classification of CRISPR-Cas systems. *Nat Rev Microbiol* 13, 722-736 (2015).
44. Zetsche, B. et al. Cpf1 Is a Single RNA-Guided Endonuclease of a Class 2 CRISPR-Cas System. *Cell* 163, 759-771 (2015).
45. Fagerlund, R. D., Staals, R. H. & Fineran, P. C. The Cpf1 CRISPR-Cas protein expands genome-editing tools. *Genome Biol* 16, 251 (2015).
46. Chavez, A. et al. Highly efficient Cas9-mediated transcriptional programming. *Nature methods* 12, 326-328 (2015).
47. Konermann, S. et al. Genome-scale transcriptional activation by an engineered CRISPR-Cas9 complex. *Nature* 517, 583-588 (2015).
48. Rivera, V. M., Berk, L. & Clackson, T. Dimerizer-mediated regulation of gene expression in vivo. *Cold Spring Harbor protocols* 2012, 821-824 (2012).
49. Zetsche, B. et al. Multiplex gene editing by CRISPR-Cpf1 using a single crRNA array. *Nature biotechnology* 35, 31-34 (2017).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing expression of a target gene in a cell, the method comprising contacting the cell with, or expressing in the cell: (a) a first fusion protein comprising a catalytically inactive Lachnospiraceae bacterium ND2006 Cpf1 (dLbCpf1) fused to more than one first dimerization domains, and (b) a second fusion protein comprising at least one activation domain fused to a second dimerization domain that dimerizes with at least one of the first dimerization domains in the first fusion protein in the presence of a dimerizing agent, wherein the first and second dimerization domains are rapamycin analog A/C heterodimerizer DmrA or DmrC, and at least one crRNA that directs the second fusion protein to a regulatory region of the target gene.

2. The method of claim 1, wherein (i) the first dimerization domain in the first fusion protein is DmrA, and the second dimerization domain in the second fusion protein is DmrC, or (ii) the first dimerization domain in the first fusion protein is DmrC, and the second dimerization domain in the second fusion protein is DmrA.

3. The method of claim 1, wherein the activation domain is a transcriptional activation domain from herpes simplex viral protein 16 (VP64), Epstein-Barr virus R transactivator (Rta), p65 domain from cellular transcription factor NF-κB (NF-κB p65), or a tripartite effector composed of VP64, p65, and Rta (VPR).

4. The method of claim 1, further comprising an intervening linker between each of the activation domain(s) or the second dimerization domain.

5. The method of claim 1, wherein the first fusion protein is fused to two, three or four first dimerization domains.

6. The method of claim 1, wherein the cell is a mammalian cell.

7. The method of claim 6, wherein the mammalian cell is a human cell.

8. The method of claim 1, wherein the regulatory region is a promoter region.

* * * * *

SEQUENCE LISTING

```
Sequence total quantity: 58
SEQ ID NO: 1           moltype = AA  length = 1246
FEATURE                Location/Qualifiers
source                 1..1246
                       mol_type = protein
                       note = Lachnospiraceae bacterium
                       organism = unidentified
SEQUENCE: 1
MLKNVGIDRL DVEKGRKNMS KLEKFTNCYS LSKTLRFKAI PVGKTQENID NKRLLVEDEK    60
RAEDYKGVKK LLDRYYLSFI NDVLHSIKLK NLNNYISLFR KKTRTEKENK ELENLEINLR   120
KEIAKAFKGN EGYKSLFKKD IIETILPEFL DDKDEIALVN SFNGFTTAFT GFFDNRENMF   180
SEEAKSTSIA FRCINENLTR YISNMDIFEK VDAIFDKHEV QEIKEKILNS DYDVEDFFEG   240
EFFNFVLTQE GIDVYNAIIG GFVTESGEKI KGLNEYINLY NQKTKQKLPK FKPLYKQVLS   300
DRESLSFYGE GYTSDEEVLE VFRNTLNKNS EIFSSIKKLE KLFKNFDEYS SAGIFVKNGP   360
AISTISKDIF GEWNVIRDKW NAEYDDIHLK KKAVVTEKYE DDRRKSFKKI GSFSLEQLQE   420
YADADLSVVE KLKEIIIQKV DEIYKVYGSS EKLFDADFVL EKSLKKNDAV VAIMKDLLDS   480
VKSFENYIKA FFGEGKETNR DESFYGDFVL AYDILLKVDH IYDAIRNYVT QKPYSKDKFK   540
LYFQNPQFMG GWDKDKETDY RATILRYGSK YYLAIMDKKY AKCLQKIDKD DVNGNYEKIN   600
YKLLPGPNKM LPKVFFSKKW MAYYNPSEDI QKIYKNGTFK KGDMFNLNDC HKLIDFFKDS   660
ISRYPKWSNA YDFNFSETEK YKDIAGFYRE VEEQGYKVSF ESASKKEVDK LVEEGKLYMF   720
QIYNKDFSDK SHGTPNLHTM YFKLLFDENN HGQIRLSGGA ELFMRRASLK KEELVVHPAN   780
SPIANKNPDN PKKTTTLSYD VYKDKRFSED QYELHIPIAI NKCPKNIFKI NTEVRVLLKH   840
DDNPYVIGID RGERNLLYIV VVDGKGNIVE QYSLNEIINN FNGIRIKTDY HSLLDKKEKE   900
RFEARQNWTS IENIKELKAG YISQVVHKIC ELVEKYDAVI ALEDLNSGFK NSRVKVEKQV   960
YQKFEKMLID KLNYMVDKKS NPCATGGALK GYQITNKFES FKSMSTQNGF IFYIPAWLTS  1020
KIDPSTGFVN LLKTKYTSIA DSKKFISSFD RIMYVPEEDL FEFALDYKNF SRTDADYIKK  1080
WKLYSYGNRI RIFRNPKKNN VFDWEEVCLT SAYKELFNKY GINYQQGDIR ALLCEQSDKA  1140
FYSSFMALMS LMLQMRNSIT GRTDVDFLIS PVKNSDGIFY DSRNYEAQEN AILPKNADAN  1200
GAYNIARKVL WAIGQFKKAE DEKLDKVKIA ISNKEWLEYA QTSVKH             1246

SEQ ID NO: 2           moltype = AA  length = 1228
FEATURE                Location/Qualifiers
source                 1..1228
                       mol_type = protein
                       note = Lachnospiraceae bacterium
                       organism = unidentified
SEQUENCE: 2
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
```

```
IGGFVTESGE KIKGLNEYIN LYNQKTKQKL PKFKPLYKQV LSDRESLSFY GEGYTSDEEV    300
LEVFRNTLNK NSEIFSSIKK LEKLFKNFDE YSSAGIFVKN GPAISTISKD IFGEWNVIRD    360
KWNAEYDDIH LKKKAVVTEK YEDDRRKSFK KIGSFSLEQL QEYADADLSV VEKLKEIIIQ    420
KVDEIYKVYG SSEKLFDADF VLEKSLKKND AVVAIMKDLL DSVKSFENYI KAFFGEGKET    480
NRDESFYGDF VLAYDILLKV DHIYDAIRNY VTQKPYSKDK FKLYFQNPQF MGGWDKDKET    540
DYRATILRYG SKYYLAIMDK KYAKCLQKID KDDVNGNYEK INYKLLPGPN KMLPKVFFSK    600
KWMAYYNPSE DIQKIYKNGT FKKGDMFNLN DCHKLIDFFK DSISRYPKWS NAYDFNFSET    660
EKYKDIAGFY REVEEQGYKV SFESASKKEV DKLVEEGKLY MFQIYNKDFS DKSHGTPNLH    720
TMYFKLLFDE NNHGQIRLSG GAELFMRRAS LKKEELVVHP ANSPIANKNP DNPKKTTTLS    780
YDVYKDKRFS EDQYELHIPI AINKCPKNIF KINTEVRVLL KHDDNPYVIG IDRGERNLLY    840
IVVVDGKGNI VEQYSLNEII NNFNGIRIKT DYHSLLDKKE KERFEARQNW TSIENIKELK    900
AGYISQVVHK ICELVEKYDA VIALEDLNSG FKNSRVKVEK QVYQKFEKML IDKLNYMVDK    960
KSNPCATGGA LKGYQITNKF ESFKSMSTQN GFIFYIPAWL TSKIDPSTGF VNLLKTKYTS   1020
IADSKKFISS FDRIMYVPEE DLFEFALDYK NFSRTDADYI KKWKLYSYGN RIRIFRNPKK   1080
NNVFDWEEVC LTSAYKELFN KYGINYQQGD IRALLCEQSD KAFYSSFMAL MSLMLQMRNS   1140
ITGRTDVDFL ISPVKNSDGI FYDSRNYEAQ ENAILPKNAD ANGAYNIARK VLWAIGQFKK   1200
AEDEKLDKVK IAISNKEWLE YAQTSVKH                                     1228

SEQ ID NO: 3           moltype = AA   length = 4
FEATURE                Location/Qualifiers
REGION                 1..4
                       note = linker peptide
source                 1..4
                       mol_type = protein
                       organism = synthetic construct
SEQUENCE: 3
GGGS                                                                  4

SEQ ID NO: 4           moltype = AA   length = 5
FEATURE                Location/Qualifiers
REGION                 1..5
                       note = linker peptide
source                 1..5
                       mol_type = protein
                       organism = synthetic construct
SEQUENCE: 4
GGGGS                                                                 5

SEQ ID NO: 5           moltype = AA   length = 7
FEATURE                Location/Qualifiers
REGION                 1..7
                       note = SV40 large T antigen NLS
source                 1..7
                       mol_type = protein
                       organism = synthetic construct
SEQUENCE: 5
PKKKRRV                                                               7

SEQ ID NO: 6           moltype = AA   length = 16
FEATURE                Location/Qualifiers
REGION                 1..16
                       note = nucleoplasmin NLS
source                 1..16
                       mol_type = protein
                       organism = synthetic construct
SEQUENCE: 6
KRPAATKKAG QAKKKK                                                    16

SEQ ID NO: 7           moltype = DNA  length = 337
FEATURE                Location/Qualifiers
misc_feature           1..337
                       note = nucleic acid encoding a plurality of Cpf1 gRNAs
source                 1..337
                       mol_type = other DNA
                       organism = synthetic construct
SEQUENCE: 7
gagggcctat ttcccatgat tccttcatat ttgcatatac gatacaaggc tgttagagag     60
ataattagaa ttaatttgac tgtaaacaca aagatattag tacaaaatac gtgacgtaga    120
aagtaataat ttcttgggta gtttgcagtt ttaaaattat gttttaaaat ggactatcat    180
atgcttaccg taacttgaaa gtatttcgat ttcttggctt tatatatctt gtggaaagga    240
cgaaacaccg aatttctact aagtgtagat aatttctact aagtgtagat aatttctact    300
aagtgtagat aatttctact aagtgtagat tttttttt                            337

SEQ ID NO: 8           moltype = DNA  length = 25
FEATURE                Location/Qualifiers
misc_feature           1..25
                       note = Cpf1 crRNA HBB_ Multiplexed, pair 1, top
```

```
source                  1..25
                        mol_type = other DNA
                        organism = synthetic construct
SEQUENCE: 8
agattactga tggtatgggg ccaaa                                              25

SEQ ID NO: 9            moltype = DNA   length = 31
FEATURE                 Location/Qualifiers
misc_feature            1..31
                        note = Cpf1 crRNA HBB_ Multiplexed, pair 1, bottom
source                  1..31
                        mol_type = other DNA
                        organism = synthetic construct
SEQUENCE: 9
tagtagaaat tttggcccca taccatcagt a                                       31

SEQ ID NO: 10           moltype = DNA   length = 51
FEATURE                 Location/Qualifiers
misc_feature            1..51
                        note = Cpf1 crRNA HBB_ Multiplexed, pair 2, top
source                  1..51
                        mol_type = other DNA
                        organism = synthetic construct
SEQUENCE: 10
atttctacta agtgtagata agtccaactc ctaagccaga atttctacta a                 51

SEQ ID NO: 11           moltype = DNA   length = 49
FEATURE                 Location/Qualifiers
misc_feature            1..49
                        note = Cpf1 crRNA HBB_ Multiplexed, pair 2, bottom
source                  1..49
                        mol_type = other DNA
                        organism = synthetic construct
SEQUENCE: 11
atctacactt agtagaaatt ctggcttagg agttggactt atctacact                    49

SEQ ID NO: 12           moltype = DNA   length = 56
FEATURE                 Location/Qualifiers
misc_feature            1..56
                        note = Cpf1 crRNA HBB_ Multiplexed, pair 3, top
source                  1..56
                        mol_type = other DNA
                        organism = synthetic construct
SEQUENCE: 12
gtgtagatca agtgtattta cgtaatataa tttctactaa gtgtagattt ttttta            56

SEQ ID NO: 13           moltype = DNA   length = 52
FEATURE                 Location/Qualifiers
misc_feature            1..52
                        note = Cpf1 crRNA HBB_ Multiplexed, pair 3, bottom
source                  1..52
                        mol_type = other DNA
                        organism = synthetic construct
SEQUENCE: 13
agcttaaaaa aaatctacac ttagtagaaa ttatattacg taaatacact tg                52

SEQ ID NO: 14           moltype = DNA   length = 25
FEATURE                 Location/Qualifiers
misc_feature            1..25
                        note = Cpf1 crRNA AR_ Multiplexed, pair 1, top
source                  1..25
                        mol_type = other DNA
                        organism = synthetic construct
SEQUENCE: 14
agatagagtc tggatgagaa atgca                                              25

SEQ ID NO: 15           moltype = DNA   length = 31
FEATURE                 Location/Qualifiers
misc_feature            1..31
                        note = Cpf1 crRNA AR_ Multiplexed, pair 1, bottom
source                  1..31
                        mol_type = other DNA
                        organism = synthetic construct
SEQUENCE: 15
tagtagaaat tgcatttctc atccagactc t                                       31
```

```
SEQ ID NO: 16          moltype = DNA   length = 51
FEATURE                Location/Qualifiers
misc_feature           1..51
                       note = Cpf1 crRNA AR_ Multiplexed, pair 2, top
source                 1..51
                       mol_type = other DNA
                       organism = synthetic construct
SEQUENCE: 16
atttctacta agtgtagatt accctcttct ctgcctttca atttctacta a                 51

SEQ ID NO: 17          moltype = DNA   length = 49
FEATURE                Location/Qualifiers
misc_feature           1..49
                       note = Cpf1 crRNA AR_ Multiplexed, pair 2, bottom
source                 1..49
                       mol_type = other DNA
                       organism = synthetic construct
SEQUENCE: 17
atctacactt agtagaaatt gaaaggcaga gaagagggta atctacact                    49

SEQ ID NO: 18          moltype = DNA   length = 56
FEATURE                Location/Qualifiers
misc_feature           1..56
                       note = Cpf1 crRNA AR_ Multiplexed, pair 3, top
source                 1..56
                       mol_type = other DNA
                       organism = synthetic construct
SEQUENCE: 18
gtgtagatct ctaggaaccc tcagccccaa tttctactaa gtgtagattt tttta             56

SEQ ID NO: 19          moltype = DNA   length = 52
FEATURE                Location/Qualifiers
misc_feature           1..52
                       note = Cpf1 crRNA AR_ Multiplexed, pair 3, bottom
source                 1..52
                       mol_type = other DNA
                       organism = synthetic construct
SEQUENCE: 19
agcttaaaaa aaatctacac ttagtagaaa ttggggctga gggttcctag ag                52

SEQ ID NO: 20          moltype = DNA   length = 25
FEATURE                Location/Qualifiers
misc_feature           1..25
                       note = Cpf1 crRNA NPY1R_ Multiplexed, pair 1, top
source                 1..25
                       mol_type = other DNA
                       organism = synthetic construct
SEQUENCE: 20
agataagcct cgggaaactg cccta                                              25

SEQ ID NO: 21          moltype = DNA   length = 31
FEATURE                Location/Qualifiers
misc_feature           1..31
                       note = Cpf1 crRNA NPY1R_ Multiplexed, pair 1, bottom
source                 1..31
                       mol_type = other DNA
                       organism = synthetic construct
SEQUENCE: 21
tagtagaaat tagggcagtt tcccgaggct t                                       31

SEQ ID NO: 22          moltype = DNA   length = 51
FEATURE                Location/Qualifiers
misc_feature           1..51
                       note = Cpf1 crRNA NPY1R_ Multiplexed, pair 2, top
source                 1..51
                       mol_type = other DNA
                       organism = synthetic construct
SEQUENCE: 22
atttctacta agtgtagatt ttgtttgcag gtcagtgcca atttctacta a                 51

SEQ ID NO: 23          moltype = DNA   length = 49
FEATURE                Location/Qualifiers
misc_feature           1..49
                       note = Cpf1 crRNA NPY1R_ Multiplexed, pair 2, bottom
source                 1..49
                       mol_type = other DNA
                       organism = synthetic construct
```

```
SEQUENCE: 23
atctacactt agtagaaatt ggcactgacc tgcaaacaaa atctacact                49

SEQ ID NO: 24          moltype = DNA   length = 56
FEATURE                Location/Qualifiers
misc_feature           1..56
                       note = Cpf1 crRNA NPY1R_ Multiplexed, pair 3, top
source                 1..56
                       mol_type = other DNA
                       organism = synthetic construct
SEQUENCE: 24
gtgtagatgg ctggcgctcg agctctccaa tttctactaa gtgtagattt ttttta        56

SEQ ID NO: 25          moltype = DNA   length = 52
FEATURE                Location/Qualifiers
misc_feature           1..52
                       note = Cpf1 crRNA NPY1R_ Multiplexed, pair 3, bottom
source                 1..52
                       mol_type = other DNA
                       organism = synthetic construct
SEQUENCE: 25
agcttaaaaa aaatctacac ttagtagaaa ttggagagct cgagcgccag cc            52

SEQ ID NO: 26          moltype = DNA   length = 25
FEATURE                Location/Qualifiers
misc_feature           1..25
                       note = Cpf1 crRNA HBB_AR_NPY1R_Multiplexed, pair 1, top
source                 1..25
                       mol_type = other DNA
                       organism = synthetic construct
SEQUENCE: 26
agattactga tggtatgggg ccaaa                                          25

SEQ ID NO: 27          moltype = DNA   length = 31
FEATURE                Location/Qualifiers
misc_feature           1..31
                       note = Cpf1 crRNA HBB_AR_NPY1R_ Multiplexed, pair1, top
source                 1..31
                       mol_type = other DNA
                       organism = synthetic construct
SEQUENCE: 27
tagtagaaat tttggcccca taccatcagt a                                   31

SEQ ID NO: 28          moltype = DNA   length = 51
FEATURE                Location/Qualifiers
misc_feature           1..51
                       note = Cpf1 crRNA HBB_AR_NPY1R_Multiplexed pair2 top
source                 1..51
                       mol_type = other DNA
                       organism = synthetic construct
SEQUENCE: 28
atttctacta agtgtagatc tctaggaacc ctcagcccca atttctacta a             51

SEQ ID NO: 29          moltype = DNA   length = 49
FEATURE                Location/Qualifiers
misc_feature           1..49
                       note = Cpf1 crRNA HBB_AR_NPY1R_Multiplexed pair2 bottom
source                 1..49
                       mol_type = other DNA
                       organism = synthetic construct
SEQUENCE: 29
atctacactt agtagaaatt ggggctgagg gttcctagag atctacact                49

SEQ ID NO: 30          moltype = DNA   length = 56
FEATURE                Location/Qualifiers
misc_feature           1..56
                       note = Cpf1 crRNA HBB_AR_NPY1R_Multiplexed pair3 top
source                 1..56
                       mol_type = other DNA
                       organism = synthetic construct
SEQUENCE: 30
gtgtagataa gcctcgggaa actgccctaa tttctactaa gtgtagattt ttttta        56

SEQ ID NO: 31          moltype = DNA   length = 52
FEATURE                Location/Qualifiers
misc_feature           1..52
                       note = Cpf1 crRNA HBB_AR_NPY1R_Multiplexed pair3 bottom
```

```
source                  1..52
                        mol_type = other DNA
                        organism = synthetic construct
SEQUENCE: 31
agcttaaaaa aaatctacac ttagtagaaa ttagggcagt ttcccgaggc tt              52

SEQ ID NO: 32           moltype = DNA  length = 22
FEATURE                 Location/Qualifiers
misc_feature            1..22
                        note = RT-qPCR primer oET_173
source                  1..22
                        mol_type = other DNA
                        organism = synthetic construct
SEQUENCE: 32
atggtgagca gagtgcccta tc                                              22

SEQ ID NO: 33           moltype = DNA  length = 22
FEATURE                 Location/Qualifiers
misc_feature            1..22
                        note = RT-qPCR primer oET_174
source                  1..22
                        mol_type = other DNA
                        organism = synthetic construct
SEQUENCE: 33
atggtccctg gcagtctcca aa                                              22

SEQ ID NO: 34           moltype = DNA  length = 23
FEATURE                 Location/Qualifiers
misc_feature            1..23
                        note = RT-qPCR primer oET_175
source                  1..23
                        mol_type = other DNA
                        organism = synthetic construct
SEQUENCE: 34
ccatcggact ctcataggtt gtc                                             23

SEQ ID NO: 35           moltype = DNA  length = 24
FEATURE                 Location/Qualifiers
misc_feature            1..24
                        note = RT-qPCR primer oET_176
source                  1..24
                        mol_type = other DNA
                        organism = synthetic construct
SEQUENCE: 35
gacctgtact tattgtctct catc                                            24

SEQ ID NO: 36           moltype = DNA  length = 20
FEATURE                 Location/Qualifiers
misc_feature            1..20
                        note = RT-qPCR primer oET_225
source                  1..20
                        mol_type = other DNA
                        organism = synthetic construct
SEQUENCE: 36
gcacgtggat cctgagaact                                                 20

SEQ ID NO: 37           moltype = DNA  length = 21
FEATURE                 Location/Qualifiers
misc_feature            1..21
                        note = RT-qPCR primer oET_226
source                  1..21
                        mol_type = other DNA
                        organism = synthetic construct
SEQUENCE: 37
attggacagc aagaaagcga g                                               21

SEQ ID NO: 38           moltype = DNA  length = 20
FEATURE                 Location/Qualifiers
misc_feature            1..20
                        note = Lb crRNA direct repeat
source                  1..20
                        mol_type = other DNA
                        organism = synthetic construct
SEQUENCE: 38
aatttctact aagtgtagat                                                 20
```

```
SEQ ID NO: 39           moltype = DNA   length = 24
FEATURE                 Location/Qualifiers
misc_feature            1..24
                        note = Cpf1 crRNA HBB_P_1 guide
source                  1..24
                        mol_type = other DNA
                        organism = synthetic construct
SEQUENCE: 39
tttgtactga tggtatgggg ccaa                                                 24

SEQ ID NO: 40           moltype = DNA   length = 24
FEATURE                 Location/Qualifiers
misc_feature            1..24
                        note = Cpf1 crRNA HBB_P_2 guide
source                  1..24
                        mol_type = other DNA
                        organism = synthetic construct
SEQUENCE: 40
tttgaagtcc aactcctaag ccag                                                 24

SEQ ID NO: 41           moltype = DNA   length = 24
FEATURE                 Location/Qualifiers
misc_feature            1..24
                        note = Cpf1 crRNA HBB_P_3 guide
source                  1..24
                        mol_type = other DNA
                        organism = synthetic construct
SEQUENCE: 41
tttgcaagtg tatttacgta atat                                                 24

SEQ ID NO: 42           moltype = DNA   length = 24
FEATURE                 Location/Qualifiers
misc_feature            1..24
                        note = Cpf1 crRNA AR_P_1 guide
source                  1..24
                        mol_type = other DNA
                        organism = synthetic construct
SEQUENCE: 42
tttgagagtc tggatgagaa atgc                                                 24

SEQ ID NO: 43           moltype = DNA   length = 24
FEATURE                 Location/Qualifiers
misc_feature            1..24
                        note = Cpf1 crRNA AR_P_2 guide
source                  1..24
                        mol_type = other DNA
                        organism = synthetic construct
SEQUENCE: 43
tttctaccct cttctctgcc tttc                                                 24

SEQ ID NO: 44           moltype = DNA   length = 24
FEATURE                 Location/Qualifiers
misc_feature            1..24
                        note = Cpf1 crRNA AR_P_3 guide
source                  1..24
                        mol_type = other DNA
                        organism = synthetic construct
SEQUENCE: 44
tttgctctag gaaccctcag cccc                                                 24

SEQ ID NO: 45           moltype = DNA   length = 24
FEATURE                 Location/Qualifiers
misc_feature            1..24
                        note = Cpf1 crRNA NPY1R_P_1 guide
source                  1..24
                        mol_type = other DNA
                        organism = synthetic construct
SEQUENCE: 45
tttcaagcct cgggaaactg ccct                                                 24

SEQ ID NO: 46           moltype = DNA   length = 24
FEATURE                 Location/Qualifiers
misc_feature            1..24
                        note = Cpf1 crRNA NPY1R_P_2 guide
source                  1..24
                        mol_type = other DNA
                        organism = synthetic construct
```

```
SEQUENCE: 46
tttctttgtt tgcaggtcag tgcc                                           24

SEQ ID NO: 47           moltype = DNA  length = 24
FEATURE                 Location/Qualifiers
misc_feature            1..24
                        note = Cpf1 crRNA NPY1R_P_3 guide
source                  1..24
                        mol_type = other DNA
                        organism = synthetic construct
SEQUENCE: 47
tttgggctgg cgctcgagct ctcc                                           24

SEQ ID NO: 48           moltype = DNA  length = 3822
FEATURE                 Location/Qualifiers
misc_feature            1..3822
                        note = Human codon optimized dLbCpf1
source                  1..3822
                        mol_type = other DNA
                        organism = synthetic construct
SEQUENCE: 48
atgagcaagc tggagaagtt tacaaactgc tactccctgt ctaagaccct gaggttcaag    60
gccatccctg tgggcaagac ccaggagaac atcgacaata gcggctgct ggtggaggac    120
gagaagagag ccgaggatta aagggcgtg aagaagctgc tggatcgcta ctatctgtct    180
tttatcaacg acgtgctgca cagcatcaag ctgaagaatc tgaacaatta catcagcctg    240
ttccggaaga aaaccagaac cgagaaggag aataaggagc tggagatcaat              300
ctgcggaagc agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt gataagcac    600
gaggtgcagg agatcaagga agatcctg aacagcgact atgatgtgga ggattctttt    660
gagggcgagt tctttaactt tgtgctgaca caggagggca tcgacgtgta taacgccatc    720
atcgcggct tcgtgaccga gagcggcgag aagatcaagg gcctgaacga gtacatcaac    780
ctgtataatc agaaaaccaa gcagaagctg cctaagttta gccactgta taagcaggtg    840
ctgagcgatc gggagtctct gagccttac ggcgagggct atacatccga tgaggagtg    900
ctggaggtgt ttagaaacac cctgaacaag aacagcgaga tcttcagctc catcaagaag    960
ctggagaagc tgttcaagaa ttttgacgag tactctagcg ccggcatctt tgtgaagaac    1020
ggccccgcca tcagcacaat ctccaaggat atcttcggcg agtggaacgt gatccggaac    1080
aagtgaatg ccgagtatga cgatatccac ctgaagaaga aggccgtggt gaccgagaag    1140
tacgaggacg atcggagaaa gtccttcaag aagatcggc cttttctct ggagcagctg    1200
caggagtacg ccgacgccga tctgtctgtg gtggagaagc tgaaggagat catcatccag    1260
aaggtggata gatctacaa ggtgtatggc tcctctgaga agctgttcga cgcccgattct    1320
gtgctggaga gagcctgaa gaagaacgac gccgtggtgg ccatcatgaa ggacctgctg    1380
gattctgtga gagcttcga gaattacatc aaggccttct tggcgaggg caaggagaca    1440
aacagggacg agtccttcta tggcgatttt gtgctggcct acgacatcct gctgaaggtg    1500
gaccacatct acgatgccat ccgcaattat gtgacccaga agccctactc taaggataag    1560
ttcaagctgt attttcagaa ccctcagttc atgggcggct gggacaagga taaggagaca    1620
gactatcggg ccaccatcct gagatacggc tccaagtact atctggccat catggataag    1680
aagtacgcca agtgcctgca gaagatcgac aaggacgatg tgaacggcaa ttacgagaag    1740
atcaactata gctgctgcc cggccctaat aagatgctgc caaaggtgtt cttttctaag    1800
aagtggatgg cctactataa ccccagcgag gacatccaga gatctacaa gaatggcaca    1860
ttcaagaagg gcgatatgtt taacctgaat gactgtcaca gctgatcga cttctttaag    1920
gatagcatct cccggtatcc aaagtggtcc aatgcctacg atttcaactt ttctgagaca    1980
gagaagtata aggacatcgc cggcttttac agagaggtgg aggagcaggg ctataaggtg    2040
agcttcgagt ctgccagcaa gaaggaggtg gataagctgg tggaggaggg caagctgtat    2100
atgttccaga tctataacaa ggacttttcc gataagtctc acggcacacc caatctgcac    2160
accatgtact tcaagctgct gttttgacgag aacaatcacg acagatcag gctgagcgga    2220
ggagcagagc tgttcatgag gcgcgcctcc ctgaagaagg aggagctggt ggtgcaccca    2280
gccaactccc ctatcgccaa caagaatcca gataatccac agaaaaccac aacccctgtcc    2340
tacgacgtgt ataaggataa gaggttttct gaggaccagt acgagctgca catcccaatc    2400
gccatcaata agtgccccaa gaacatcttc aagatcaata cagaggtgcg cgtgctgctg    2460
aagcacgacg ataaccccta tgtgatcggc atcgccaggg gcgagcgcaa tctgctgtat    2520
atcgtggtg tggacggcca gggcaacatc tggagcagt attccctgaa cgagatcatc    2580
aacaacttca cggcatcag gatcaagaca gattaccact ctctgctgga caagaaggag    2640
aaggagaggt tcgaggcccg ccagaactgg acctccatcg agaatatcaa ggagctgaag    2700
gccggctata tctctcaggt ggtgcacaag atctgcgagc tggtgagaa gtacgatgcc    2760
gtgatcgccc tggaggacct gaactctggc tttaagaata gccgcgtgaa ggtggagaag    2820
caggtctatc agaagttcga gaagatgctg atcgataagc taactacat ggtggacaag    2880
aagtctaatc cttgtgcaac aggcggcgcc ctgaagggct atcagatcac caataagttc    2940
gagagcttta gtccatgtc tacccagaac ggcttcatct tttacatccc tgcctggctg    3000
acatccaaga tcgatccatc taccggcttt gtgaacctgc tgaaaccaa gtataccagc    3060
atcgccgatt ccaagaagtt catcagctcc tttgacagga tcatgtacgt gcccgaggag    3120
gatcgtgttc gagttttgccct ggactataag aacttctctc gcacagacgc cgattacatc    3180
aagaagtgga agctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360
aaggccttca ctctagcttt tatggcctg atgagcctga tgctgcagat gcggaacagc    3420
atcacaggcc gcaccgacgt ggattttctg atcagccctg tgaagaactc cgacggcatc    3480
```

```
ttctacgata gccggaacta tgaggcccag gagaatgcca tcctgccaaa gaacgccgac   3540
gccaatggcg cctataacat cgccagaaag gtgctgtggg ccatcggcca gttcaagaag   3600
gccgaggacg agaagctgga taaggtgaag atcgccatct ctaacaagga gtggctggag   3660
tacgcccaga ccagcgtgaa gcacaaaagg ccggcggcca cgaaaaaggc cggccaggca   3720
aaaaagaaaa agggatccta cccatacgat gttccagatt acgcttatcc ctacgacgtg   3780
cctgattatg catacccata tgatgtcccc gactatgcct aa                      3822

SEQ ID NO: 49           moltype = DNA   length = 1227
FEATURE                 Location/Qualifiers
misc_feature            1..1227
                        note = BPK1169: CAG-DmrC-NLS-FLAG-P65
source                  1..1227
                        mol_type = other DNA
                        organism = synthetic construct
SEQUENCE: 49
atgggatcca gaatcctctg gcatgagatg tggcatgaag gcctggaaga ggcatctcgt    60
ttgtactttg gggaaaggaa cgtgaaaggc atgtttgagg tgctggagcc cttgcatgct   120
atgatggaac ggggacccca gactctgaag gaaacatcct ttaatcaggc ctatggtcga   180
gatttaatgg aggcccaaga gtggtgcagg aagtacatga aatcaggaa tgtcaaggac    240
ctcctccaag cctgggacct ctattatcat gtgttccgac gaatctcaaa gggcggcgga   300
tcccccaaga agaagaggaa agtctcgagc gactacaaaa accatgacgg tgattataaa   360
gatcatgaca tcgattacaa ggatgacgat gacaaggctg cagaggcggc tggaagcggg   420
atggagttcc agtacctgcc agatacagac gatcgtcacc ggattgagga gaaacgtaaa   480
aggacatatg agaccttcaa gagcatcatg aagaagagtc ctttcagcgg acccaccgac   540
ccccggcctc cacctcgacg cattgctgtg ccttcccgca gctcagcttc tgtccccaag   600
ccagcaccc agccctatcc cttttacgtca tccctgagca ccatcaacta tgatgagttt   660
cccaccatgg tgtttcctc tgggcagatc agccaggcct cggccttggc cccggcccct   720
ccccaagtcc tgcccaggc tccagccct gccctgctc cagccatggt atcagctctg    780
gcccaggccc cagcccctgt cccagtccta gcccaggcc ctcctcaggc tgtggcccca    840
cctgcccca agcccacccca ggctggggaa ggaacgctgt cagaggccct gctgcagctg    900
cagtttgatg atgaagacct gggggccttg cttggcaaca gcacagaccc agctgtgttc    960
acagacctgg catccgtcga taactccgag tttcagcagc tgctgaacca gggcatacct   1020
gtggcccccc acacaactga gcccatgctg atggagtacc ctgaggctat aactcgccta   1080
gtgacagggg cccagaggcc ccccgaccca gctcctgctc cactggggg cccggggctc   1140
cccaatggcc tcctttcagg agatgaagac ttctcctcca ttgcggacat ggactttcta   1200
gccctgctga gtcagatcag ctcttaa                                       1227

SEQ ID NO: 50           moltype = DNA   length = 2016
FEATURE                 Location/Qualifiers
misc_feature            1..2016
                        note = MMW948: CAG-DmrC-NLS-FLAG-VPR
source                  1..2016
                        mol_type = other DNA
                        organism = synthetic construct
SEQUENCE: 50
atgggatcca gaatcctctg gcatgagatg tggcatgaag gcctggaaga ggcatctcgt    60
ttgtactttg gggaaaggaa cgtgaaaggc atgtttgagg tgctggagcc cttgcatgct   120
atgatggaac ggggacccca gactctgaag gaaacatcct ttaatcaggc ctatggtcga   180
gatttaatgg aggcccaaga gtggtgcagg aagtacatga aatcaggaa tgtcaaggac    240
ctcctccaag cctgggacct ctattatcat gtgttccgac gaatctcaaa gggcggcgga   300
tcccccaaga agaagaggaa agtctcgagc gactacaaaa accatgacgg tgattataaa   360
gatcatgaca tcgattacaa ggatgacgat gacaaggctg caggaggcgg tggaagcggg   420
tcggaggcca gcggttccgg acgggctgac gcattggacg attttgatct ggatatgctg   480
ggaagtgacg ccctcgatga ttttgacctt gacatgcttg gttcggatgc ccttgatgac   540
tttgacctgg acatgctcgg cagtgacgcc ctgatgatt cgacctgga catgctgatt   600
aactctagaa gttccggatc tccgaaaaag aaacgcaaag ttggtagcca gtacctgccc   660
gacaccgacg accggcaccg gatcgaggaa agcggaagc ggacctacga cattcaag    720
agcatcatga agaagtcccc cttcagcggc cccaccgacc ctagacctcc acctagaaga   780
atcgccgtgc ccagcagatc cagcgccagc gtgccaaaac ctgccccca gccttacccc   840
ttcaccagca gcctgagcac catcaactac gacgagttcc tactaatggt gttcccagc   900
ggccagatct ctcaggcct tgctctggct ccagcccct ctcaggtgct gcctcaggct    960
cctgctcctg caccagctcc agccatggtg tctgcactgg ctcaggacc agcaccgtg   1020
cctgtgctgg ctcctggacc tccacaggct gtggctccac cagccctaa acctacacag   1080
gccggcgagg gcacactgtc tgaagctctg ctgcagctgc agtttgacga cgaggatctg   1140
ggagccctgc tggaaacag caccgatcct gccgtgttca ccgacctggc cagcgtggac   1200
aacagcgagt tccagcagct gctgaaccag ggcatccctg tggcccctca caccaccgag   1260
cccatgctga tggaataccc cgaggccatc acccggctcg tgacaggcgc tcagaggcct   1320
cctgatcag ctcctgcccc tctgggagca ccaggcctgc ctaatggact gctgtctggc   1380
gacgaggact ccagctcctt cgccgatatg atttctcag ccttgctggg ctctggcac   1440
ggcagccggg attccaggga agggatgttt ttgccgaagc tgaggccgg ctccgctatt   1500
agtgacgtgt ttgagggccg cgaggtgtgc cagccaaaac gaatccggcc atttcatcct   1560
ccaggaagtc catgggccaa ccgcccactc ccgccagcc tcgcaccaac caaccggt   1620
ccagtacatg agccagtcgg gtcactgacc ccggcaccag tccctcagcc actggatcca   1680
gcgcccgcag tgactcccga ggccagtcac tgttggagga tccgatga agagct       1740
caggctgtca aagcccttcg ggagatggcc gatactgtga ttcccagaa ggaagaggct   1800
gcaatctgtg gccaaatgga ccttttccat ccgccccaa ggggccatct ggatgagctg   1860
acaaccac ttgagtccat gaccgaggat ctgaactgg actcaccct gaccccgaa      1920
ttgaacgaga ttctggatac cttcctgaac gacgagtgcc tcttgcatgc catgcatatc   1980
agcacaggac tgtccatctt cgacacatct ctgttt                            2016
```

| SEQ ID NO: 51 | moltype = DNA length = 4632 |
|---|---|
| FEATURE | Location/Qualifiers |
| misc_feature | 1..4632 |
| | note = JG1202: CAG-human dLbCpf1(D832A)-NLS-3xHA-P65 |
| source | 1..4632 |
| | mol_type = other DNA |
| | organism = synthetic construct |

SEQUENCE: 51

```
atgagcaagc tggagaagtt tacaaactgc tactccctgt ctaagaccct gaggttcaag    60
gccatccctg tgggcaagac ccaggagaac atcgacaata gcggctgct ggtgagggac   120
gagaagagag ccgaggatta aagggcgtg aagaagctgc tggatcgcta ctatctgtct   180
tttatcaacg acgtgctgca cagcatcaag ctgaagaatc tgaacaatta catcagcctg   240
ttccggaaga aaaccagaac cgagaaggag aataaggagc tggagaacct ggagatcaat   300
ctgcggaagg agatcgccaa ggccttcaag ggcaacgagg gctacaagtc cctgtttaag   360
aaggatatca tcgagacaat cctgccagag ttcctggacg ataaggacga gatcgccctg   420
gtgaacagct tcaatggctt taccacagcc ttcaccggct tctttgataa cagagagaat   480
atgttttccg aggaggccaa gagcacatcc atcgccttca ggtgtatcaa cgagaatctg   540
acccgctaca tctctaatat ggacatcttc gagaaggtgg acgccatctt tgataagcac   600
gaggtgcagg agatcaagga agatcctc aacagcgact atgatgtgga ggatttcttt   660
gagggcgagt tcttaacct tgtgctgaca caggagggca tcgacgtgta acgccatc    720
atcggcggct tcgtgaccga gagcggcgag aagatcaagg gcctgaacga gtacatcaac   780
ctgtataatc agaaaaccaa gcagaagctg cctaagttta gccactgta taagcaggtg   840
ctgagcgatc gggagtctct gagcttctac ggcgagggct acatccga tgaggaggtg   900
ctggaggtgt tagaaacac cctgaacaag aacagcgaga tcttcagctc catcaagaag   960
ctggagaagc tgttcaagaa ttttgacgag tactctaccc ccggcatctt tgtgaagaac  1020
ggccccgcca tcagcacaat ctccaaggat atcttcggcg agtggaacgt gatccggac  1080
aagtggaatg ccgagtatga cgatatccac ctgaagaaga aggccgtggt gaccgagaag  1140
tacgaggacg atcggagaaa gtccttcaag aagatcggc ccttttctct ggagcagctg  1200
caggagacag ccgacgccca tctgtctgtg gtggagagc tgaaggagat catcatccag  1260
aaggtggatg atctacaa ggtgtatggc tcctctgaga gctgttcga cgccgatttt  1320
gtgctggaga gagcctgaa gaagaacgac gccgtggtgg ccatcatgaa ggacctgctg  1380
gattctgtga gagcttcga gaattacatc aaggccttct tggcgaggg caaggagaca  1440
aacagggacg agtccttcta tggcgatttt gtgctggcct acgacatcct gctgaaggtg  1500
gaccacatct acgatgccat ccgcaattat gtgacccaga gccctacte taaggataag  1560
ttcaagctgt attttcagaa ccctcagtte atgggcggct gggacaagga taggagaca  1620
gactatcggg ccaccatcct gagatacggc tccaagtact atctggccat catggataag  1680
aagtacgcca agtgcctgca gaagatcgac aaggacgatg tgaacggcaa ttacgagaag  1740
atcaactata gctgctgcc cggccctaat aagatgctgc caaaggtgtt cttttctaag  1800
aagtggatgg cctactataa ccccagcgag gacatccaga gatctacaa gaatggcaca  1860
ttcaagaagg cgatatgtt taacctgaat gactgtcaca gctgatcga cttctttaag  1920
gatagcatct cccggtatcc aaagtggtcc aatgcctacg atttcaactt ttctgagaca  1980
gagaagtata aggacatcgc cggcttttac agagaggtgg aggagcaggg ctataaggtg  2040
agcttcgagt ctgccagcaa gaaggaggtg gataagctgg tggaggaggg caagctgtat  2100
atgttccaga tctataacaa ggacttttcc gataagtctc acggcacacc caatctgcac  2160
accatgtact tcaagctgct gtttgacgag aacaatcacg acagatcag gctgagcgga  2220
ggagcagagc tgttcatgag gcgcgccctc ctgaagaggg aggagctggt ggtgcaccca  2280
gccaactccc ctatcgccaa caagaatcca gataatccca agaaaaccac aacctgtcc  2340
tacgacgtgt ataaggataa gaggttttct gaggaccagt acgagctgca catcccaatc  2400
gccatcaata gtgccccaa gaacatcttc aagatcaata cagaggtgcg cgtgctgctg  2460
aagcacgaca taaccccta tgtgatcggc atcgccaggg cgcgagcgca tctgctgtat  2520
atcgtggtgg tggacggcaa gggcaacatc gtggagcagt attccctgaa cgagatcatc  2580
aacaacttca acggcatcag gatcaagaca gattaccact ctctgctgga caagaaggag  2640
aaggagaggt cgaggcccg ccagaactgg acctccatcg agaatatcaa ggagctgaag  2700
gccggctata tctctcaggt ggtgcacaag atctgcgagc tggtggagaa gtacgatgcc  2760
gtgatcgccc tggaggacct gaactctggc tttaagaata gccgcgtgaa ggtggagaag  2820
caggtgtatc agaagttcga gaagatgctg atcgataagc tgaactacat ggtggacaag  2880
aagtctaatc cttgtgcaac aggcggcgcc ctgaagggct atcagatcac caataagttc  2940
gagagctttta agtccatgtc tacccagaac ggcttcatct tttacatccc tgcctggctg  3000
acatccaaga tcgatccatc taccggcttt gtgaacctgc tgaaaaccaa gtataccagc  3060
atcgccgatt ccaagaagtt catcagctcc tttgacagga tcatgtacgt gcccgaggag  3120
gatctgttcg agtttgccct ggactataag aacttctctc gcacagacgc cgattacatc  3180
aagaagtgga agctgtactc ctacggcaac cggatcagaa tcttccggaa tcctaagaag  3240
aacaacgtgt tcgactggga ggaggtgtgc ctgaccagcc cctataagga gctgttcaac  3300
aagtacggca tcaattatca gcagggcgat atcagagccc tgctgtgcga cagtccgac  3360
aaggccttct actctagctt tatggccctg atgagcctga tgctgcagat gcggaacagc  3420
atcacaggcc gcaccgacgt ggattttctg atcagccctg tgaagaactc cgacggcatc  3480
ttctcgata gccggaacta tgaggcccag gagaatgcca tcctgccaaa gaacgccgac  3540
gccaatggcg cctataacat cgccagaaag gtgctgtggg ccatcggca gttcaagaag  3600
gccgaggacg agaagctgga taaggtgaag atcgccatct taacaagga gtggctggaa  3660
tacgcccaga ccagcgtgaa gcacaaaagg ccggcggcca cgaaaaaggc cggcaggca  3720
aaaaagaaaa agggatccta cccatacgat gttccagatt acgcttatcc ctacgacgtg  3780
cctgattatg cataccccata tgatgtcccc gactatgcgg aagcatggga gttccagtac  3840
ctgccagata cagacgatcg tcaccggatt gaggagaaac gtaaaaggac atatgagacc  3900
ttcaagagca tcatgaagaa gagtccttc agcggaccca ccgaccccg gcctccacct  3960
cgacgcattg ctgtgccttc ccgcagctca gcttctgtcc caagccagc accccagccc  4020
tatcccttta cgtcatccct gagcaccatc aactatgatg agtttcccac catggtgttt  4080
ccttctgggc agatcagcca ggcctcggcc ttggccccgg ccctcccca gtcctgccc  4140
caggctccag ccccctgcccc tgctccagcc atggtatcag ctctgcccca ggcccagcc  4200
```

-continued

```
cctgtcccag tcctagcccc aggccctcct caggctgtgg ccccacctgc ccccaagccc    4260
acccaggctg gggaaggaac gctgtcagag gccctgctgc agctgcagtt tgatgatgaa    4320
gacctggggg ccttgcttgg caacagcaca gacccagctg tgttcacaga cctggcatcc    4380
gtcgataact ccgagtttca gcagctgctg aaccagggca tacctgtggc cccccacaca    4440
actgagccca tgctgatgga gtaccctgag gctataactc gcctagtgac aggggcccaa    4500
aggcccccg acccagctcc tgctccactg ggggccccgg ggctcccaa tggcctcctt      4560
tcaggagatg aagacttctc ctccattgcg gacatggact tctcagccct gctgagtcag    4620
atcagctctt aa                                                        4632
```

```
SEQ ID NO: 52            moltype = DNA   length = 5418
FEATURE                  Location/Qualifiers
misc_feature             1..5418
                         note = JG1211: CAG-human dLbCpf1(D832A)-NLS-3xHA-VPR
source                   1..5418
                         mol_type = other DNA
                         organism = synthetic construct
SEQUENCE: 52
atgagcaagc tggagaagtt tacaaactgc tactccctgt ctaagaccct gaggttcaag    60
gccatccctg tggcaagac ccaggagaac atcgacaata gcggctgct ggtggaggac      120
gagaagagag ccgaggatta agggcgtg aagaagctgc tggatcgcta ctatctgtct      180
tttatcaacg acgtgctgca cagcatcaag ctgaagaatc tgaacaatta catcagcctg    240
ttccggaaga aaccagaac cgagaaggag aataaggagc tggagagatc aat           300
ctgcggaagg agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttcc ggtgtatcaa cgagaatctg    540
accccgctaca tctctaatat ggacatcttc gagaaggtgg acgccatctt tgataagcac    600
gaggtgcagg agatcaagga agatctctg aacagcgact atgatgtgga ggatttcttt    660
gagggcgagt tctttaactt tgtgctgaca caggagggca tcgacgtgta taccgccatc    720
atcggcggct tctgtgaccga gagcggcgag aagatcaagg gcctgaacga gtacatcaac    780
ctgtataatc agaaaaccaa gcagaagctg cctaagttta agcccactgta taagcaggtg    840
ctgagcgatc gggagtctct gagccttctac ggcgagggct atacatccga tgaggaggtg    900
ctggaggtgt tagaaacac cctgaacaag aacagcgaga tcttcagctc catcaagaag    960
ctggagaagc tgttcaagga ttttgacgag tactctagcg ccggcatctt tgtgaagaac    1020
ggccccgcca tcagcacaat ctccaaggat atcttcggcga gtgtgaacgt gatccgggac    1080
aagtggaatg ccgagtatga cgatatccac ctgaagaaga aggccgtggt gaccgagaag    1140
tacgaggacg atcggagaaa gtcccttcaag aagatcggct cctttctct ggagcagctg    1200
caggagtacg ccgacgccga tctgtctgtg gtggagaagc tgaaggagat catcatccag    1260
aaggtggata gatctcaaa ggtgatggc tcctctgaga agctgttcga cgccgatttt    1320
gtgctggaga gagcctgaa aagaaacgac gccgtggtgg ccatcatgaa ggacctgctg    1380
gattctgtga gagcttcga gaattacatc aaggccttct ttggcgaggg caaggagaca    1440
aacaggacg agtccttcta tggcgatttt gtgctggcct acgacatcct gctgaaggtg    1500
gaccacatct acgatgccat ccgcaattat gtgacccaga agccctactc taaggataag    1560
ttcaagctgt attttcagaa ccctcagttc atgggcggct gggacaagga taaggagaca    1620
gactatcggg ccaccatcct gagatacggg tccaagtact atctggccat catggataag    1680
aagtacgcca agtgcctgca gaagatcgac aaggacgatg tgaacggcaa ttacgagaag    1740
atcaactata agctgctgcc cggccctaat aaagtgctgc caaaggtgtt cttttctaag    1800
aagtggatgg cctactataa ccccagcgag gacatccaga gatctacaa gaatggcaca    1860
ttcaagaagg gcgatatgtt taacctgaat gactgtcaca agctgatcga cttcttcaag    1920
gatagcatct cccggtatcc aaagtggtcc aatgcctacg atttcaactt ttctgagaca    1980
gagaagtata ttaggacatcgc cggctttttac agagaggtgg aggagcaggg ctataaggtg    2040
agcttcgagt ctgccagcaa aaaggaggtg gataagctgg tggaggaggg caagctgtat    2100
atgttccaga tctataacaa ggactttccc gataagtctc acggcacacc caatctgcac    2160
accatgtact tcaagctgct gtttgacgag aacaatcacg acagatcag gctgagcgga    2220
ggagcagagc tgttcatgag gcgcgcctcc ctgaagaagg aggagctggt ggtgcaccca    2280
gccaactccc ctatcgccaa caagaatcca gataatccca gaaaaaccac aacctgtcc    2340
tacgacgtgt ataaggataa gaggttttct gaggaccagt acgagctgca catcccaatc    2400
gccatcaata agtgccccaa gaacatcttc aagatcaata caggtgcg cgtgctgctg    2460
aagcacgacg ataaccccta tgatcggca atcgccaggg gcgacgcaa tctgctgtat    2520
atcgtggtgg tggacggcaa gggcaacatc gtggagcagt attcccgaa cgagatcatc    2580
aacaacttca cgggcatcag gatcaagaca gattaccact ctctgctgga caagaaggag    2640
aaggagaggt cgaggcccg ccagaactgg acctccatcg agaatatcaa ggagctgaag    2700
gccggctata tctctcaggt ggtgcacaag atctgcgag tggtgagaa gtacgatgcc    2760
gtgatcgccc tggaggacct gaactctggc tttaagaata gccgcgtgaa taggaagctg    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta aagtccatgtc tacccagaac ggcttcatct ttacatccc tgcctggctg    3000
acatccaaga tcgatccatc taccggcttt gtgaactgc tgaaaccaa gtataccagc    3060
atcgccgatt ccaagaagtt catcagctcc tttgacagga tcatgtacgt gcccgagga    3120
gatctgttcg agtttgccct ggactataag aacttctctc gcacagacgc cgattacatc    3180
aagaagtgga gctgtactc ctacggcaac cggatcagaa tcttccgaa tcctaagaag    3240
aacaacgtgt tcgactggga ggaggtgtgc ctgaccagcg cctataagga gctgttcaac    3300
aagtacggca tcaattatca gcaggcgat atcagagccc tgctgtgcga gcagtccgac    3360
aaggcctct actctagctt tatgccctt atgccgtgga cggaacagc                  3420
atcacaggcc gcaccgacgt ggattttctg atcagccctg tgaagaactc cgacggcatc    3480
ttctacgata ccggaactta tgaggcccag gagaatgcca cctgccaaa gaacgccgac    3540
gccaatggcg cctataacat cgccagaaag gtgctgtggg catcggcca gttcaagaag    3600
gccgaggacg agaagctgga taggtgaag atcgccatct caacaagga gtggctggag    3660
tacgcccaga ccagcgtgaa gcacaaaagg ccggcggcca cgaaaaggc cggccaggca    3720
```

```
aaaaagaaaa agggatccta cccatacgat gttccagatt acgcttatcc ctacgacgtg   3780
cctgattatg catacccata tgatgtcccc gactatgccg gaagcgaggc cagcggttcc   3840
ggacgggctg acgcattgga cgattttgat ctggatatgc tgggaagtga cgccctcgat   3900
gattttgacc ttgacatgct tggttcggat gcccttgatg actttgacct cgacatgctc   3960
ggcagtgacg cccttgatga tttcgacctg gacatgctga ttaactctag aagttccgga   4020
tctccgaaaa agaaacgcaa agttggtagc cagtacctgc ccgacaccga cgaccggcac   4080
cggatcgagg aaaagcggaa gcggacctac gagacattca agagcatcat gaagaagtcc   4140
cccttcagcg gccccaccga ccctagacct ccacctagaa gaatcgccgt gcccagcaga   4200
tccagcgaca gcgtgccaaa acctgccccc cagccttacc ccttcaccag cagcctgagc   4260
accatcaact acgacgagtt ccctaccatg gtgttcccca gcggccagat ctctcaggcc   4320
tctgctctgg ctccagcccc tcctcaggtg ctgcctcagg ctcctgctcc tgcaccagct   4380
ccagccatgg tgtctgcact ggctcaggca ccagcacccg tgcctgtgct ggctcctgga   4440
cctccacagg ctgtggctcc accagcccct aaacctacac aggccggcga gggcacactg   4500
tctgaagctc tgctgcagct gcagttcgac gacgaggatc tgggagccct gctgggaaac   4560
agcaccgatc tgccgtgtt caccgacctg gccagcgtgg acaacagcga gttccagcag   4620
ctgctgaacc agggcatccc tgtggcccct cacaccaccg agcccatgct gatggaatac   4680
cccgaggcca tcacccggct cgtgacaggc gctcagaggc tcctgatcc agctcctgcc   4740
cctctgggag caccaggcct gcctaatgga ctgctgctg gcgacgagga cttcagctgt   4800
atcgccgata tggattttct agccttgctg ggctctggca gcggcagccg ggattccagg   4860
gaagggatgt ttttgccgaa gcctgaggcc ggctccgcta ttagtgacgt gtttgagggc   4920
cgcgaggtgt gccagccaaa acgaatccgg ccatttcatc ctccaggaag tccatgggcc   4980
aaccgcccac tccccgccag cctcgcacca acaccgtcca gtaca tgagccagtc   5040
gggtcactga ccccggcacc agtccctcag ccactggatc cagcgcccgc agtgactccc   5100
gaggccagtc acctgttgga ggatcccgat aagagacga gccaggctgt caaagccctt   5160
cgggagatgg ccgatactgt gattcccag aaggaagagg ctgcaatctg tggccaaatg   5220
gaccttttccc atccgccccc aaggggccat ctggatgagc tgacaaccac acttgagtcc   5280
atgaccgagg atctgaacct ggactcaccc ctgaccccgg aattgaacga gattctggat   5340
accttcctga cgacgagtg cctcttgcat gccatgcata tcagcacagg actgtccatc   5400
ttcgacacat ctctgttt                                                5418

SEQ ID NO: 53          moltype = DNA   length = 4245
FEATURE                Location/Qualifiers
misc_feature           1..4245
                       note = JG674: CAG-human dLbCpf1(D832A)-NLS-3xHA-DmrA(X1)
source                 1..4245
                       mol_type = other DNA
                       organism = synthetic construct
SEQUENCE: 53
atgagcaagc tggagaagtt tacaaactgc tactccctgt ctaagaccct gaggttcaag     60
gccatccctg tggcaagac ccaggagaac atcgacaata gcggctgct ggtggaggac      120
gagaagagag ccgaggatta agggcgtg aagaagctgc tggatcgcta ctatctgtct      180
tttatcaacg acgtgctgca cagcatcaag ctgaagaatc tgaacaatta catcagcctg     240
ttccgaagaa aaccagaac cgagaaggag aataaggagc tggagatcaat             300
ctgcggaagg agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct tctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga gaagatcctg aacagcgact atgatgtgga ggatttcttt    660
gagggcgagt tctttaactt tgtgctgaca caggagggca tcgacgtgta taacgccatc    720
atcggcggct tctgtgaccga gagcggcgag aagatcaagg gcctgaacga gtacatcaac    780
ctgtataatc agaaaaccaa gcagaagctg cctaagttta gccactgta taagcaggtc    840
ctgagcgatc gggagtctct gagcttctac ggcgagggct acatccga tgaggaggtg     900
ctggaggtgt tagaaacac cctgaacaag acagcgaga tcttcagctc catcaagaag     960
ctggaaagc tgttcaagaa ttttgacgag tactctagcc ccggcatctt tgtgaagaac   1020
ggcccccgca tcagcacat ctccaaggat atcttcggcg agtggaacgt gatccggaca    1080
aagtggaatg ccgagtatga cgatatccac ctgaagaaga aggccgtggt gaccgagaag  1140
tacgaggacg atcggagaaa gtccttcaag aagatcggct cctttctct ggagcagctg   1200
caggagtacg ccgacgccaa tctgtctgtg tggagaagc tgaaggagat catcatccag   1260
aaggtggatg agatctacaa ggtgtatggc tcctctgaga gctgtttcga cgccgatttt    1320
gtgctggaga gagcctgaa gaagaacgac gccgtggtgg ccatcatgaa ggacctgctg   1380
gattctgtga gagcttcga gaattacatc aaggccttct tggcggaggg caaggagaca   1440
aacagggacg agtccttcta tggcgattt tgtctggcct acgacatcct gctgaaggtg   1500
gaccacatct acgatgccat ccgcaattat gtgacccaga agccctacta taagggataag   1560
ttcaagctgt atttcagaa ccctcagttc atgggcggct gggacaagga taaggagaca    1620
gactatcggg ccaccatcct gagatacggc tccaagtact atctggccat catggataag   1680
aagtacgcca gtgcctgca agatcgacaa aggacgatg tgaacggcaa ttacgagaag    1740
atcaactata gctgctgcc cggccctaat aagatgctgc caaaggtgtt cttttctaag    1800
aagtggatg cctactataa ccccagcgag gatatccaa gaatggcaca                1860
ttcaagaag gcgatatgtt taacctgaat gactgtcaca agctgatcga cttctttaag   1920
gatagcatct cccggtatc aaagtggtcc aatgcctacg atttcaactt ttctgagaca   1980
gagaagtata aggacatcgc cggcttttac agagagtgg aggagcaggg ctataaggtc    2040
agcttcgagt ctgccagcaa gaaggaggtg gataagctgg tggaggagg caagctgtat   2100
atgttccaga tctataacaa ggacttttcc gaaagtctc acggcacacc caatgctgac   2160
accatgtact tcaagctgct gtttgacgag aacaatcacg acagatcag gctgagcgga    2220
ggagcagagc tgttcatgag gcgccctcc ctgaagaagg aggagctgg ggtgcaccca     2280
gccaactccc ctatcgccaa caagaatcca gataatccca gaaaccac aaccctgtcc    2340
tacgacgtgt ataaggataa gaggtttctc gaggaccagt acgagctgca catccccaatc  2400
gccatcaata gtgccccaa gaacatcttc aagatcaata cagaggtgcg cgtgctgctg   2460
```

```
aagcacgacg ataaccccta tgtgatcggc atcgccaggg gcgagcgcaa tctgctgtat  2520
atcgtggtgg tggacggcaa gggcaacatc gtggagcagt attccctgaa cgagatcatc  2580
aacaacttca acggcatcag gatcaagaca gattaccact ctctgctgga caagaaggag  2640
aaggagaggt tcgaggcccg ccagaactgg acctccatcg agaatatcaa ggagctgaag  2700
gccggctata tctctcaggt ggtgcacaag atctgcgagc tggtggagaa gtacgatgcc  2760
gtgatcgccc tggaggacct gaactctggc tttaagaata gccgcgtgaa ggtggagaag  2820
caggtgtatc agaagttcga gaagatgctg atcgataagc tgaactacat ggtggacaag  2880
aagtctaatc cttgtgcaac aggcggcgcc ctgaagggct atcagatcac caataagttc  2940
gagagcttta agtccatgtc tacccagaac ggcttcatct tttacatccc tgcctggctg  3000
acatccaaga tcgatccatc taccggcttt gtgaacctgc tgaaaaccaa gtataccagc  3060
atcgccgatt ccaagaagtt catcagctcc tttgacagga tcatgtacgt gcccgaggag  3120
gatctgttcg agtttgccct ggactataag aacttctctc gcacagacgc cgattacatc  3180
aagaagtgga agctgtactc ctacggcaac cggatcagaa tcttccggaa tcctaagaag  3240
aacaacgtgt tcgactggga ggaggtgtgc ctgaccagcc cctataagga gctgttcaac  3300
aagtacggca tcaattatca gcagggcgat atcagagccc tgctgtgcga cagtccgac   3360
aaggccttct actctagctt tatggcccct atgagcctga tgctgcagat gcggaacagc  3420
atcacaggcc gcaccgacgt ggattttctg atcagccctg aagaactcga cggcatc    3480
ttctacgata gccggaacta tgaggcccag gagaatgcca tcctgccaaa gaacgccgac  3540
gccaatggcg cctataacat cgccagaaaa gtgctgtggg ccatcggcca gttcaagaag  3600
gccgaggacg agaagctgga taaggtgaag atcgccatct ctaacaagga gtggctggag  3660
tacgcccaga ccagcgtgaa gcacaaaagg ccggcggcca cgaaaaaggc cggccaggca  3720
aaaaagaaaa agggatccta cccatacgat gttccagatt acgcttatcc ctacgacgtg  3780
cctgattatg catacccata tgatgtcccc gactatgcct cgagcgacta caaagaccat  3840
gacggtgatt ataaagatca tgacatcgat tacaaggatg acgatgacaa ggctgcagga  3900
ggcggtggaa gcgggagggg agtgcaggtg gaaaccatct ccccaggaga cgggcgcacc  3960
ttccccaagc gcggccagac ctgcgtggtc cactacaccg ggatgcttga agatggaaag  4020
aaatttgatt cctcccggga cagaaacaag ccctttaagt ttatgctagg caagcaggag  4080
gtgatccgag gctgggaaga aggggttgcc cagatgagtg tgggtcagag agccaaactg  4140
actatatctc cagattatgc ctatggtgcc actgggcacc caggcatcat cccaccacat  4200
gccactctcg tcttcgatgt ggagcttcta aaactggaag gataa                 4245
```

```
SEQ ID NO: 54            moltype = DNA    length = 4575
FEATURE                  Location/Qualifiers
misc_feature             1..4575
                         note = JG676: CAG-human dLbCpf1(D832A)-NLS-3xHA-DmrA(X2)
source                   1..4575
                         mol_type = other DNA
                         organism = synthetic construct
SEQUENCE: 54
atgagcaagc tggagaagtt tacaaactgc tactccctgt ctaagaccct gaggttcaag   60
gccatccctg tgggcaagac ccaggagaac atcgacaata gcggctgct ggtggaggac   120
gagaagagag ccgaggatta agggcgtg aagaagctgc tggatcgcta ctatctgtct    180
tttatcaacg acgtgctgca cagcatcaag ctgaagaatc catcagcttg              240
ttccggaaga aaaccagaac cgagaaggag aataaggagc tggagaacct ggagatcaat  300
ctgcggaagg agatcgccaa ggccttcaag ggcaacgagg ctacaagtc cctgtttaag   360
aaggatatca tcgagacaat cctgccagag ttcctggacg ataaggacga gatcgccctg  420
gtgaacagct tcaatggctt taccacagcc ttcaccgatc tctttgataa cagagagaat  480
atgtttcccg aggaggccaa gagcacatcc atcgccttca ggtgtatcaa cgagaatctg  540
acccgctaca tctctaatat ggacatcttc gagaaggtgg acgccatctt tgataagcac  600
gaggtgcagg agatcaagga agatcctg aacagcgact atgatgtgga ggattctcttt   660
gagggcgagt tcttaactt tgtgctgaca caggagggca tcgacgtgta taacgccatc   720
atcggcggct tcgtgaccga gagcggcgag aagatcaagg gcctgaacga gtacatcaac  780
ctgtataatc agaaaaccaa gcagaagctg cctaagtta agccactgta taagcaggtg  840
ctgagcgatc gggagtctct gagcttctac ggcgagggc atacatccga tgaggaggtg   900
ctggaggtgt ttagaaacac cctgaacaag aacagcgagt cttcagctc catcaagaag   960
ctggaagagc tgttcaagaa ttttgacgag tactctagcg ccggcatctt tgtgaagaac  1020
ggccccgcca tcagcacaat ctccaaggat atcttcggcg agtggaacgt gatccgggac  1080
aagtggaatc cgagtatga cgatatccac ctgaagaaga aggccgtggt gaccgagaag  1140
tacgaggacg atcggagaaa gtccttcaag aagatcggct ccttttctct ggagcagtcg  1200
caggagtacg ccgacgccga tctgtctgtg gtggagaatc tgaaggagat catcatccag  1260
aaggtggatg agatctacaa ggtgtatgc tcctctgaga agctgttcga cgccgatttt    1320
gtgctggaga gagcctgaa gaagaacgac gccgtggtgg ccatcatgaa ggacctgctg  1380
gattctgtga gagcttcga gaattacatc aaggccttct ttggcgaggg caaggagaca  1440
aacagggacg agtcctccta tggcgatttt gtgctggcca agatccct gctgaaggtg   1500
gaccacatct acgatgccat ccgcaattat gtgacccaga gcccctactc taaggataag  1560
ttcaagctgt attttcagaa ccctcagttc atgggcggct gggacaagga taaggataca  1620
gactatcggg ccaccatcct gagatacggc tccaagtact atctggccat catggataag  1680
aagtacgcca agtgcctgca gaagatcgac aaggacgatg tgaacggcaa ttacgagaag  1740
atcaactata agctgctgcc cggcccaat aagatgctgcc caaaggtgtt cttttctaag  1800
aagtggatgg cctactataa ccccagcgag gacatccaga agatctacaa gaatggcaca  1860
ttcaagaagg gcgatatgtt taacctgaat gactgtcaca agctgatcga cttcttcaag  1920
gatagcatct cccggtatcc aaagtggtcc aatgcctacg atttcaactt ttctgagaca  1980
gagaagtata aggacatcgc cggcttttac agagaggtgg aggagcaggg ctataaggtg  2040
agcttcgagt ctgccagcaa gaaggaggtg gataagtaca gtggaagctg tccaagctgtat  2100
atgttccaga tctataacaa ggacttttc gataagtctc acggcacacc caatctgcac  2160
accatgtact tcaagctgct gtttgacgag aacaatcacg acagatcag gctgagcgga  2220
ggagcagagc tgttcatgag gcgcgcctcc ctgaagaagg aggagctggt ggtgcaccca  2280
gccaactccc ctatcgccaa caagaatcca gataatccca gaaaaccac aaccctgtcc  2340
tacgacgtgt ataaggataa gaggttttct gaggaccagt acgagctgca catcccaatc  2400
```

```
gccatcaata agtgcccccaa gaacatcttc aagatcaata cagaggtgcg cgtgctgctg    2460
aagcacgacg ataaccccta tgtgatcggc atcgccaggg gcgagcgcaa tctgctgtat    2520
atcgtggtgg tggacggcaa gggcaacatc gtggagcagt attccctgaa cgagatcatc    2580
aacaacttca acggcatcag gatcaagaca gattaccact ctctgctgga caagaaggag    2640
aaggagaggt tcgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta gtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga gctgtactc ctacggcaac cggatcaaga tcttccggaa tcctaagaag    3240
aacaacgtgt tcgactggga ggaggtgtgc ctgaccagcg cctataagga gctgttcaac    3300
aagtacggca tcaattatca gcagggcgat atcagagccc tgctgtgcga gcagtccgac    3360
aaggccttct actctagctt tatggccctg atgagctga tgctgcagat gcggaacagc    3420
atcacaggcc gcaccgacgt ggattttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg ccggcggcca gcaaaaaggc cggccaggca    3720
aaaaagaaaa agggatccta cccatacgat gttccagatt acgcttatcc ctacgacgtg    3780
cctgattatg cataccccata tgatgtcccc gactatgcct cgagcgacta caaagaccat    3840
gacggtgatt ataagatca tgacatcgat tacaaggatg acgatgacaa ggctgcagga    3900
ggcggttgaa gcgggagggg agtgcaggtg gaaaccatct cccaggaga cgggcgcacc    3960
ttccccaagc gcggcagac ctgcgtggtg cactacaccg gatgcttga agatggaaag    4020
aaatttgatt cctcccggga cagaaacaag ccctttaagt ttatgctagg caagcaggag    4080
gtgatccgag ctgggaaga aggggttgcc cagatgagtg tgggtcagag agccaaactg    4140
actatatctc cagattatgc ctatggtgcc actgggcacc caggcatcat cccaccacat    4200
gccactctcg tcttcgatgt ggagcttcta aaactggaag gttctagggg agtgcaggtg    4260
gaaaccatct cccaggaga cgggcgcacc ttccccaagc gcggcagac ctgcgtggtg    4320
cactacaccg gatgcttga agatggaaag aaatttgatt cctcccggga cagaaacaag    4380
ccctttaagt ttatgctagg caagcaggag gtgatccgag ctgggaaga aggggttgcc    4440
cagatgagtg tgggtcagag agccaaactg actatatctc cagattatgc ctatggtgcc    4500
actgggcacc caggcatcat cccaccacat gccactctcg tcttcgatgt ggagcttcta    4560
aaactggaag gataa                                                    4575

SEQ ID NO: 55          moltype = DNA   length = 4917
FEATURE                Location/Qualifiers
misc_feature           1..4917
                       note = JG693: CAG-human dLbCpf1(D832A)-NLS-3xHA-DmrA(X3)
source                 1..4917
                       mol_type = other DNA
                       organism = synthetic construct
SEQUENCE: 55
atgagcaagc tggagaagtt tacaaactgc tactccctgt ctaagaccct gaggttcaag    60
gccatccctg tggcaagac ccaggagaac atcgacaata gcggctgct ggtggaggac    120
gagaagagag ccgaggatta agggcgtga agaagctgc tggatcgcta ctatctgtct    180
tttatcaacg acgtgctgca cagcatcaag ctgaagaatc tgaacaatta catcagcctg    240
ttccggaaga aaaccagaac cgagaaggag aataaggagc tggagaacct ggagatcaat    300
ctgcggaagg agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct ctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt gataagcac    600
gaggtgcagg atcaagga gaagatcctg aacagcgact atgatgtgga ggatttcttt    660
gagggcgagt ctctttaactt tgtgctgaca caggagggca tcgacgtgta acgccatc    720
atcgcgggct tcgtgaccga gagcggcgag aagatcaagg gcctgaacga gtacatcaac    780
ctgtataatc agaaaaccaa gcagaagctg cctaagttta gccactgta taagcaggc    840
ctgagcgatc gggagtctct gagcttctac ggcgagggct atacatccga tgaggaggtg    900
ctggaggtgt ttagaaacac cctgaacaag aacagcgaga tcttcagctc catcaagaag    960
ctggagaagc tgttcaagaa ttttgacgag tactctagcg ccggcatctt tgtgaagaac    1020
ggcccgcca tcagcacaat ctccaaggat atcttgga agtgaactg gatcggtgac    1080
aagtggaatg ccgagtatga cgatatccac ctgaagaaga aggccgtggt gaccgagaag    1140
tacgaggacg atcggagaaa gtccttcaag aagatcggtc ccttttctct ggagcagctg    1200
caggagtacg ccgacgccga tctgtctgtg gtggagaagc tgaaggagat catcatccag    1260
aaggtggatg agatctacaa ggtgtatgcg tcctctgaga gctgttcga cgccgatttt    1320
gtgctggaga gagcctgaa gaagaacgac gccgtgctg ccatcatgaa ggacctgctg    1380
gattctgtga gagcttcga gaattacatc aaggccttct ttggcgaggg caaggagaca    1440
aacagggacg agtccttcta tggcgatttt gtgctggcct acgacatcct gctgaaggtg    1500
gaccacatct acgatgccat ccgcaattat gtgacccaga gccctactc taaggataag    1560
ttcaagctgt attttcagaa ccctcagttc atgggcggct gggacaagga taggagaca    1620
gactacggcc accatcct gatacggc tccaagtact catgaataag    1680
aagtacgcca gtgcctgca gaagatcgac aaggacgatg tgaacggcaa ttacgagaag    1740
atcaactata gctgctgcc cggccctaat aagatgctgc caaaggtgtt cttttctaag    1800
aagtggatgg cctactataa ccccagcgag gacatccaga gatctacaa gaatggcaca    1860
ttcaagaagg gcgatatgtt taacctgaat gactgtcaca agctgatcga cttctttaag    1920
gatagcatct cccggtatcc aaaagtggtcc aatgcctacg atttcaactt ttctgagaca    1980
```

-continued

```
gagaagtata aggacatcgc cggcttttac agagaggtgg aggagcaggg ctataaggtg    2040
agcttcgagt ctgccagcaa gaaggaggtg gataagctgg tggaggaggg caagctgtat    2100
atgttccaga tctataacaa ggacttttcc gataagtctc acggcacacc caatctgcac    2160
accatgtact tcaagctgct gtttgacgag aacaatcacg acagatcag gctgagcgga     2220
ggagcagagc tgttcatgag gcgcgcctcc ctgaagaagg aggagctgtt ggtgcaccca    2280
gccaactccc ctatcgccaa caagaatcca gataatccca agaaaaccac aaccctgtcc    2340
tacgacgtgt ataaggataa gaggttttct gaggaccagt acgagctgca catcccaatc    2400
gccatcaata agtgccccaa gaacatcttc aagatcaata cagaggtgcg cgtgctgctg    2460
aagcacgacg ataaccccta tgtgatcggc atcgccaggg gcgagcgcaa tctgctgtat    2520
atcgtggtgg tggacggcaa gggcaacatc gtggacagt attccctgaa cgagatcatc    2580
aacaacttca acggcatcag gatcaagaca gattaccact ctctgctgga caagaaggag    2640
aaggagaggt cgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgacggaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta agtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagagcg cgattacatc    3180
aagaagtgga gctgtactc ctacggcaac cggatcagaa tcttccggaa tcctaagaag    3240
aacaactgt tcgactggga ggaggtgtgc ctgaccagcc cctataagga gctgttcaac    3300
aagtacggca tcaattatca gcagggcgat atcagagccc tgctgtgcga cagtccgac    3360
aaggccttct actctagctt tatggccctg atgagcctga tgctgcagat gcggaacagc    3420
atcacaggcc gcaccgacgt ggattttctg atcagccctg tgaagaactc cgacggcatc    3480
ttctacgata gccggaacta tgaggccgag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg ccggcggcca cgaaaaggc cggccaggca    3720
aaaaagaaaa agggatccta cccatacgat gttccagatt acgcttatcc ctacgacgtg    3780
cctgattatg catacccata tgatgtcccc gactatgcct cgagcgacta caaagaccat    3840
gacggtgatt ataagatca tgacatcgat tacaaggatg acgatgacaa ggctgcagga    3900
ggcggtggaa gcgggagggg agtgcaggtg gaaaccatct ccccaggaga cgggcgcacc    3960
ttccccaagc gcggccagac ctgcgtggtg cactacacag gggatgcttg agatggaaag    4020
aaatttgatt cctcccggga cagaaacaag cccttaagt ttatgctagg caagcaggag    4080
gtgatccgag gctgggaaga aggggttgcc cagatgagtg tgggtcagag agccaaactg    4140
actatatctc cagattatgc ctatggtgcc actgggcacc caggcatcat cccaccacat    4200
gccactctcg tcttcgatgt ggagcttcta aaactgaag gatctggtgg aagcggggagg    4260
ggagtgcagg tggaaaccat ctccccagga cgggcgcca ccttcccaa gcgcggccag    4320
acctgcgtgg tgcactacac cgggatgctt gaagatggaa agaaatttga ttcctcccgg    4380
gacagaaaca gcccttaa gtttatgcta ggcaagcagg aggtgatccg aggctgggaa    4440
gaaggggttg cccagatgag tgtgggtcag agagccaaac tgactatatc tcagattat    4500
gcctatggtg ccactgggca cccaggcatc atccaccac cgccactctc cgtcttcgat    4560
gtggagcttc taaaactgga aggttctagg ggagtgcagg tggaaaccat ctccccagga    4620
gacgggcgca ccttccccaa gcgcggccag acctgcgtgg tgcactacac cgggatgctt    4680
gaagatggaa agaaatttga ttcctcccgg gacagaaaca gcccttaa gtttatgcta    4740
ggcaagcagg aggtgatccg aggctgggaa gaaggggttg cccagatgag tgtgggtcag    4800
agagccaaac tgactatatc tcagattat gcctatggtg ccactgggca cccaggcatc    4860
atccaccac atgccactct cgtcttcgat gtggagcttc taaaactgga aggataa      4917
```

SEQ ID NO: 56          moltype = DNA   length = 5253
FEATURE                Location/Qualifiers
misc_feature           1..5253
                       note = YET1000: CAG-human dLbCpf1(D832A)-NLS-3xHA-DmrA(X4)
source                 1..5253
                       mol_type = other DNA
                       organism = synthetic construct
SEQUENCE: 56

```
atgagcaagc tggagaagtt tacaaactgc tactccctgt ctaagaccct gaggttcaag     60
gccatccctg tgggcaagac ccaggagaac atcgacaata gcggctgct ggtggaggac    120
gagaagagag ccgaggatta aagggcgtg aagaagctgc tggatcgcta ctatctgtct    180
tttatcaacg acgtgctgca cagcatcaag ctgaagaatc tgaacaatta catcagcctg    240
ttccggaaga aaaccagaac cgagaaggag aataaggagc tggagaacct ggagatcaat    300
ctgcggaagg agatcgccaa ggccttcaag ggcaacgagg gctacaagtc cctgtttaag    360
aaggatatca tcgagacaat cctgccagag ttcctggacg ataaggacga gatcgccctg    420
gtgaacagct tcaatggctt taccacagcc ttcaccggct ctttgataa cagagagaat    480
atgttttccg aggaggccaa gagcacatcc atcgccttca ggtgtatcaa cgagaatctg    540
acccgctaca tctctaatat ggacatcttc gagaaggtgg acgccatctt tgataagcac    600
gaggtgcagg agatcaagga agatctcagc aacaggact atgatgtgga ggatttcttt    660
gagggcgagt tctttaactt tgtgctgaca caggagggca tcgacgtgta taacgccatc    720
atcggcggct tcgtgaccga gagcggcgag aagatcaagg gcctgaacga gtacatcaac    780
ctgtataatc agaaaaccaa gcagaagctg cctaagttta gccactgta taagcaggtg    840
ctgagcgatc gggagtctct gagcttctac ggcgagggct acatccga tgaggaggtg    900
cggagggtta ttagaaacac cctgaacaag aacagcgagc ttcagcgtc catcaagaag    960
ctggagaagc tgttcaagaa ttttgacgag tactctagcg ccggcatctt tgtgaagaac    1020
ggccccgcca tcagcacaat ctccaaggat atcttcggcg agtggaacgt gatcggggac    1080
aagtggaatg ccgagtatga cgatatccac ctgaagaaga ggccgtggt gaccgagaag    1140
tacgaggacg atcggagaaa gtccttcaag aagatcggct ccttttctct ggagcagctg    1200
caggagtacg ccgacgccga tctgtctgtg gtggagaagc tgaaggagat catcatccag    1260
```

```
aaggtggatg agatctacaa ggtgtatggc tcctctgaga agctgttcga cgccgatttt    1320
gtgctggaga agagcctgaa gaagaacgac gccgtggtgg ccatcatgaa ggacctgctg    1380
gattctgtga agagcttcga gaattacatc aaggccttct ttggcgaggg caaggagaca    1440
aacagggacg agtccttcta tggcgatttt gtgctggcct acgacatcct gctgaaggtg    1500
gaccacatct acgatgccat ccgcaattat gtgacccaga agccctactc taaggataag    1560
ttcaagctgt attttcagaa ccctcagttc atgggcggct gggacaagga taaggagaca    1620
gactatcggg ccaccatcct gagatacggc tccaagtact atctggccat catggataag    1680
aagtacgcca agtgcctgca gaagatcgac aaggacgatg tgaacggcaa ttacgagaag    1740
atcaactata agctgctgcc cggccctaat aagatgctgc caaaggtgtt cttttctaag    1800
aagtggatgg cctactataa ccccagcgag gacatccaga agatctacaa gaatggcaca    1860
ttcaagaagg cgatatgtt taacctgaat gactgtcaca agctgatcga cttctttaag    1920
gatagcatct cccggtatcc aaagtggtcc aatgcctacg atttcaactt ttctgagaca    1980
gagaagtata aggacatcgc cggcttttac agagaggtgg aggagcaggg ctataaggtg    2040
agcttcgagt ctgccagcaa gaaggaggtg gataagctag gagggaggg caagctgtat    2100
atgttccaga tctataacaa ggacttttcc gataagtctc acggcacacc caatctgcac    2160
accatgtact tcaagctgct gtttgacgag aacaatcacg gacagatcag gctgagcgga    2220
ggagcagagc tgttcatgag gcgcgcctcc ctgaagaagg aggagctggt ggtgcaccca    2280
gccaactccc ctatccgcaa caagaatcca gataatccca agaaaaccaa aaccctgtcc    2340
tacgacgtgt ataaggataa gaggtttct gaggaccagt acgagctgca catcccaatc    2400
gccatcaata agtgccccaa gaacatcttc aagatcaata cagaggtgcg cgtgctgctg    2460
aagcacgacg ataaccccta tgtgatcggc atcgccaggg gcgagcgcaa tctgctgtat    2520
atcgtggtgg tggacggcaa gggcaacatc gtggagcagt attccctgaa cgagatcatc    2580
aacaacttca acggcatcag gatcaagaca gattaccact ctctgctgga caagaaggag    2640
aaggagaggt tcgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta agtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga agctgtactc ctacggcaac cggatcagaa tcttccggaa tcctaagaag    3240
aacaacgtgt tcgactggga ggaggtgtgc ctgaccagcg cctataagga gctgttcaac    3300
aagtacggca tcaattatca gcagggcgat atcaagccc tgctgtgcga gcagtccgac    3360
aaggccttct actctagctt tatggccctg atgagcctga tgctgcagat cggaacagc    3420
atcacaggcc gcaccgacgt ggattttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg ccggcggcca cgaaaaaggc cggccaggca    3720
aaaaagaaaa agggatccta cccatacgat gttccagatt acgcttatcc ctacgacgtg    3780
cctgattatg catacccata tgatgtcccc gactatgcct acgacgacta caaagaccat    3840
gacggtgatt ataaagatca tgacatcgat tacaaggatg acgatgacaa ggctgcagga    3900
ggcggtggaa gcggggggaag gggagtgcag gtggaaacca tctcccccagg agacgggcgc    3960
accttcccca agcgcggcca gacctgcgtg gtgcactaca ccgggatgct tgaagatgga    4020
aagaaatttg attcctcccg ggacagaaac aagcccttta gtttatgct aggcaagcag    4080
gaggtgatcc gaggctggga agaagggggtt gcccagatga gtgtgggtca gagagccaaa    4140
ctgactatat ctccagatta tgcctatggt gccactgggc acccaggcat catcccacca    4200
catgccactc tcgtcttcga tgtggagctt ctaaaactgg aaggttctag gggagtgcag    4260
gtggaaacca tctcccaggg agacgggcgc acctttccca agcgcggcca gacctgcgtg    4320
gtgcactaca ccgggatgct tgaagatgga aagaaatttg attcctcccg ggacagaaac    4380
aagcccttta gtttatgct aggcaagcag gaggtgatcc gaggctggga agaagggtt    4440
gcccagatga gtgtgggtca gagagccaaa ctgactatat ctccagatta tgcctatggt    4500
gccactgggc acccaggcat catcccacca catgccactc tcgtcttcga tgtggagctt    4560
ctaaaactgg aaggggggaag cggtggaagc gggaggggag tgcaggtgga aaccatctcc    4620
ccaggagacg ggcgcacctt ccccaagcgc ggccagacct gcgtggtgca ctaccgggg    4680
atgcttgaag atggaaagaa atttgattcc tcccgggaca gaaacaagcc ctttagttt    4740
atgctaggca agcaggaggt gatcgaggc tgggaagaag gggttgccca gatgagtgtg    4800
ggtcagagag ccaaactgac tatatctcca gattatgcct atggtgccac tgggcaccca    4860
ggcatcatcc caccacatgc cactctcgtt ttcgatgtgg agcttctaaa actgaaggt    4920
tctagggag tgcaggtgga aaccatctcc caggacg gcgcacctt ccccaagcgc    4980
ggccagacct gcgtggtgca ctaccgggg atgcttgaag atggaaagaa atttgattcc    5040
tcccgggaca gaaacaagcc ctttagttt atgctaggca agcaggaggt gatcgaggc    5100
tgggaagaag gggttgccca gatgagtgtg ggtcagagag ccaaactgac tatatctcca    5160
gattatgcct atggtgccac tgggcaccca ggcatcatcc caccacatgc cactctcgtc    5220
ttcgatgtgg agcttctaaa actggaagga taa                                5253
```

SEQ ID NO: 57      moltype = DNA  length = 367
FEATURE              Location/Qualifiers
misc_feature      1..367
                         note = BPK3082: U6-Lb-crRNA-BsmBIcassette
source               1..367
                         mol_type = other DNA
                         organism = synthetic construct
SEQUENCE: 57
```
tgtacaaaaa agcaggcttt aaaggaacca attcagtcga ctggatccgg taccaaggtc     60
gggcaggaag agggcctatt tcccatgatt ccttcatatt tgcatatacg atacaaggct    120
gttagagaga taattagaat taatttgact gtaaacacaa agatattagt acaaaatacg    180
```

```
tgacgtagaa agtaataatt tcttgggtag tttgcagttt taaaattatg ttttaaaatg  240
gactatcata tgcttaccgt aacttgaaag tatttcgatt tcttggcttt atatatcttg  300
tggaaaggac gaaacaccga atttctacta agtgtagatg gagacgatta atgcgtctcc  360
tttttt                                                              367

SEQ ID NO: 58          moltype = DNA  length = 397
FEATURE                Location/Qualifiers
misc_feature           1..397
                       note = crRNAs from Figure 2b
source                 1..397
                       mol_type = other DNA
                       organism = synthetic construct
SEQUENCE: 58
gagggcctat ttcccatgat tccttcatat ttgcatatac gatacaaggc tgttagagag   60
ataattagaa ttaatttgac tgtaaacaca aagatattag tacaaaatac gtgacgtaga  120
aagtaataat ttcttgggta gtttgcagtt ttaaaattat gttttaaaat ggactatcat  180
atgcttaccg taacttgaaa gtatttcgat ttcttggctt tatatatctt gtggaaagga  240
cgaaacaccg aatttctact aagtgtagat tactgatggt atggggccaa aatttctact  300
aagtgtagat ctctaggaac cctcagcccc aatttctact aagtgtagat aagcctcggg  360
aaactgccct aatttctact aagtgtagat tttttt                            397
```